US010709866B2

(12) United States Patent
Hensman et al.

(10) Patent No.: US 10,709,866 B2
(45) Date of Patent: Jul. 14, 2020

(54) USABILITY FEATURES FOR RESPIRATORY HUMIDIFICATION SYSTEM

(71) Applicant: FISHER & PAYKEL HEALTHCARE LIMITED, Auckland (NZ)

(72) Inventors: Sally Margaret Hensman, Auckland (NZ); David Robert Kemps, Auckland (NZ); Simon Mordechai Stam, Auckland (NZ); Jason Allan Klenner, Auckland (NZ); Andrew Paul Maxwell Salmon, Auckland (NZ); Mark Samuel Hamilton, Auckland (NZ); James William Stanton, Auckland (NZ); Michael John Andresen, Auckland (NZ); Jonathan Andrew George Lambert, Auckland (NZ); Nicholas Edward Vaughan, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 761 days.

(21) Appl. No.: 15/310,407

(22) PCT Filed: May 13, 2015

(86) PCT No.: PCT/NZ2015/050054
§ 371 (c)(1),
(2) Date: Nov. 10, 2016

(87) PCT Pub. No.: WO2015/174859
PCT Pub. Date: Nov. 19, 2015

(65) Prior Publication Data
US 2017/0252531 A1 Sep. 7, 2017

Related U.S. Application Data

(60) Provisional application No. 61/992,442, filed on May 13, 2014, provisional application No. 62/032,208, (Continued)

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0069* (2014.02); *A61M 16/021* (2017.08);
(Continued)

(58) Field of Classification Search
CPC .............. A61M 16/16; A61M 16/1095; A61M 16/0875; A61M 16/109; A61M 16/162;
(Continued)

(56) References Cited

U.S. PATENT DOCUMENTS 1,154,259 A 9/1915 Light
2,745,074 A 1/1951 Darling
(Continued)

FOREIGN PATENT DOCUMENTS

AU 2000071791 3/2001
AU 2002244571 9/2002
(Continued)

OTHER PUBLICATIONS

Nov. 11, 2015 International Search Report for International Application No. PCT/NZ2015/050054.
(Continued)

*Primary Examiner* — Timothy A Stanis
*Assistant Examiner* — Margaret M Luarca
(74) *Attorney, Agent, or Firm* — Knobbe, Martens, Olson & Bear, LLP

(57) ABSTRACT

A humidification system for delivering humidified gases to a user can include a heater base, humidification chamber having an inlet, outlet, and associated fluid conduit, and breathing circuit including a supply conduit, inspiratory conduit, and optional expiratory conduit. The humidification system can include various features to help make set-up less difficult and time-consuming. For example, the supply conduit, inspiratory conduit, and optional expiratory conduit can be coupled into a one-piece circuit to aid set-up. Various components can be color-coded and can have corresponding structures to indicate which components should be connected to one another during set-up. Such features can also help make the set-up process more intuitive for an operator, which can reduce the need for specialized training and reduce the number of potential errors.

21 Claims, 66 Drawing Sheets

Related U.S. Application Data filed on Aug. 1, 2014, provisional application No. 62/127,443, filed on Mar. 3, 2015.

(51) Int. Cl.
  *A61M 16/00* (2006.01)
  *A61M 16/08* (2006.01)

(52) U.S. Cl.
  CPC .... *A61M 16/0875* (2013.01); *A61M 16/0883* (2014.02); *A61M 16/0891* (2014.02); *A61M 16/109* (2014.02); *A61M 16/1095* (2014.02); *A61M 2016/0039* (2013.01); *A61M 2205/3368* (2013.01); *A61M 2205/3379* (2013.01); *A61M 2205/50* (2013.01); *A61M 2205/502* (2013.01); *A61M 2205/584* (2013.01); *A61M 2209/00* (2013.01)

(58) Field of Classification Search
  CPC ............. A61M 16/164; A61M 16/165; A61M 16/167; A61M 16/168; B65D 85/00; F24F 2006/008; F24F 6/02
  USPC ..................................... 206/521, 320; 85/30
  See application file for complete search history.

(56) References Cited

U.S. PATENT DOCUMENTS

| | | |
|---|---|---|
| 2,634,311 A | 4/1953 | Darling |
| 3,119,541 A | 1/1964 | Lynn |
| 3,163,707 A | 12/1964 | Darling |
| 3,283,580 A | 11/1966 | Jacob et al. |
| 3,394,954 A | 7/1968 | Sarns |
| 3,485,237 A | 12/1969 | Bedford |
| 3,582,094 A | 6/1971 | Whittaker |
| 3,588,859 A | 6/1971 | Petree |
| 3,638,926 A | 2/1972 | Melville et al. |
| 3,659,604 A | 5/1972 | Melville et al. |
| 3,703,892 A | 11/1972 | Meyers |
| 3,777,298 A | 12/1973 | Newman |
| 3,903,742 A | 9/1975 | Colton |
| 3,954,920 A | 5/1976 | Heath |
| 3,987,133 A | 10/1976 | Andra |
| 3,990,727 A | 11/1976 | Gallagher |
| 4,028,444 A | 6/1977 | Brown |
| 4,038,519 A | 7/1977 | Foucras |
| 4,060,576 A | 11/1977 | Grant |
| 4,111,197 A | 9/1978 | Warncke et al. |
| 4,139,762 A | 2/1979 | Pohrer et al. |
| 4,172,709 A | 10/1979 | Kippel et al. |
| 4,183,248 A | 1/1980 | West |
| 4,333,451 A | 6/1982 | Paluch |
| 4,394,922 A | 7/1983 | Wimmer |
| 4,473,923 A | 10/1984 | Neroni et al. |
| 4,529,867 A | 7/1985 | Velnosky et al. |
| 4,545,290 A | 10/1985 | Lieberman DATE |
| 4,564,748 A | 1/1986 | Gupton |
| 4,588,425 A | 5/1986 | Usry et al. |
| 4,621,632 A | 11/1986 | Bartels et al. |
| 4,676,237 A | 6/1987 | Wood et al. |
| 4,686,354 A | 8/1987 | Makin |
| 4,708,831 A | 11/1987 | Elsworth et al. |
| 4,774,032 A | 9/1988 | Coates et al. |
| 4,813,280 A | 3/1989 | Miller, Jr. et al. |
| 4,844,512 A | 7/1989 | Gahwi Ler |
| 4,942,877 A | 7/1990 | Sakai et al. |
| 4,944,310 A | 7/1990 | Sullivan |
| 4,967,744 A | 11/1990 | Chua |
| 5,031,612 A | 7/1991 | Clementi |
| 5,058,588 A | 10/1991 | Kaestle |
| 5,060,506 A | 10/1991 | Douglas |
| 5,117,819 A | 6/1992 | Servidio et al. |
| 5,134,996 A | 8/1992 | Bell |
| 5,148,801 A | 9/1992 | Douwens et al. |
| 5,213,376 A | 5/1993 | Szabo |
| 5,303,701 A | 4/1994 | Heins et al. |
| RE34,599 E | 5/1994 | Suszynski et al. |
| 5,357,948 A | 10/1994 | Eilentropp |
| 5,367,604 A | 11/1994 | Murray |
| 5,392,770 A | 2/1995 | Clawson et al. |
| 5,454,061 A | 9/1995 | Carlson |
| 5,483,616 A | 1/1996 | Chiu et al. |
| 5,537,996 A | 7/1996 | McPhee |
| 5,551,883 A | 9/1996 | Davis |
| 5,640,951 A | 6/1997 | Huddart et al. |
| 5,660,567 A | 8/1997 | Nierlich et al. |
| 5,720,293 A | 2/1998 | Quinn et al. |
| 5,778,872 A | 7/1998 | Fukunaga et al. |
| 5,881,393 A | 3/1999 | Marchello |
| 5,906,201 A | 5/1999 | Nilson |
| 5,943,473 A | 8/1999 | Levine |
| D419,522 S | 1/2000 | Kamagai |
| 6,039,696 A | 3/2000 | Bell |
| 6,053,482 A | 4/2000 | Glenn et al. |
| 6,078,729 A | 6/2000 | Kopel |
| 6,102,037 A | 8/2000 | Koch |
| 6,105,970 A | 8/2000 | Siegrist et al. |
| 6,126,610 A | 10/2000 | Rich et al. |
| 6,138,674 A | 10/2000 | Gull et al. |
| 6,196,980 B1 | 3/2001 | Akerfeldt et al. |
| 6,201,983 B1 | 3/2001 | Naumann et al. |
| 6,226,451 B1 | 5/2001 | Wong |
| 6,349,722 B1 | 2/2002 | Gradon et al. |
| 6,360,741 B2 | 3/2002 | Truschel |
| 6,402,207 B1 | 6/2002 | Segal et al. |
| 6,435,180 B1 | 8/2002 | Hewson et al. |
| 6,467,477 B1 | 10/2002 | Frank et al. |
| 6,508,249 B2 | 1/2003 | Hoenig |
| 6,511,075 B1 | 1/2003 | Schmidt |
| 6,551,143 B2 | 4/2003 | Tanaka et al. |
| 6,554,260 B1 | 4/2003 | Lipscombe et al. |
| 6,591,061 B2 | 7/2003 | Wang |
| 6,598,604 B1 | 7/2003 | Seakins |
| 6,612,624 B1 | 9/2003 | Segal et al. |
| 6,631,718 B1 | 10/2003 | Lovell |
| 6,648,669 B1 | 11/2003 | Kim et al. |
| 6,668,828 B1 | 12/2003 | Figley et al. |
| 6,685,491 B2 | 2/2004 | Gergek |
| 6,827,084 B2 | 12/2004 | Grubb, Jr. |
| 6,874,771 B2 | 4/2005 | Birdsell et al. |
| 6,895,803 B2 | 5/2005 | Seakins et al. |
| 6,918,389 B2 | 7/2005 | Seakins et al. |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardelius et al. |

(56) References Cited

U.S. PATENT DOCUMENTS

| | | |
|---|---|---|
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,327,547 B1 | 2/2008 | Epstein |
| 7,327,949 B1 | 2/2008 | Cheng et al. |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,478,635 B2 | 1/2009 | Wixey et al. |
| 7,525,663 B2 | 4/2009 | Kwok et al. |
| 7,637,288 B2 | 12/2009 | Kressierer/Huber et al. |
| 7,677,246 B2 | 3/2010 | Kepler et al. |
| 7,743,767 B2 | 6/2010 | Ging et al. |
| 7,766,050 B2 | 8/2010 | Patel |
| 7,794,426 B2 | 9/2010 | Briones et al. |
| 7,814,907 B2 | 10/2010 | Bremner et al. |
| D628,288 S | 11/2010 | Row et al. |
| 7,827,981 B2 | 11/2010 | Barnford |
| 7,870,857 B2 | 1/2011 | Dhuper et al. |
| 7,874,291 B2 | 1/2011 | Ging et al. |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,221,530 B2 | 7/2012 | Peter et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 | 9/2012 | Meyer et al. |
| 8,267,084 B2 | 9/2012 | Kwok |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,469,025 B2 | 6/2013 | Mayer et al. |
| 8,490,621 B2 | 7/2013 | Radomski et al. |
| 8,496,001 B2 | 7/2013 | Schermeier |
| RE44,453 E | 8/2013 | Virr et al. |
| 8,511,305 B2 | 8/2013 | Liu et al. |
| 8,511,651 B2 | 8/2013 | Fridberg et al. |
| 8,522,782 B2 | 9/2013 | Lewis et al. |
| 8,528,552 B2 | 9/2013 | von Blumenthal |
| 8,544,465 B2 | 10/2013 | Smith et al. |
| 8,550,072 B2 | 10/2013 | Thudor et al. |
| 8,631,789 B2 | 1/2014 | Virr et al. |
| 8,640,696 B2 | 2/2014 | Pujol et al. |
| 8,733,348 B2 | 5/2014 | Korneff et al. |
| 8,733,349 B2 | 5/2014 | Bath et al. |
| 8,783,252 B2 | 7/2014 | Pierro et al. |
| 8,800,970 B2 | 8/2014 | Heine et al. |
| 8,844,521 B2 | 9/2014 | McCarthy |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henry et al. |
| 8,985,105 B2 | 3/2015 | Burton et al. |
| 9,022,946 B2 | 5/2015 | Haque |
| 9,067,036 B2 | 6/2015 | Korneff et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,446,210 B2 | 9/2016 | Orr et al. |
| 9,517,321 B2 | 12/2016 | Buechi et al. |
| 9,545,493 B2 | 1/2017 | Mayer et al. |
| 9,566,409 B2 | 2/2017 | Gründler et al. |
| 9,572,949 B2 | 2/2017 | Vos et al. |
| 9,572,951 B2 | 2/2017 | Barker et al. |
| 9,586,019 B2 | 3/2017 | Heine et al. |
| 9,642,979 B2 | 5/2017 | Korneff et al. |
| 9,838,759 B2 | 12/2017 | Kirmse et al. |
| 9,861,778 B2 | 1/2018 | Roderick et al. |
| 9,937,314 B2 | 4/2018 | Buechi et al. |
| 9,937,316 B2 | 4/2018 | Buechi et al. |
| 10,046,136 B2 | 8/2018 | Pujol |
| 2001/0017134 A1 | 8/2001 | Bahr |
| 2001/0050080 A1 | 12/2001 | Seakins et al. |
| 2002/0100320 A1 | 8/2002 | Smith et al. |
| 2003/0066526 A1 | 4/2003 | Thudor et al. |
| 2003/0148664 A1 | 8/2003 | Cheng |
| 2003/0200727 A1 | 10/2003 | Kim |
| 2003/0236015 A1 | 12/2003 | Edirisuriya et al. |
| 2004/0055597 A1 | 3/2004 | Virr |
| 2004/0074493 A1 | 4/2004 | Seakins et al. |
| 2004/0087213 A1 | 5/2004 | Kao |
| 2004/0149284 A1 | 8/2004 | Smith et al. |
| 2004/0221843 A1 | 11/2004 | Baecke |
| 2004/0239001 A1 | 12/2004 | Edirisuriya et al. |
| 2004/0244858 A1 | 12/2004 | Jeong |
| 2006/0030191 A1 | 2/2006 | Tuin et al. |
| 2006/0118113 A1 | 6/2006 | Bremner et al. |
| 2006/0137445 A1 | 6/2006 | Smith et al. |
| 2006/0237012 A1 | 10/2006 | Thudor et al. |
| 2007/0039374 A1 | 2/2007 | Borali |
| 2007/0079982 A1 | 4/2007 | Laurent et al. |
| 2007/0107737 A1 | 5/2007 | Landis et al. |
| 2007/0144519 A1 | 6/2007 | Henry et al. |
| 2007/0169776 A1 | 7/2007 | Kepler |
| 2007/0175473 A1 | 8/2007 | Lewis et al. |
| 2007/0248934 A1 | 10/2007 | Mosimann |
| 2007/0284361 A1 | 12/2007 | Nadjafizadeh et al. |
| 2008/0000474 A1 | 1/2008 | Jochle et al. |
| 2008/0015257 A1 | 1/2008 | Grosskreutz et al. |
| 2008/0051674 A1 | 2/2008 | Davenport et al. |
| 2008/0066751 A1 | 3/2008 | Polacsek |
| 2008/0105257 A1 | 5/2008 | Klasek et al. |
| 2008/0142019 A1 | 6/2008 | Lewis et al. |
| 2008/0202512 A1 | 8/2008 | Kressierer/ Huber |
| 2008/0251073 A1 | 10/2008 | Jassell et al. |
| 2009/0044808 A1 | 2/2009 | Guney et al. |
| 2009/0050150 A1 | 2/2009 | Rossen et al. |
| 2009/0056712 A1 | 3/2009 | Cortez |

(56) References Cited

U.S. PATENT DOCUMENTS

| | | |
|---|---|---|
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0223514 A1 | 9/2009 | Smith et al. |
| 2009/0301482 A1 | 12/2009 | Burton et al. |
| 2009/0320840 A1 | 12/2009 | Klasek et al. |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0242963 A1 | 9/2010 | Brieger et al. |
| 2011/0017212 A1 | 1/2011 | Kenyon |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0156289 A1* | 6/2011 | Steg ............. A61M 16/16 261/70 |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0073573 A1 | 3/2012 | Thudor |
| 2012/0125333 A1 | 5/2012 | Bedford et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0255758 A1 | 10/2012 | Lee |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112202 A1 | 5/2013 | Fogelbrink |
| 2013/0174839 A1 | 7/2013 | Ging et al. |
| 2013/0206140 A1 | 8/2013 | Kepler et al. |
| 2013/0239966 A1 | 9/2013 | Klasek et al. |
| 2013/0247905 A1 | 9/2013 | Miller et al. |
| 2013/0255677 A1 | 10/2013 | Varga |
| 2013/0333701 A1 | 12/2013 | Herron |
| 2013/0340752 A1 | 12/2013 | Landis et al. |
| 2014/0020684 A1 | 1/2014 | Klasek et al. |
| 2014/0090649 A1 | 4/2014 | Groll et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0202463 A1 | 7/2014 | Ging et al. |
| 2014/0216446 A1 | 8/2014 | Wruck |
| 2014/0251322 A1 | 9/2014 | Miller |
| 2014/0251331 A1 | 9/2014 | Korneff et al. |
| 2014/0311489 A1 | 10/2014 | Heine et al. |
| 2014/0318536 A1 | 10/2014 | Landis et al. |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0096560 A1 | 4/2015 | Klenner et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015927 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0095635 A1 | 4/2017 | Huby |
| 2017/0136198 A1 | 5/2017 | Delangre et al. |
| 2017/0161461 A1 | 6/2017 | Delangre et al. |
| 2017/0173293 A1 | 6/2017 | Osborne et al. |
| 2017/0239432 A1 | 8/2017 | Delangre et al. |
| 2017/0326320 A1 | 11/2017 | Baigent et al. |
| 2018/0078730 A1 | 3/2018 | Bath et al. |
| 2018/0169361 A1 | 6/2018 | Dennis et al. |
| 2018/0250491 A1 | 9/2018 | Row et al. |

FOREIGN PATENT DOCUMENTS

| | | |
|---|---|---|
| AU | 2007317198 | 5/2008 |
| AU | 2010206053 | 2/2011 |
| CA | 2495451 | 3/2004 |
| CN | 1598510 | 3/2005 |
| DE | 3110903 | 9/1982 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 102004030747 | 1/2006 |
| DE | 20 2005 008 152.3 | 10/2006 |
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2004 021 759.7 | 10/2007 |
| DE | 20 2006 011 754.7 | 12/2007 |
| DE | 201 22 844.0 | 5/2008 |
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021 829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021 876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |

(56) References Cited

FOREIGN PATENT DOCUMENTS

| | | |
|---|---|---|
| EP | 0201985 | 11/1986 |
| EP | 0291921 | 11/1988 |
| EP | 0535952 | 4/1993 |
| EP | 0567158 | 10/1993 |
| EP | 0885623 | 12/1998 |
| EP | 1262208 | 12/2002 |
| EP | 1352670 | 10/2003 |
| EP | 1646910 | 4/2006 |
| EP | 1669098 | 6/2006 |
| EP | 1683066 | 7/2006 |
| EP | 1741462 | 1/2007 |
| EP | 1924311 | 5/2008 |
| EP | 2079505 | 7/2009 |
| EP | 2089086 | 8/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2415445 | 2/2012 |
| EP | 2471568 | 7/2012 |
| EP | 2498854 | 9/2012 |
| EP | 2514478 | 10/2012 |
| EP | 2575944 | 4/2013 |
| EP | 2640451 | 9/2013 |
| EP | 2651481 | 10/2013 |
| EP | 2654869 | 10/2013 |
| EP | 2667919 | 12/2013 |
| EP | 2760516 | 8/2014 |
| EP | 2830695 | 2/2015 |
| EP | 2877224 | 6/2015 |
| EP | 3013402 | 5/2016 |
| EP | 3053623 | 8/2016 |
| GB | 1310949 | 3/1973 |
| GB | 1364127 | 8/1974 |
| GB | 2176313 | 12/1986 |
| GB | 2 205 504 | 12/1988 |
| JP | H0623051 | 2/1994 |
| JP | 2001095920 | 4/2001 |
| JP | 03194747 | 7/2003 |
| JP | 2003275312 | 9/2003 |
| JP | 4242816 | 3/2009 |
| JP | 11248076 | 12/2011 |
| NZ | 564886 | 2/2011 |
| NZ | 586325 | 1/2012 |
| NZ | 597020 | 6/2013 |
| NZ | 604137 | 6/2014 |
| NZ | 625605 | 4/2016 |
| NZ | 710078 | 1/2017 |
| NZ | 710351 | 1/2017 |
| NZ | 631008 | 7/2017 |
| NZ | 733931 | 2/2019 |
| WO | WO 97/18001 | 5/1997 |
| WO | WO 2000/029057 | 5/2000 |
| WO | WO 2001/032069 | 5/2001 |
| WO | WO 01/97894 | 12/2001 |
| WO | WO 02/066106 | 8/2002 |
| WO | WO 02/066107 | 8/2002 |
| WO | WO 2004/011072 | 2/2004 |
| WO | WO 2005/011785 | 2/2005 |
| WO | WO 2005/021076 | 3/2005 |
| WO | WO 2006/017350 | 2/2006 |
| WO | WO 2007/051230 | 5/2007 |
| WO | WO 2008/055308 | 5/2008 |
| WO | WO 2008/058328 | 5/2008 |
| WO | WO 2008/060295 | 5/2008 |
| WO | WO 2008/076230 | 6/2008 |
| WO | WO 2009/002004 | 12/2008 |
| WO | WO 2009/022004 | 2/2009 |
| WO | WO 2010/031125 | 3/2010 |
| WO | WO 2010/031126 | 3/2010 |
| WO | WO 2012/065999 | 5/2012 |
| WO | WO 2012/154883 | 11/2012 |
| WO | WO 2012/164407 | 12/2012 |
| WO | WO 2013/026901 | 2/2013 |
| WO | WO 2013/045575 | 4/2013 |
| WO | WO 2013/049660 | 4/2013 |
| WO | WO 2013/050907 | 4/2013 |
| WO | WO 2013/127474 | 9/2013 |
| WO | WO 2013/162386 | 10/2013 |
| WO | WO 2014/055407 | 4/2014 |
| WO | WO 2014/077706 | 5/2014 |
| WO | WO 2014/205513 | 12/2014 |
| WO | WO 2015/060729 | 4/2015 |
| WO | WO 2015/160268 | 10/2015 |
| WO | WO 2016/042522 | 3/2016 |
| WO | WO 2016/089224 | 6/2016 |
| WO | WO 2016/139645 | 6/2016 |
| WO | WO 2017/027906 | 2/2017 |
| WO | WO 2017/126980 | 7/2017 |

OTHER PUBLICATIONS

Jun. 24, 2013 International Search Report of Application No. PCT/NZ2013/000075 filed Apr. 26, 2013.

Sawyer, Dick, et al. "An introduction to human factors in medical devices." *US Department of Health and Human Services, Public Health Service, Food and Drug Administration, Center for Devices and Radiological Health* (1996).

\* cited by examiner

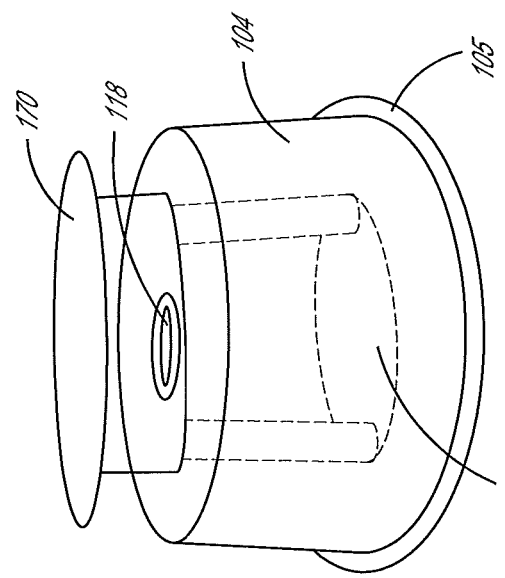
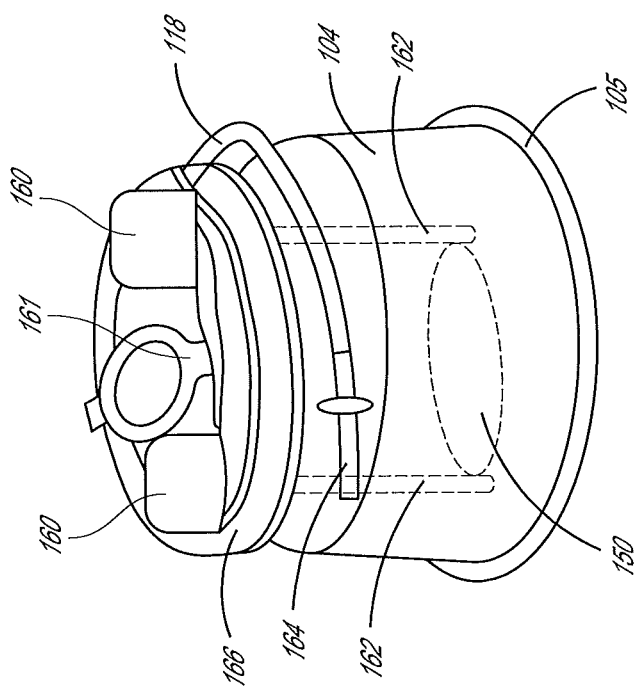
FIG. 4A
FIG. 4B

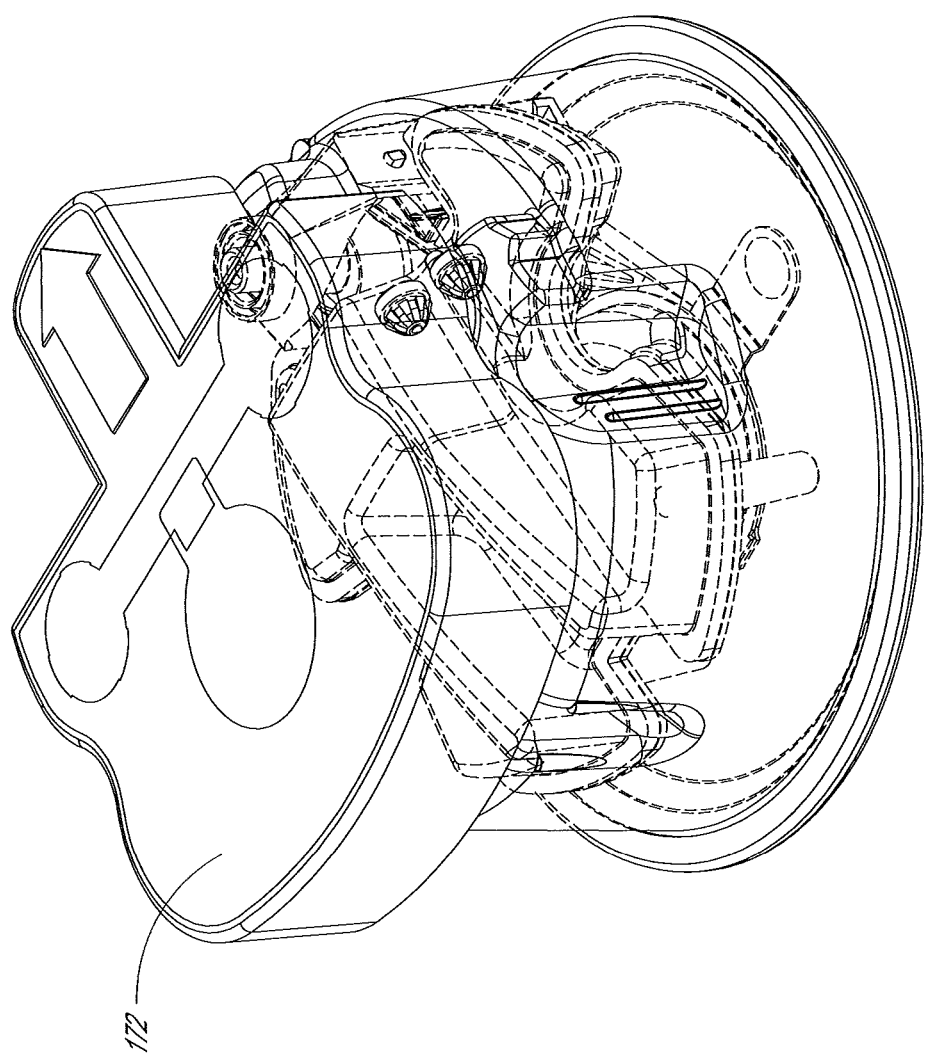

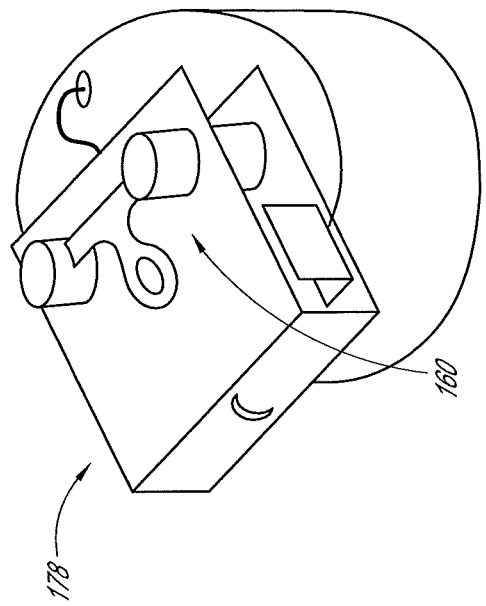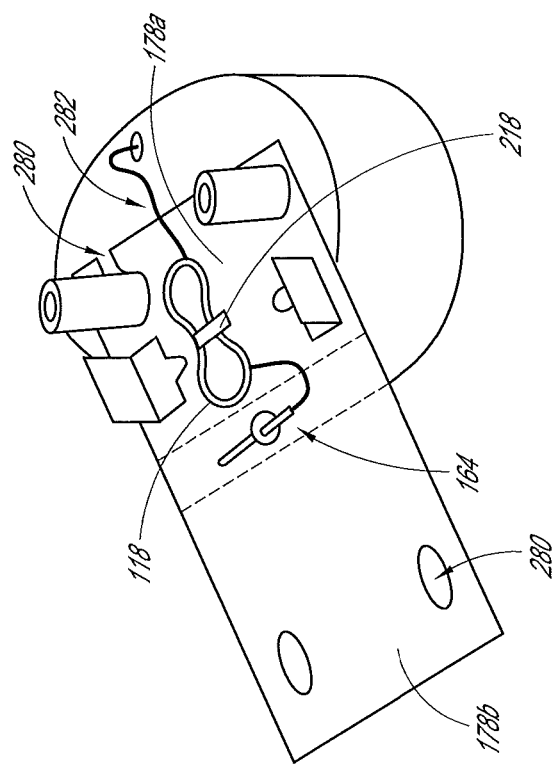
FIG. 4G

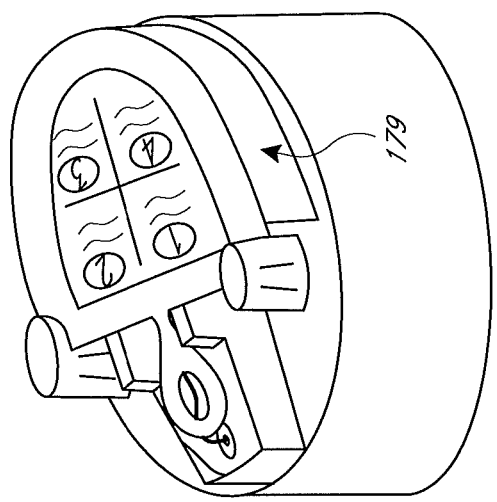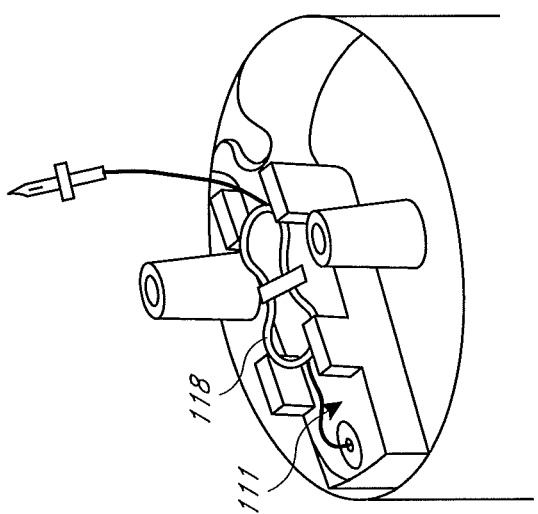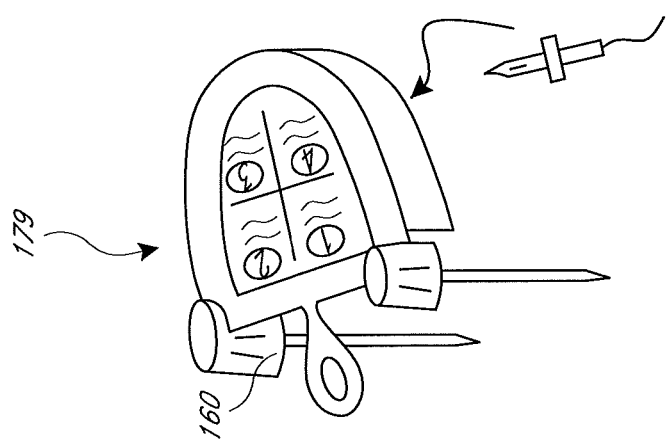
FIG. 4H

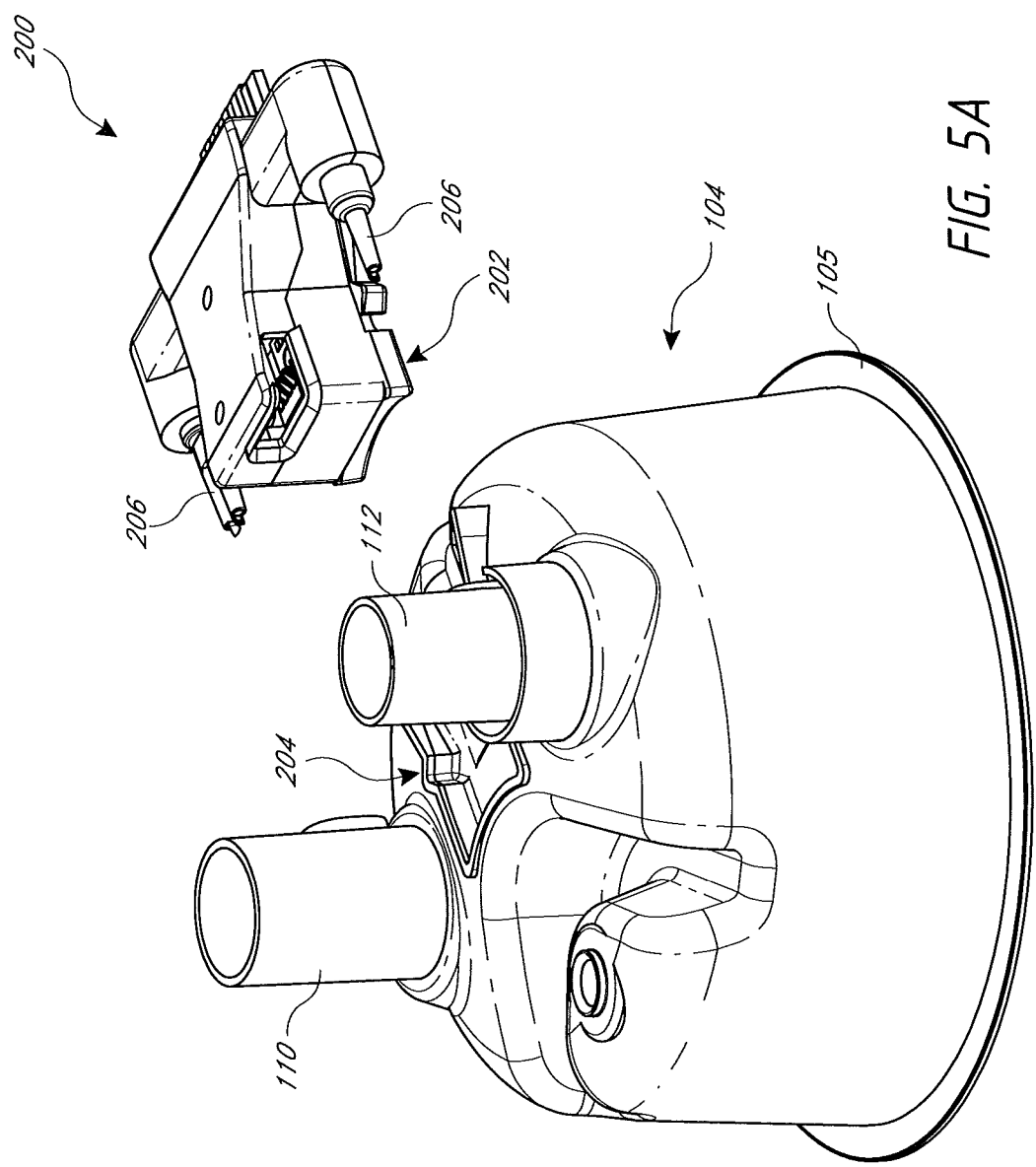

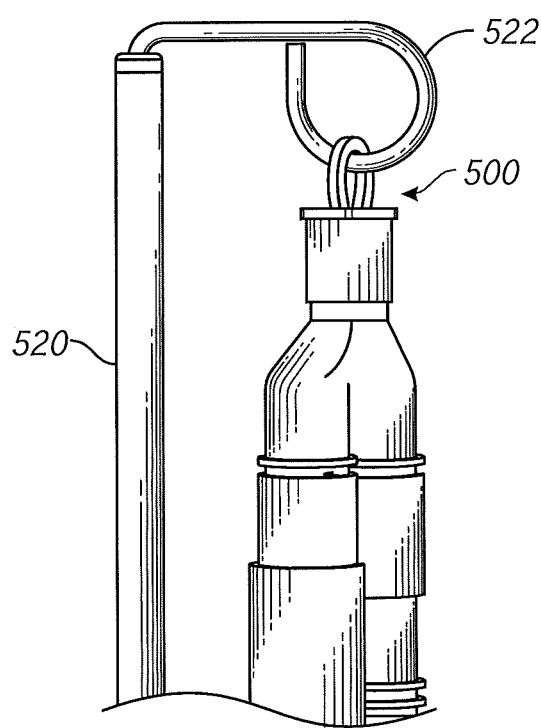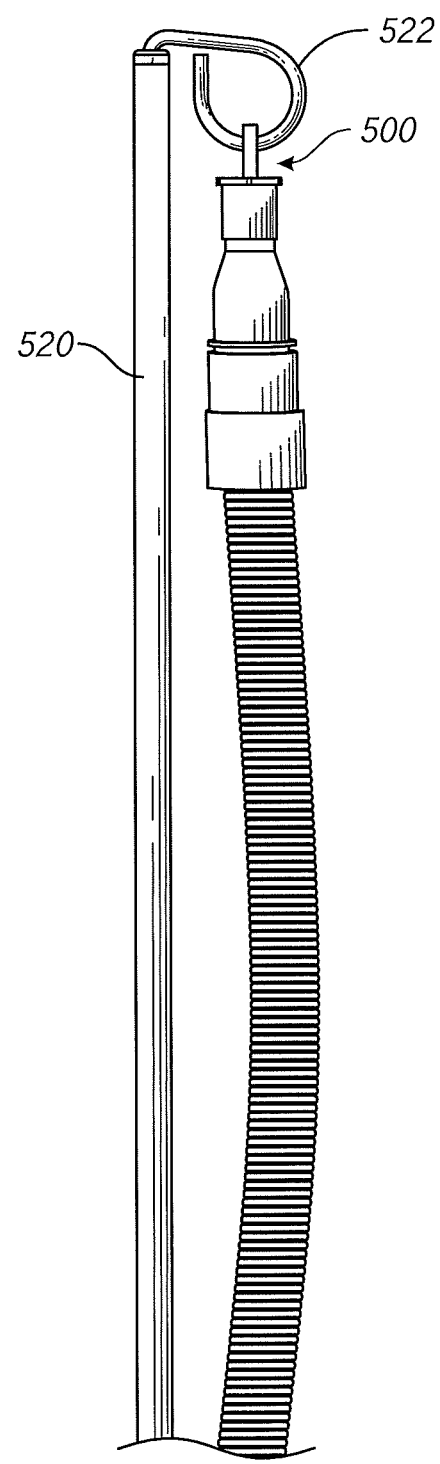
FIG. 18
FIG. 19

USABILITY FEATURES FOR RESPIRATORY HUMIDIFICATION SYSTEM

CROSS-REFERENCE TO RELATED APPLICATIONS

This application claims priority benefit of U.S. Provisional Application No. 61/992,442, filed May 13, 2014, U.S. Provisional Application No. 62/032,208, filed Aug. 1, 2014, and U.S. Provisional Application No. 62/127,443, filed Mar. 3, 2015, each of which is hereby incorporated by reference herein. The following provisional applications are hereby incorporated by reference in their entirety: U.S. Provisional Application No. 61/919,485, filed Dec. 20, 2013; U.S. Provisional Application No. 61/893,758, filed Oct. 21, 2013; U.S. Provisional Application No. 61/877,566, filed Sep. 13, 2013; U.S. Provisional Application No. 61/877,784, filed Sep. 13, 2013; U.S. Provisional Application No. 62/024,969, filed Jul. 15, 2014; and U.S. Provisional Application No. 62/032,462, filed Aug. 1, 2014.

BACKGROUND

Field of the Disclosure

The present disclosure generally relates to humidification systems for humidifying gases supplied to users, and more particularly, to humidification systems having features for improved assembly and usability.

Description of the Related Art

Many gas humidification systems deliver heated and humidified gases for various medical procedures, including respiratory treatment, laparoscopy, and the like. These systems can be configured to control temperature, humidity, and flow rates through the use of various sensors.

Various components of such systems also can include features designed to help control the system and/or help provide users with gases having desired characteristics. Such gas humidification systems can include many components that must be assembled prior to use. The set-up process can be complicated and time-consuming, and may require specialized training. The specialized training may need to be repeated for each new employee or user. Thus, there is a need for a system that is intuitive to assemble and use without extensive training.

Circuits for use in medical systems often comprise a cap to aid with storage and to protect against ingress of dust or contaminants. However, prior art caps comprise materials that may cause damage to an internal surface of the circuit. Caps can fall off in storage or leak. Caps can be challenging for a user to insert and to remove, requiring high forces to insert and/or remove.

Caps often remain connected with the circuit as a user sets up the medical system. For example, in a respiratory system, the cap remains connected with the circuit until the patient interface is connected to the circuit. A user may activate a gases source while the cap remains in place on the circuit. As a result, pressure building up in the circuit can cause the cap to fail. Failure is measured, for example, by the cap coming off the circuit, or by damage to circuit components caused by pressure increases.

Circuits are often bulky and difficult to manipulate in use. A user setting up the system in advance may attempt to drape the circuit across other components in the system in an effort to keep the circuit from being contaminated, for example, by touching the floor. The circuit can be prone to falling to the floor and becoming contaminated.

SUMMARY

A humidification system for delivering humidified gases to a user can comprise a heater base, a humidification chamber having an inlet, outlet, and associated liquid conduit, and a breathing circuit including a supply conduit, inspiratory conduit, and optional expiratory conduit. A humidification system can comprise various features as described herein to help make set-up less difficult and time-consuming. Such features can also help make the set-up process more intuitive for an operator, which can reduce the need for specialized training and reduce the number of potential errors.

According to some aspects of the present disclosure, a humidification apparatus comprises a humidification chamber configured to hold a volume of liquid. The humidification chamber comprises at least one side wall, a top wall connected to the at least one side wall, a cavity at least partially defined by the at least one side wall and the top wall, an inlet port defining a passage into the cavity of the humidification chamber, an outlet port defining a passage out of the cavity of the humidification chamber and having an elbow configuration, wherein the outlet port is uncovered for shipping and/or storage, and a port cap configured to cover the inlet port for shipping and/or storage, the port cap comprising a leg that extends into the inlet port.

The inlet port can comprise a baffle extending at least partially below the inlet port and configured to inhibit splashing through the inlet port, wherein the leg of the port cap is configured to extend below the baffle. The leg of the port cap can be configured to secure one or more floats within the humidification chamber for shipping and/or storage. The chamber can further comprise a liquid inlet in fluid communication with the cavity and a liquid conduit having a first end coupled to the liquid inlet and a second end coupled to a spike configured to be connected to a liquid source, wherein the spike is positioned under the port cap for shipping and/or storage. The liquid conduit can be looped and inserted under the port cap during assembly for shipping and/or storage. The chamber can further comprise a liquid inlet in fluid communication with the cavity and a liquid conduit having a first end coupled to the liquid inlet and a second end coupled to a spike configured to be connected to a liquid source, wherein the spike is stored in a sheath attached to the port cap for shipping and/or storage.

The chamber can further comprise a handle coupled to the chamber, a shelf extending between a portion of the handle and a portion of the at least one side wall of the chamber, a liquid inlet in fluid communication with the cavity, and a liquid conduit having a first end coupled to the liquid inlet and a second end coupled to a spike configured to be connected to a liquid source, wherein the spike is stored on the shelf for shipping and/or storage. The liquid conduit can be stored on the shelf for shipping and/or storage. The port cap can comprise a ring configured to be grasped for removal of the port cap and to be attached to a medical stand. The humidification apparatus can further comprise an inspiratory conduit having a first end coupled to the outlet port for shipping and/or storage. The port cap can comprise a contact surface, and a heater base configured to support the humidification chamber can comprise a lifting surface, so that when the humidification chamber is inserted onto the heater base with the port cap covering the inlet port, the lifting surface contacts the contact surface and causes the port cap to lift away from the inlet port. The lifting surface can be on a sensor cartridge module coupled to the heater base.

According to some aspects of the present disclosure, a circuit end cap comprises a body configured to be inserted into an end of a breathing circuit component, a flange at a first end of the body, wherein a diameter of the flange is larger than a diameter of the body and a lower surface of the flange configured to face the body is configured to seal against the end of the breathing circuit component, and a pull ring extending from the body and configured to be used to aid removal of the circuit end cap from the breathing circuit component and/or to hang the breathing circuit component from a medical stand or hook.

The body can comprise frustoconical tapers configured to form a sealing interface with an interior of the breathing circuit component. The body can comprise three frustoconical tapers such that the frustoconical tapers provide a sufficient friction fit with the breathing circuit component while allowing the circuit end cap to be removed from the breathing circuit component without excessive force. The pull ring can extend from a top surface of the flange along a longitudinal axis of the body. Alternatively, the pull ring can extend from a side of the flange perpendicularly to a longitudinal axis of the body. A diameter of the flange can be selected for use with various breathing circuit components. The diameter of the body and frustoconical tapers can be selected for use with various breathing circuit components. The body can comprise a plurality of channels, each channel extending parallel to a longitudinal axis of the body on an outside surface of the body, wherein the channels allow gases to vent from the breathing circuit component. The plurality of channels can extend into the lower surface of the flange. The body can comprises a plurality of channels extending parallel to a longitudinal axis of the body on an outside surface of the body, wherein the channels separate the frustoconical tapers into a plurality of segments.

According to some aspects of the present disclosure, a humidification chamber is packaged with the inlet port and the outlet port covered by a port cap. The port cap can be designed to help indicate to the operator that the port cap should be removed and discarded during set-up. A liquid conduit, or feedset, can be contained and concealed by the port cap so that the feedset cannot be connected to a liquid source until the port cap is removed. The port cap can be designed to cover only the inlet port or only the outlet port.

According to some aspects of the present disclosure, a supply conduit, an inspiratory conduit, and an optional expiratory conduit are coupled into a one-piece assembly to aid set-up. The conduits can be coupled by, for example, a mesh sheath, clips, or any other appropriate coupling mechanism. One or more of the conduits can be removably coupled to the others. The expiratory conduit can include an electrical plug configured to be connected to a socket on the heater base to power a heating element within the conduit. One or more of the conduits can include integrated sensors and adaptor cables to connect the sensors to the heater base.

According to some aspects of the present disclosure, various components of a humidification system are color-coded and can have corresponding structures to indicate which components should be connected to one another during set-up. The heater base and/or consumables packaging can also include a schematic or step-by-step instructions to help guide the operator through the set-up procedure.

According to some aspects of the present disclosure, a humidification apparatus comprises a heater base and a humidification chamber. The heater base comprises a heater and a display, the heater plate being configured to support a humidification chamber and the display oriented at an angle of about 22° from vertical. The humidification chamber can be configured to hold a volume of liquid and can comprise at least one side wall, a top wall connected to the at least one side wall, a base surface connected to the at least one side wall, a cavity being at least partially defined by the at least one side wall and the top wall, at least one of the at least one side wall and the top wall of the humidification chamber having features that define a front of the humidification chamber and a back of the humidification chamber, a liquid inlet in fluid communication with the cavity, the liquid inlet positioned closer to the front of the humidification chamber than the back of the humidification chamber, an inlet port defining a passage into the cavity of the humidification chamber, an outlet port defining a passage out of the cavity of the humidification chamber, wherein the outlet port has an elbow shape, and a liquid conduit having a first end coupled to the liquid inlet and a second end configured to be connected to a liquid source. The liquid conduit can comprise a first end coupled to the liquid inlet and a second end coupled to a spike configured to be connected to a liquid source.

According to some aspects of the present disclosure, a humidification apparatus comprises a heater base, a humidification chamber, and a liquid conduit. The heater base comprises first and second sensors and a heater plate, the first and second sensors being positioned vertically higher than the heater plate, the heater plate being configured to support a humidification chamber. The humidification chamber can be configured to hold a volume of liquid and can comprise at least one side wall, a top wall connected to the at least one side wall, a cavity being at least partially defined by the at least one side wall and the top wall, a liquid inlet in fluid communication with the cavity, an inlet port extending through the top wall and defining a passage into the cavity, the inlet port having an aperture configured to receive the first sensor, an outlet port extending through the top wall and defining a passage out of the cavity, the outlet port having an aperture configured to receive the second sensor, and interlock features in the top wall configured to receive corresponding interlock features on the heater base to guide insertion of the chamber on the heater base so that the first and second sensors are received in the apertures of the inlet and outlet ports. The first and second sensors can be integrated into a sensor cartridge module that is mechanically and electrically connected to the heater base.

The humidification apparatus can further comprise a supply conduit and an inspiratory conduit, wherein a first end of the supply conduit comprises a chamber end connector configured to be coupled to the inlet port, a second end of the supply conduit is configured to be coupled to a gases supply, at least part of the inlet port comprises a first indicator, at least part of the supply conduit chamber end connector comprises the first indicator, a first end of the inspiratory conduit comprises a chamber end connector configured to be coupled to the outlet port, at least part of the outlet port comprises a second indicator, and at least part of the inspiratory conduit chamber end connector comprises the second indicator. The first indicator can comprise a first color, and the second indicator can comprise a second color.

The interlock features in the top wall can comprise a recess and the interlock features on the heater base can comprise a protrusion, the recess configured to receive the protrusion, and the protrusion configured to extend greater than halfway across the chamber when the chamber is fully installed on the heater base. The interlock features in the top wall can further comprise a raised portion and the interlock features on the heater base can further comprise a central channel located on a bottom surface of the protrusion, the raised portion configured to be received in the central channel when the chamber is properly installed on the heater base. The humidification apparatus can further comprise a port cap configured to cover the inlet port for shipping and/or storage, the port cap comprising a leg that extends into the inlet port. The port cap can be configured to cover the spike for shipping and/or storage. The heater base can further comprise a guard along a front portion of a rim edge, the guard configured to be depressed to enable a lower portion of the chamber to slide under the rim edge and the guard configured to revert to a non-depressed position once the chamber is installed on the heater base.

According to some aspects of the present disclosure, a humidification apparatus comprises a humidification chamber configured to hold a volume of liquid and comprising at least one side wall, a top wall connected to the at least one side wall, a base surface connected to the at least one side wall, a cavity at least partially defined by the at least one side wall and the top wall, at least one of the at least one side wall and the top wall of the humidification chamber having features that define a front of the humidification chamber and a back of the humidification chamber, an inlet port defining a passage into the cavity of the humidification chamber, the inlet port having an aperture configured to receive a first sensor mounted on a heater base, and an outlet port defining a passage out of the cavity of the humidification chamber and having an aperture configured to receive a second sensor mounted on the heater base, wherein an axis extending through the aperture of the inlet port is generally parallel to an axis extending through the aperture of the outlet port, the axes extending in a front to back direction of the humidification chamber and the axes extending generally parallel to the base surface of the humidification chamber.

The humidification apparatus can further comprise a heater base configured to receive the humidification chamber. At least one of the at least one side wall and the top wall can comprise interlock features configured to receive corresponding interlock features on the heater base to guide insertion of the chamber on the heater base so that the first and second sensors are received in the apertures of the inlet and outlet ports. The interlock features can comprise recesses in the top wall and the interlock features on the heater base comprise corresponding protrusions, the interlock features of the top wall and the interlock features on the heater base being engaged through movement along the axes of the apertures in the inlet port and the outlet port. In some embodiments, the heater base comprises a sensor cartridge comprising the first and second sensors. The humidification apparatus can further comprise an inspiratory conduit comprising a chamber end connector configured to be coupled to the outlet port and at least one sensor and/or heating element, the chamber end connector comprising an electrical connection configured to couple to a corresponding electrical connection on the sensor cartridge.

The humidification apparatus can comprise a supply conduit, an inspiratory conduit, and an expiratory conduit, wherein a first end of the supply conduit is configured to be coupled to a gases supply, a second end of the supply conduit comprises a chamber end connector configured to be coupled to the inlet port, a first end of the inspiratory conduit comprises a chamber end connector configured to be coupled to the outlet port, a first end of the expiratory conduit is configured to receive gases exhaled by a patient in use, and a second end of the expiratory conduit is configured to be coupled to the gases supply. The supply conduit, the inspiratory conduit, and the expiratory conduit can be coupled to one another to form a one-piece circuit. The supply conduit, the inspiratory conduit, and the expiratory conduit can be coupled with, for example, a mesh wrap, clips, a hook and loop fastener, or a snap fit.

At least part of the chamber end connector of the supply conduit and at least part of the inlet port can comprise a first indicator. The first indicator can comprise a first color. At least part of the chamber end connector of the inspiratory conduit and at least part of the outlet port can comprise a second indicator. The second indicator can comprise a second color. The humidification apparatus can further comprise a Y-piece, wherein a second end of the inspiratory conduit comprises a patient end connector configured to be coupled to a first branch of the Y-piece, the first end of the expiratory conduit comprises a patient end connector configured to be coupled to a second branch of the Y-piece, and at least part of the Y-piece comprises a third indicator. The third indicator can comprise a third color. The supply conduit, the inspiratory conduit, and the expiratory conduit can be held in a looped configuration with a circuit sleeve for shipping and/or storage. The circuit sleeve can be positioned on the conduits to hide selected connectors to help guide sequential connection of the conduits.

The humidification apparatus can comprise a liquid inlet and a liquid conduit having a first end coupled to the liquid inlet and a second end coupled to a spike configured to be connected to a liquid source. The humidification apparatus can further comprise a winder, and the liquid conduit can extend from the liquid inlet, around the winder, and into the winder, and the spike can be seated in the winder for shipping and/or storage. The humidification apparatus can comprise a port cap configured to cover the inlet port and the outlet port for shipping and/or storage. The port cap can comprise legs that extend into the inlet port and the outlet port. The humidification apparatus can comprise a port cap configured to cover the inlet port for shipping and/or storage, the port cap comprising a leg that extends into the inlet port. The humidification apparatus can comprise a port cap configured to cover the outlet port for shipping and/or storage, the port cap comprising a leg that extends into the outlet port. The port cap can be configured to cover the spike for shipping and/or storage.

The humidification apparatus can include grips configured to allow an operator to hold the chamber more easily during installation. The grips can comprise recesses in the side wall of the chamber. The apertures can be positioned in the inlet and outlet ports so that the apertures face rearward and the grips are located in a front half of the chamber to help orient the chamber for installation on the heater base. The heater base can comprise a guard along a front portion of a rim edge, the guard configured to be depressed to enable a lower portion of the chamber to slide under the rim edge and the guard configured to revert to a non-depressed position once the chamber is installed on the heater base.

According to some aspects of the present disclosure, a cap for a medical circuit can comprise a coupling component and a plug connected to the coupling component. The plug may comprise a disc and a body. The disc may have a diameter that is larger than the diameter of the body. This aids in the at least partial sealing of the circuit. For example, the channels and the disc provide a tortuous path for dust or contaminant ingress into the circuit. The body may comprise at least one segment of at least one frustoconical taper to facilitate at least partial sealing between the cap and an end of a medical circuit. The body may further comprise a channel. The channel may be configured to provide a passageway for gases. If a user initiates gases flow in a circuit prior to removing the cap from the circuit, the gases can be released to the atmosphere through the channels. This release of gases reduces the pressure build up within the circuit. The body may comprise a cylindrical structure. The body may comprise a first end that is sealed by the disc and a second end that is branched by at least one rib or a pair of ribs. The ribs may be perpendicular to each other. The ribs may be attached to the disc and to an internal wall of the body. The disc may comprise a lip that extends perpendicularly from a perimeter of the disc. The channel may extend into the lip or into the disc.

The cap can comprise a material that reduces the likelihood of damage to internal surfaces of the end of the circuit. At least a portion of the body of the cap can configured to be at least partially received by a medical circuit. The channel can comprise at least one orifice. The at least one segment of the at least one frustoconical taper can comprise a total area that is at least 73% of the area of the outer surface of the body. The disc can comprise an upper surface that is configured to convey a visual message to a user. The message can be in the form of a drawing, instruction, colour coding, text, or a combination of these. The body can comprise a plurality of channels. The plurality of channels can comprise a total area that is no greater than 27% of the area of the outer surface of the body. The coupling component can be configured to facilitate hanging of the cap on a supporting structure. The coupling component can be configured to facilitate hanging the cap, coupled to a medical circuit, on a supporting structure. The coupling component can be configured to receive a finger. The coupling component can be configured to facilitate removal of the cap from the medical circuit. The coupling component can comprise a ring.

For purposes of summarizing the disclosure and the advantages achieved over the prior art, certain objects and advantages are described herein. It is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

Disclosed herein are embodiments of a port cap for use with a humidification chamber, the port cap comprising a first portion configured to cover an inlet port of the humidification chamber for shipping and/or storage, and a monolithic leg extending from the first portion to a distal end and configured to extend through the inlet port into the humidification chamber, the leg comprising a float contacting structure configured to contact one or more floats in the humidification chamber and restrain the one or more floats for shipping and/or storage, the leg comprising a stepped portion such that the leg transitions from a first width to a second width, wherein the float contacting structure comprises the stepped portion.

BRIEF DESCRIPTION OF THE DRAWINGS

These and other features, aspects and advantages of the present disclosure will be described with reference to the following drawings, which are illustrative but should not be limiting of the present disclosure.

FIGS. 4A-4H illustrate a humidification chamber as packaged.

FIG. 5A illustrates a sensor cartridge and a humidification chamber.

FIGS. 14I-14J illustrate the port cap of FIGS. 14G-14H installed on the chamber of FIGS. 12-13B.

FIGS. 18 and 19 illustrate the end cap of FIGS. 16 and 17 coupled to a circuit component and hanging from a medical stand.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the present disclosure should not be limited by any particular embodiments described below.

Figure 1:
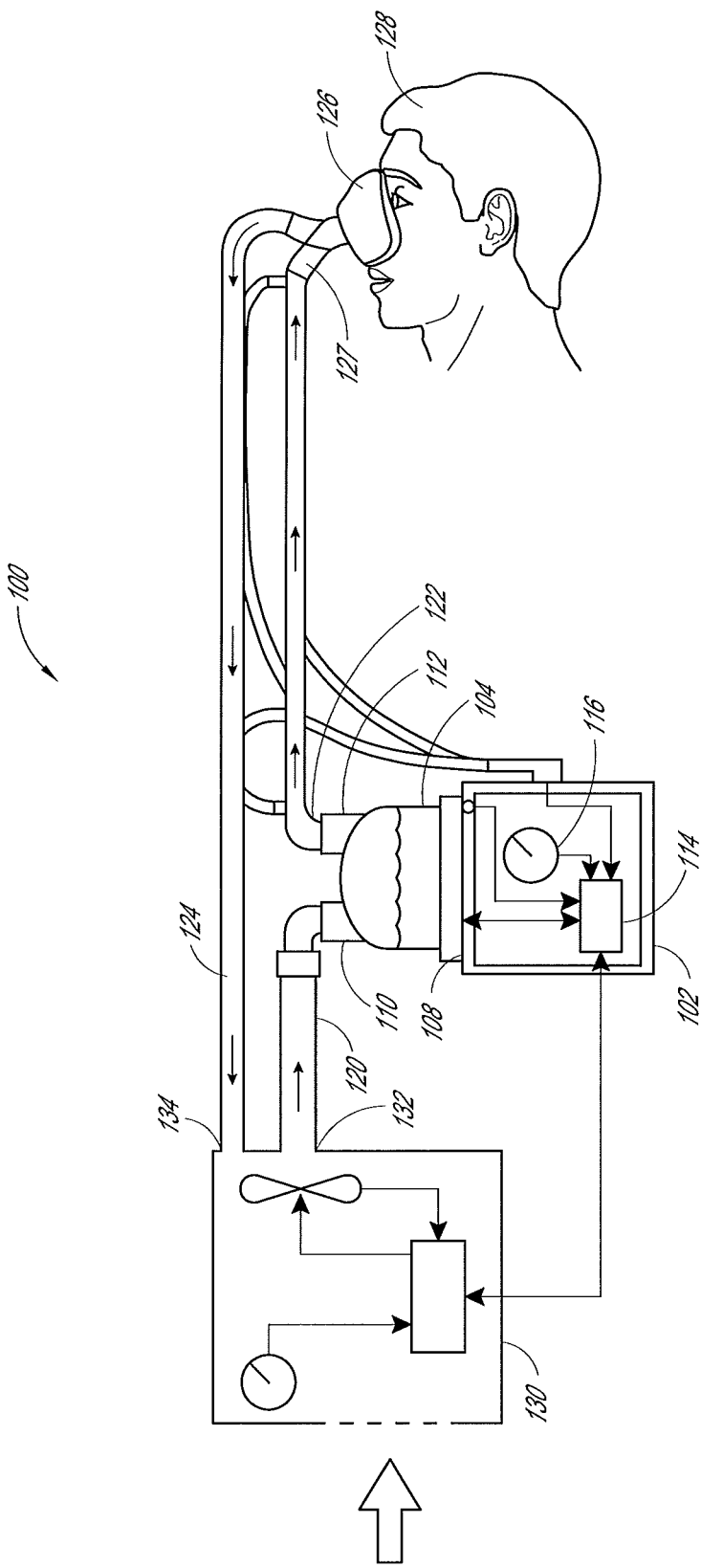
FIG. 1 illustrates a schematic of a humidification system.
Figure 3:
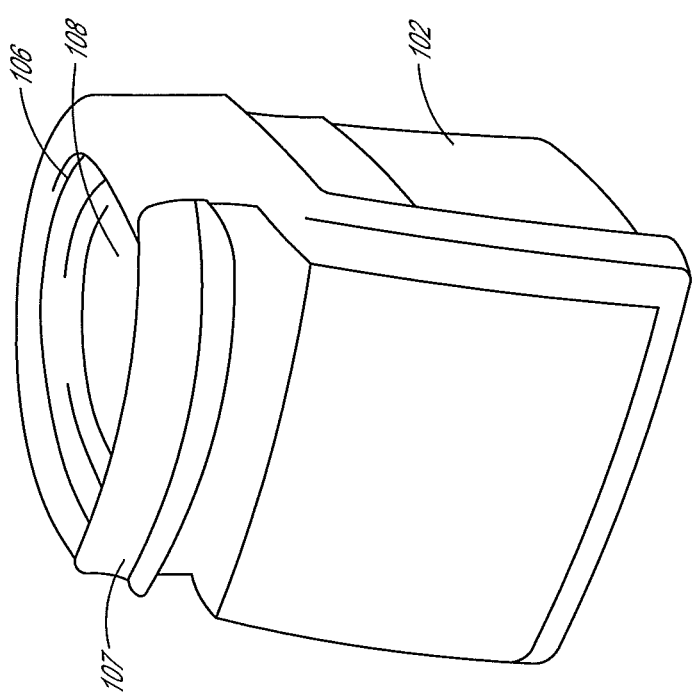
FIG. 3 illustrates a heater base.

An example embodiment of a humidification system 100 can include a heater base 102, a humidification chamber 104, and a breathing circuit or breathing circuit assembly, for example, as shown in FIG. 1. In some embodiments, the system 100 further comprises a gases supply 130, for example, a ventilator or other suitable source of pressurized gases suitable for breathing or use in medical procedures. The heater base 102 can include a heater plate 108 (better shown in FIG. 3). In addition, the heater base 102 can comprise one or more processors 114 and one or more memories or other suitable storage components. In some embodiments, the heater base 102 also comprises a display that can provide information to and/or receive input from an operator.

In some configurations, the display can have a schematic to facilitate the operator making the desired connections, in some instances in a desired order. For example, the display can have a static image with lights (e.g., LED) under different regions that light in a sequence to encourage the desired connection order. In some configurations, the image can be formed on membranes that are back-screen printed behind a polyester or polycarbonate film with LEDs attached to or positioned adjacent to the film. In some configurations, the lights may begin the sequence when a switch is operated by insertion of a humidification chamber into the heater base or the like. Such configurations resolve any need for an operator to turn on the heater base to get the feedback on proper connection sequence. Other suitable arrangements also can be used.

Figure 2A:
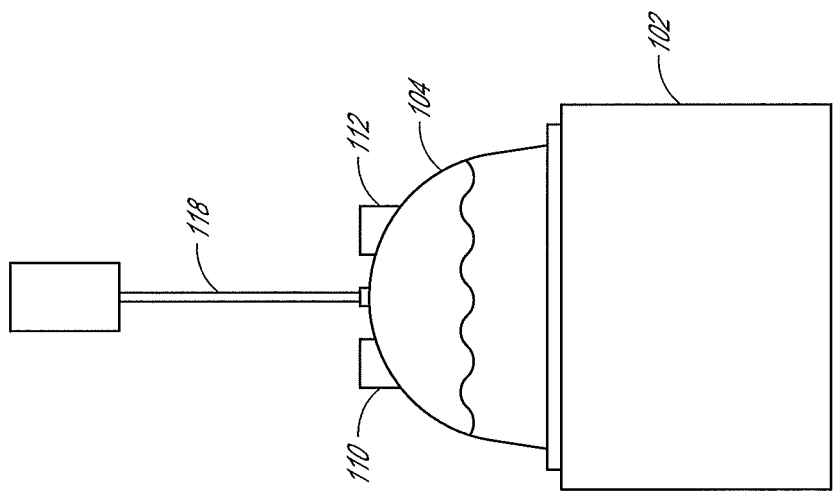
FIG. 2A illustrates a humidification chamber installed on a heater base.

The humidification chamber 104 generally comprises an inlet 110 and an outlet 112 and is configured to be installed on the heater plate 108 of the heater base 102. The humidification chamber 104 is further configured to hold a volume of a liquid, such as water. The chamber 104 can include an opening or port for the connection of a liquid conduit or feedset 118. The liquid conduit 118 can extend from the chamber 104, as shown in FIG. 2A. In some configurations, the liquid conduit 118 can connect to a spike for a water bag. In some configurations, the liquid conduit 118 can be integrally formed with or permanently coupled to the chamber 104. The spike can be coupled to the liquid conduit 118 via an adhesive, sonic welding, an interference fit, or any other suitable means. In some embodiments, the spike includes a vent. If the spike is inserted into, for example, a plastic, collapsible bag, the vent is plugged. However, if the spike is inserted into a rigid container, such as a glass bottle, the vent is open and allows air to enter the container to help reduce or prevent negative pressures in the container. The vent can include a filter that is permeable to gases but impermeable to liquids.

Figure 2B:
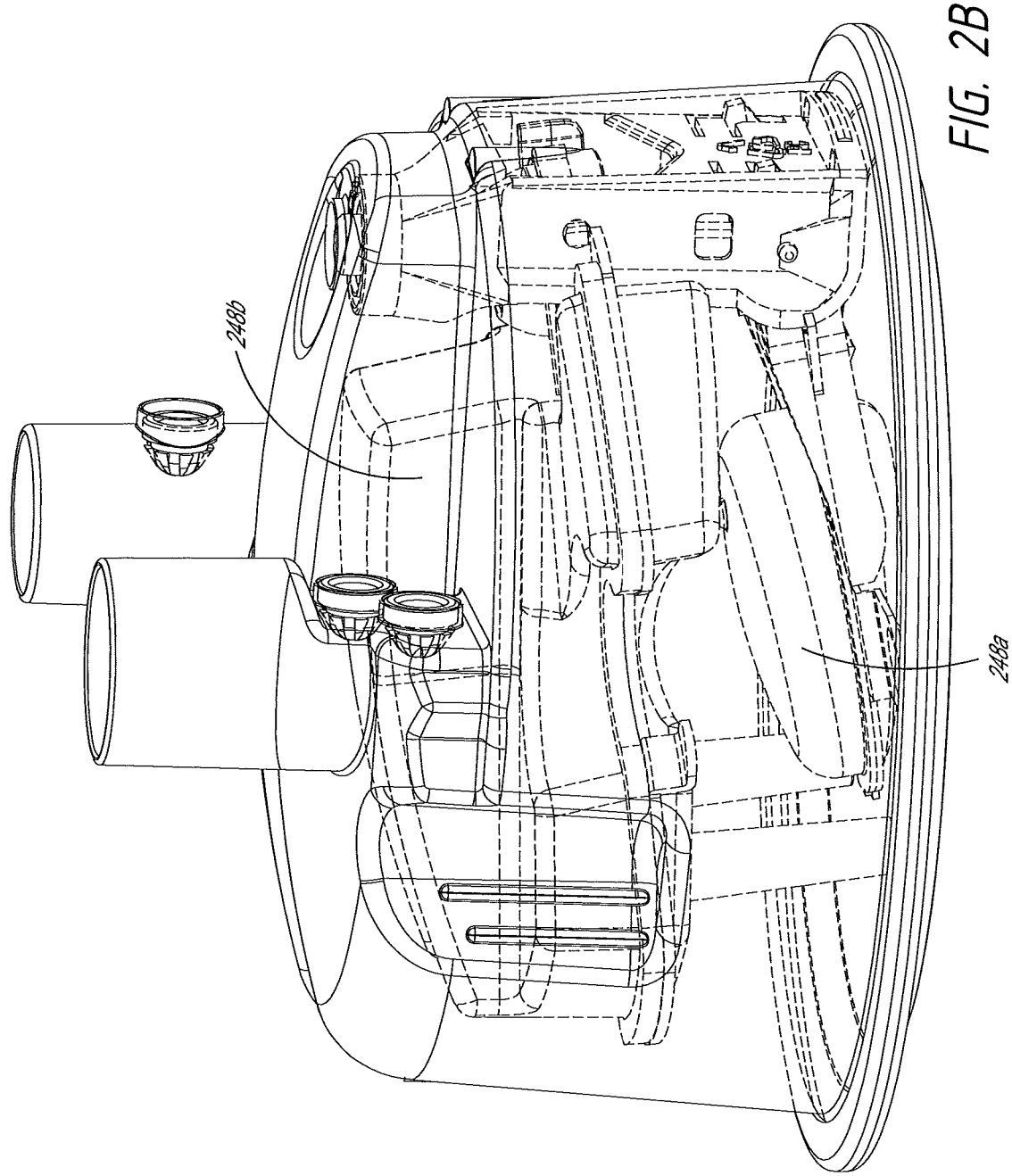
FIG. 2B illustrates a humidification chamber.

In use, the liquid conduit 118 conveys a liquid, for example, water, from a liquid source, such as a water bag, saline bag, or the like, to the chamber 104. The heater plate 108 heats the chamber 104 and causes at least some of the chamber 104 contents to evaporate. In some embodiments, the humidification chamber 104 can include features to help reduce the likelihood of the level of liquid in the chamber 104 from exceeding a particular level. For example, the chamber 104 can include one or more floats 150 as shown in FIGS. 2B, 4A, and 4B. The floats rise and fall with the level of liquid in the chamber 104. When the liquid level reaches a certain level, the floats 150 obstruct or block the port that is connected to the liquid conduit 118 to stop or slow further ingress of liquid into the chamber 104. Other similar features also can be used. In a preferred embodiment, a plurality of floats 150 are used, each float adapted to stop the further ingress of liquid into the chamber 104. To this end, a second float provides a backup or safety mechanism, thereby further reducing the likelihood of the chamber 104 overfilling. FIG. 2B illustrates an example embodiment of such a chamber 104 having a primary float 248a and a secondary float 248b.

With reference again to FIG. 1, the breathing circuit assembly can include a supply conduit 120, an inspiratory conduit 122, and, in some configurations, an expiratory conduit 124. A gases supply end of the supply conduit 120 is configured to connect to an output 132 of the gases supply 130 and a chamber end of the supply conduit 120 is configured to connect to the inlet 110 of the chamber 104. A chamber end of the inspiratory conduit 122 is configured to connect to the outlet 112 of the chamber 104, and a user end of the inspiratory conduit 122 is configured to connect to the user 128 via an interface 126, for example. A user end of the expiratory conduit 124 is configured to connect to the interface 126, and a gases supply end of the expiratory conduit 124 is configured to connect to a return 134 of the gases supply 130. The user ends of the inspiratory conduit 112 and expiratory conduit 124 can be connected to the interface 126 via a Y-piece 127, for example but without limitation.

In use, gases flow from the gases supply 130 through the supply conduit 120 and into the chamber 104 via the inlet 110. The gases are humidified within the chamber 104 and exit the chamber 104 through the outlet 112. The user inhales humidified gases supplied through the inspiratory conduit 122, and exhales into the expiratory conduit 124. The inspiratory conduit 122 and/or expiratory conduit 124 can each include a heating element, for example, a heating wire, to help maintain the gases at a desired temperature and to reduce the likelihood of significant condensation formation in the conduits.

Before use, an operator, such as medical personnel, must correctly connect the various components to set up the system 100. Because of the variety of components and number of connections that must be made, set-up of the system 100 can be a complex process that requires special training to complete properly. The humidification system 100 can include various features as described herein to simplify the set-up process and reduce the likelihood of an incorrect set-up. In some embodiments, certain usability features advantageously can help reduce the total number of steps and time required during the set-up process. Some features described herein also can help make set-up more intuitive for the user, which can reduce the need for specialized in-service training.

To begin set-up, the operator installs the humidification chamber 104 on the heater base 102 by sliding the chamber 104 onto the heater base 102 under a rim edge 106 (shown in FIG. 3) that helps hold the chamber 104 in place. The heater plate 108 can be spring loaded in some configurations such that the base of the chamber 104 presses downward upon the heater plate 108 and a protruding portion 105 of the chamber 104 can be captured between the heater plate 108 and the rim edge 106. Preferably, a guard 107 along a front portion of the rim edge 106 is depressed to enable the lower portion of the chamber 104 to access the heater plate 108 and then the guard 107 reverts to a non-depressed position once the chamber 104 is installed. This advantageously provides positive feedback that the chamber 104 is fully installed on the base 102. In some configurations, the forwardmost portions of the rim edge 106 (e.g., the portions of the rim edge 106 that define an opening for insertion of the chamber 104) are configured with a raised or enlarged opening 109 that ramps downward. The opening 109 preferably comprises a lower surface that is elevated above an upper surface of the non-depressed guard 107. In such a manner, the opening 109 provides a visual clue to the operator that the protruding portion 105 can be inserted into the opening 109. Further insertion of the chamber 104 into the opening 109 causes the guard 107 to be depressed and facilitates full insertion of the chamber into the heater base and can help guide the chamber 104 into place. Thus, these visual details can indicate to the operator that the chamber 104 slides into place under the rim edge 106. This can also help inform the operator that the guard 107 can be depressed to later remove the chamber 104 from the heater base 102. Preferably, the chamber 104 has details to depress the guard 107 when the operator attempts to remove the chamber 104 from the heater base 102. Moreover, by providing an uneven upper surface to the rim edge 106, the operator is less likely to believe that the chamber 104 should be placed atop the rim edge 106, resulting in poor thermal conductivity, because such a placement will lead to an uneven positioning of the chamber 104.

Figure 4C:
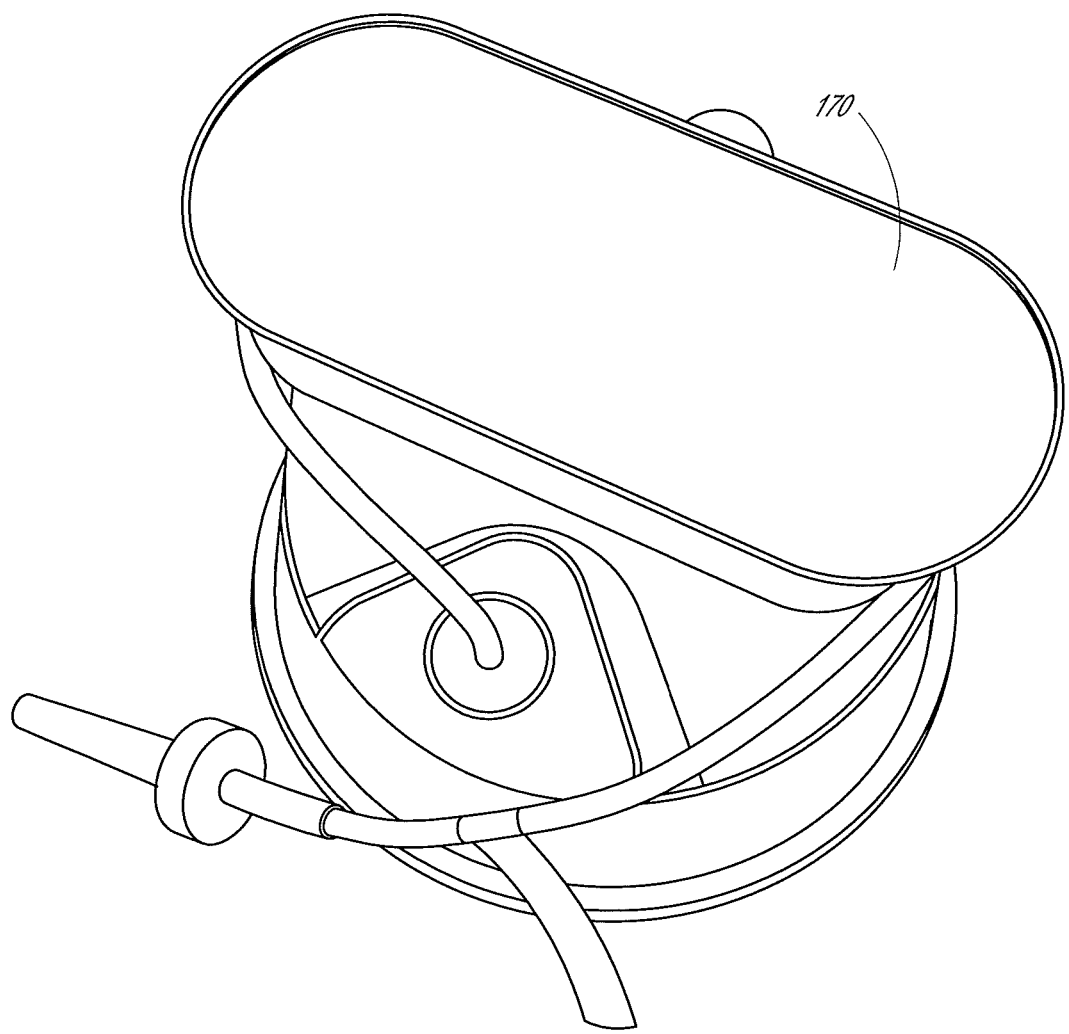
Figure 4D:
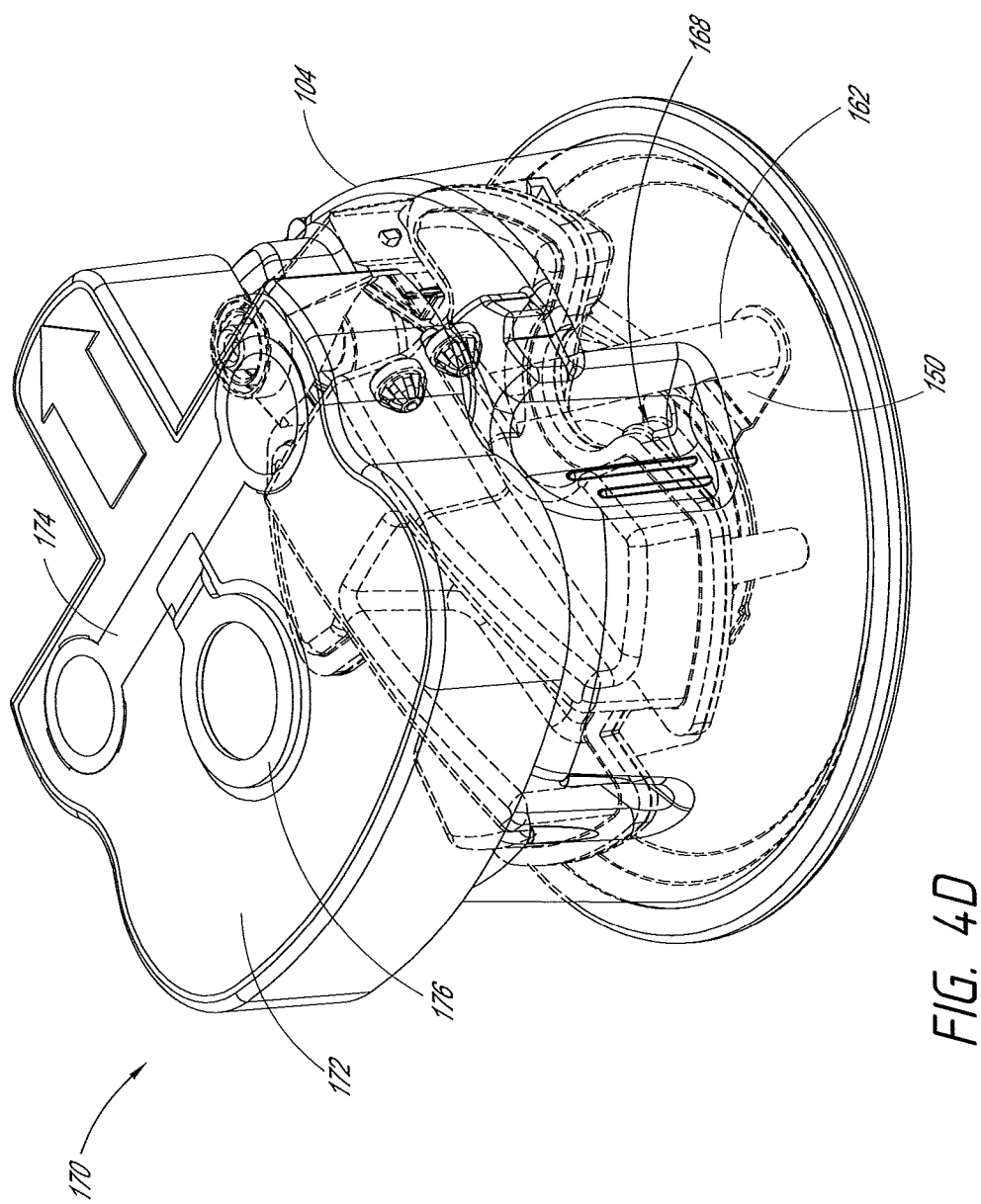

Humidification chambers, such as the chamber 104, often have a generally rounded shape with generally smooth sides, which can make it difficult for the operator to hold the chamber 104 during set-up and installation. In setting up the humidifier, the chamber 104 will be grasped and then slid into position on the heater base 102, as described above. Therefore, as shown in FIG. 4D, the chamber 104 can include grips 168 to advantageously allow the operator to hold the chamber 104 more easily during installation. In some embodiments, for example as illustrated in FIG. 4D, the grips 168 are positioned at particular locations on the chamber 104 to help guide the operator to correctly orient the chamber 104 when sliding the chamber 104 onto the base 102. In some embodiments, the grips 168 extend partially or completely around the chamber 104. The grips 168 can include one or more of, for example, depressions or cavities on the chamber 104 surface, vertical fins, a textured surface, and/or a handle. In the illustrated configuration, a sidewall of the chamber includes recesses that extend inwardly toward the chamber. The recesses can include ribs or the like to enhance the ability of a user to grip the chamber by the recesses. The recesses can be positioned along a forward facing surface. In some configurations, the upwardly extending ports of the humidifier chamber can include openings that face rearward while the recesses are concave into the humidifier chamber and facing forward. The forward facing grips help orient the chamber for installation. In some configurations, the recesses extend only partially up the full height of the chamber. In some configurations, the recesses are opposed to each other such that a gripping force can be applied with fingers and thumb by the user.

With reference to FIG. 4A, the humidification chamber 104 can be packaged with port caps 160 covering the inlet 110 and the outlet 112. The port caps 160 can seal or generally enclose the chamber 104 during shipping and storage. In the illustrated embodiment, an intermediate member extends between and connects the port caps 160, and the intermediate member includes a pull tab or loop 161. The pull tab 161 advantageously allows the user to remove the port caps 160 more easily during the appropriate stage of set-up. The pull tab 161 is visually intuitive such that the user will typically understand that he or she is to pull on the pull tab 161 without requiring additional instructions. The port caps 160 can include legs 162 that extend into the inlet 110 and the outlet 112 and that restrain the float 150 in position for shipping. In some configurations, the liquid conduit 118 can be wound around, and can be contained by, a winder 166 provided on the chamber 104. During set-up, after the humidification chamber 104 is installed on the heater base 102, the port caps 160 can be removed, preferably prior to the liquid conduit 118 being unwound and connected to the liquid source via a spike 164. Once the spike 164 connects to the liquid source, liquid will begin filling the chamber 104. However, if the liquid conduit 118 is connected to the liquid source before the port caps 160 are removed, there is a risk of the chamber 104 overfilling because the float 150 is still restrained and cannot function to slow or stop the flow of liquid into the chamber 104.

To reduce the likelihood of overfilling, in some embodiments, the chamber 104 is packaged with the liquid conduit 118 captured between the inlet port 110 and the outlet port 112 of the chamber 104 and the port caps 160. The liquid conduit 118 can further be somewhat obscured from the operator until the port caps 160 have been removed. Preferably, however, the presence of the liquid conduit 118 below the port caps 160 can be viewed with the port caps 160 in position, which leads the operator to remove the port caps 160 to access the liquid conduit 118. Furthermore, removal of the port caps 160 preferably results in the unwinding or unfurling of the liquid conduit 118. This packaging arrangement also reduces or eliminates any need for a winder 166 to contain the liquid conduit 118 and the set-up steps of removing the winder 166 from the chamber 104 and unwinding the liquid conduit 118 from the winder 166. In some embodiments, the spike 164 and/or liquid conduit 118 are free-floating and not constrained by a winder 166 or the port caps 160. This can help reduce possible operator confusion as to whether the liquid conduit 118 should be unwound during set-up. In some arrangements, the spike 164 freely hangs exposed to further encourage removal of the port caps 160. In some configurations, the spike 164 is partially exposed and partially captured by the port caps 160 which encourage removal of the port caps 160 to access the spike 164.

Additional features can help reduce the likelihood of operators mistaking the port caps for operational components of the system intended to remain in place during use. For example, an alternative port cap 170 can include a single flat surface spanning the top of both ports and simple side faces encircling the ports and, optionally, the liquid conduit 118 as shown in FIGS. 4B and 4C. This design can give the port cap 170 the appearance of a lid to be removed from the chamber 104 before use. The port cap 170 can also include a lip detail around some or all of a perimeter of the flat top surface that the operator can grip for removal. The flat top surface provides a surface for an optional instruction label or a label having an image of, e.g., a trash can to indicate to the operator that the port cap 170 is supposed to be removed and discarded. In some configurations, the port caps can be formed of a material or have a coloration that will confirm an instinct to dispose of the port caps.

Figure 4F:
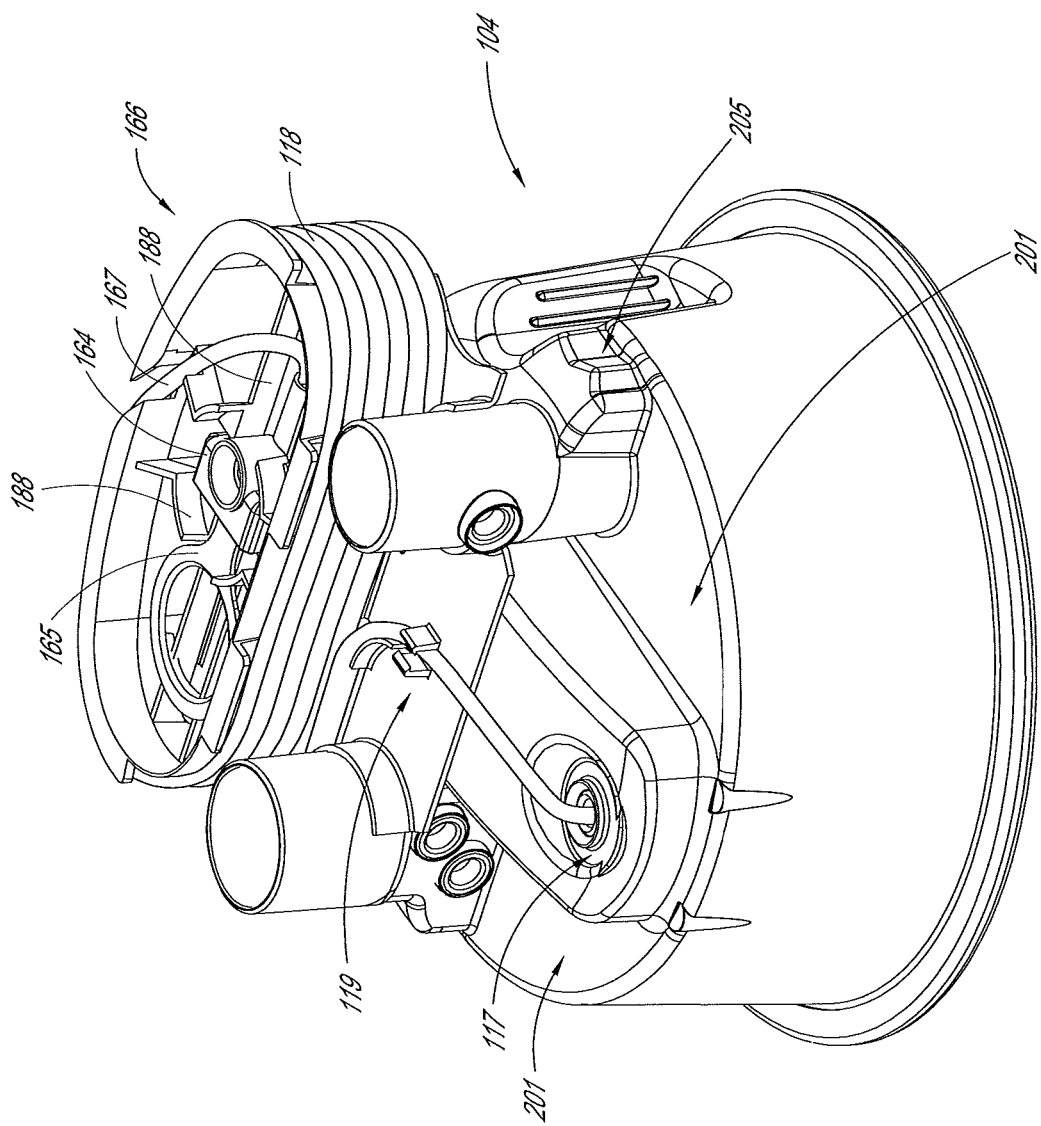

With reference to FIG. 4D, another example embodiment of a port cap 170 that can be used with a winder 166 includes a cap body 172 and a float retainer 174 having a tab or pull loop 176 and legs 162 that extend into the inlet 110 and the outlet 112 to restrain the float 150. The cap body 172 can be formed to be at least partially translucent or substantially transparent to reveal the conduit contained within the cap body 172. The cap body 172 can include an arrow and/or other visual or other indicators to direct the operator on the correct direction for insertion of the chamber 104 on the heater base 102. In some embodiments, the cap body 172 can include a label that includes instructions for set-up of the chamber to increase the likelihood of a correct or desired sequence of set-up steps being followed by people performing set-up operations. In some embodiments, the float retainer 174 is separate from the cap body 172 and can be removed from the chamber 104 before the cap body 172 as shown in FIG. 4E. Removal of the cap body 172 exposes the winder 166, as shown in FIG. 4F. Alternatively, the float retainer 174 can be integrally molded with or coupled to the cap body 172 so that both components are removed simultaneously, for example, by pulling on the pull loop 176. The pull loop 176 can advantageously allow the port cap 170 to be removed more easily. Both embodiments advantageously ensure that the float retainer 174 is removed when the winder 166 is exposed so that the float 150 is unrestrained before the liquid conduit 118 is connected to the liquid source. In some embodiments, the winder 166 is coupled to the chamber 104 with clips or other features that connect to, clip to or otherwise engage the chamber ports. As shown in FIG. 4F, the liquid conduit 118 can extend from a liquid inlet 117 in the chamber 104, around the winder 166, and into the winder 166 through a vent 167 to couple to the spike 164, which can be seated within the winder 166 as shown in the illustrated embodiment. In the illustrated embodiment, the cap body 172 is sized and shaped to also cover the liquid conduit 118 when in place for shipping and/or storage. In some configurations, the winder 166 includes features to secure the spike in a horizontal position (e.g., a shipping position) and in a non-horizontal or vertical position (e.g., a testing position). For example, the winder 166 can have a generally oval shape and can include a longitudinal receptacle 186 within the winder 166 configured to receive and/or to secure the spike in a horizontal shipping position. The winder 166 can also include a generally circular receptacle 188 configured to receive a grip portion 190 of the spike 164 (shown in FIG. 4J) so that the spike 164 can be placed in a generally vertical position for testing. The liquid conduit 118 can be secured in the liquid inlet 117 with an adhesive such as glue or any other suitable technique. A tubing holder 119 can help secure the liquid conduit 118 to a portion of the winder 166 or to the top of the chamber 104 and help route the liquid conduit 118 from the liquid inlet 117 to the winder 166. In some embodiments, the operator can remove the spike 164 from the winder 166 and unwind the liquid conduit 118 from the winder 166 to connect the spike 164 to the liquid source. In some embodiments, the operator can remove the winder 166 from the chamber 104 and discard the winder 166 after unwinding the liquid conduit 118.

Additional embodiments of liquid conduit 118 packaging are shown in FIGS. 4G and 4H. In both illustrated embodiments, the liquid conduit 118 is wound into a looped configuration, for example, by winding the liquid conduit 118 around a jig. In some embodiments, a label 218 is attached to the liquid conduit before winding and used to secure the liquid conduit 118 in the looped configuration. In the embodiment of FIG. 4G, the looped liquid conduit 118 is placed within a foldable card 178 coupled to the top of the chamber 104. The card 178 can be made of cardboard, plastic, a flexible material, or any other suitable material, and a bottom portion 178a can be secured to the chamber 104 with an adhesive and/or by cutouts 280 configured to be placed around the chamber inlet and outlet ports. A top portion 178b of the card 178 can be folded over the bottom portion and secured with cutouts configured to be placed around the chamber inlet and outlet ports and/or with port caps 160. In some embodiments, the spike 164 is secured to a base of the card 178 between the top and bottom portions via a slot or clip. The bottom portion 178a of the card can include a slit 282 to accommodate the liquid conduit 118 extending between the card 178 and the liquid inlet 117. In some configurations, the looped conduit can be placed width-wise on the card. In the embodiment shown in FIG. 4I, the looped liquid conduit 118 is placed in a molded cavity 111 on the top of the chamber 104 and protected by a tube enclosure 179, which can include port caps 160. A bottom surface of the tube enclosure 179 can include a feature to secure the spike 164. In some embodiments, a label with branding, instructions, and/or other information can be attached to the tube enclosure 179, the card 178 (e.g., the top portion 178b or the card 178). In other words, in some configurations, one or more of the card (e.g., the top portion 178b of the card 178) and the tube enclosure 179 can incorporate one or more surfaces that can be used for instructions (e.g., unpacking instructions, set-up instructions or the like), labels or warnings. In some configurations, the card 178 can include sequential instructions that increases the likelihood of a correct or desired sequence of set-up steps being followed by people performing set-up operations. For example, the card 178 can be provided with sequential or staggered steps to follow. In some configurations, the card 178 or another component can explain only steps that involve exposed or accessible components.

Figure 4I:
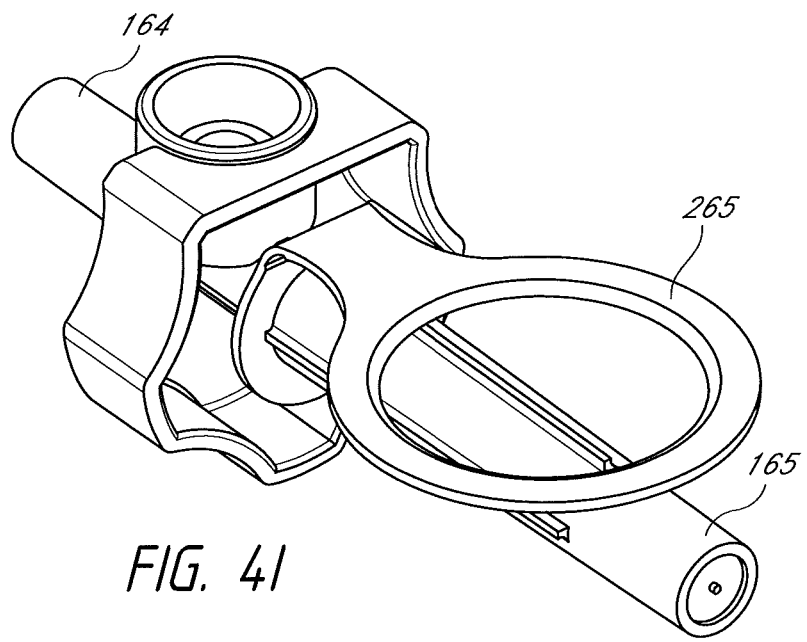
FIG. 4I illustrates a spike including a sheath.
Figure 4J:
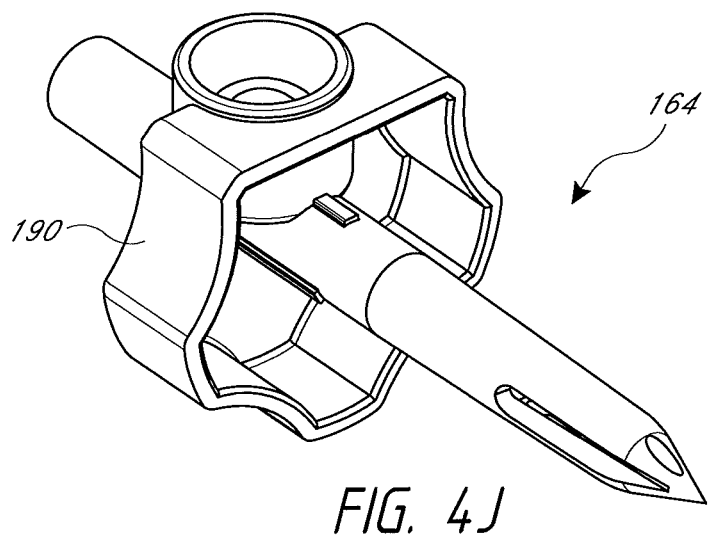
FIG. 4J illustrates the spike of FIG. 4I without the sheath.
Figure 4K:
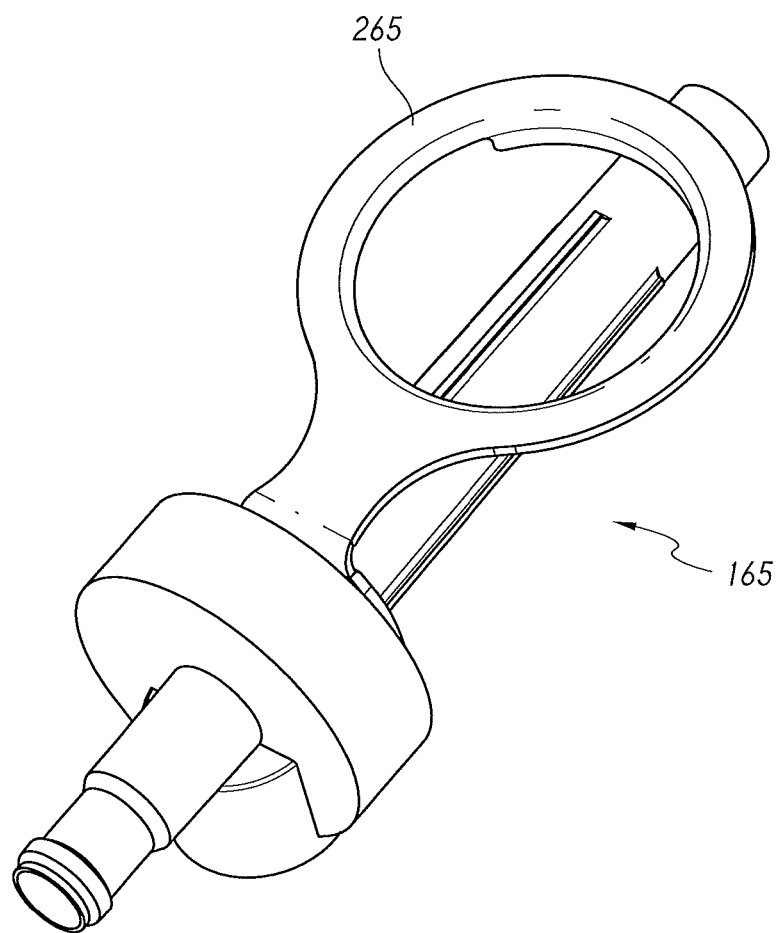
FIGS. 4K-4L illustrate a spike including a sheath.
Figure 4L:
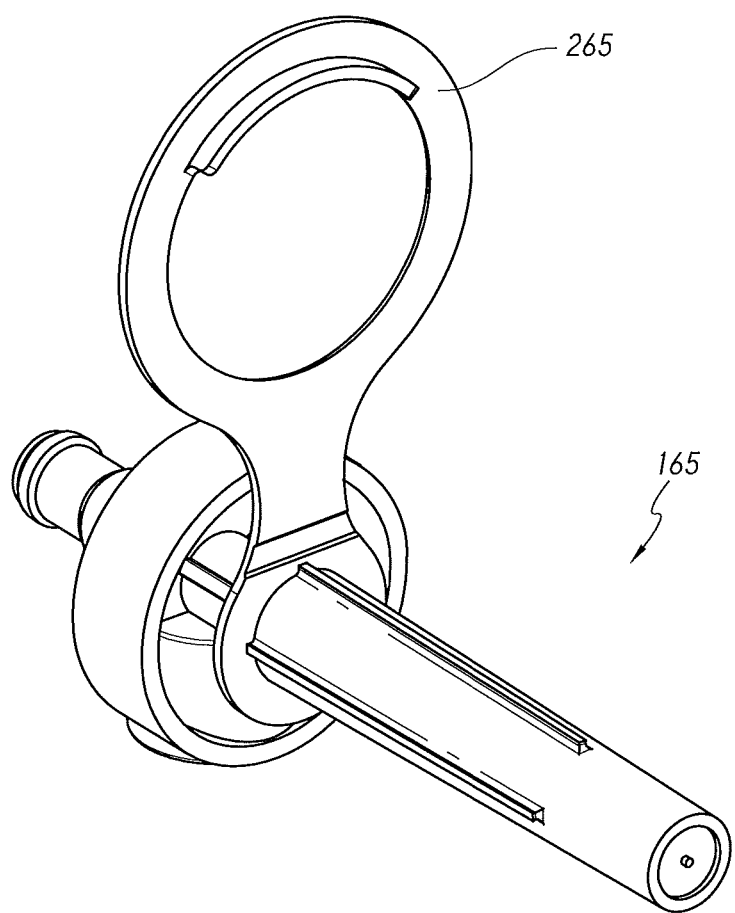
Figure 4M:
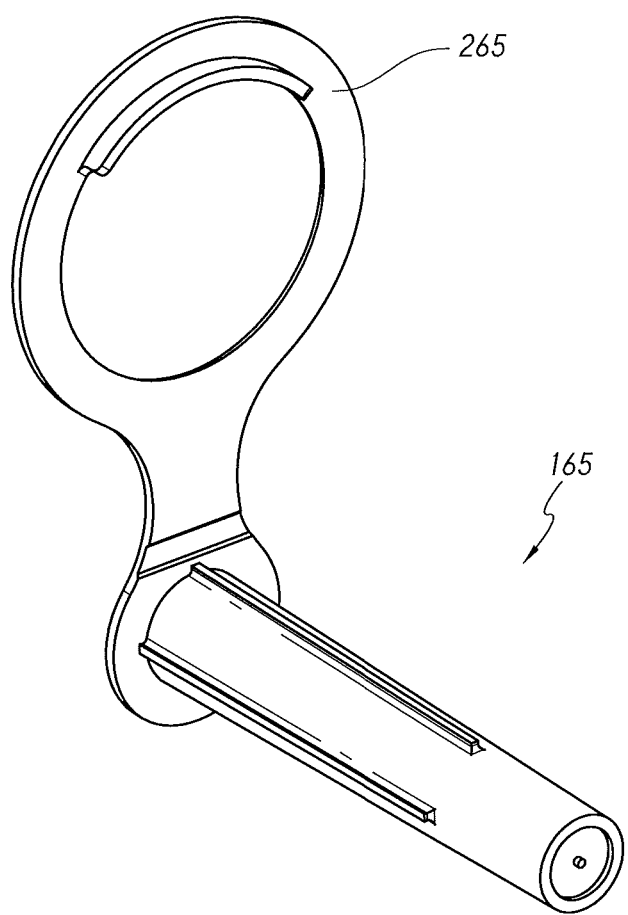
FIG. 4M illustrates the sheath of FIGS. 4K-4L removed from the spike.

As shown in FIGS. 4F and 4I, the spike 164 can be packaged with a spike cap or sheath 165 that the operator removes before use, as shown in FIG. 4J. The sheath 165 can include a tab or a similar feature for easier removal of the spike 164 from the winder 166 and/or of the sheath 165 from the spike 164. In the illustrated embodiment, the sheath 165 includes a loop or ring 265. If desired, the user can use the ring 265 to hang the sheathed spike 164 on, for example, a medical stand, until the user is ready to use the spike 164. FIGS. 4K-4L illustrate another example embodiment of a spike 164 packaged with a sheath 165 including a ring 265. FIG. 4M shows the sheath 165 alone. As shown in FIGS. 4L and 4M, the ring 265 can be lifted to an approximately 90° angle relative to the sheath 165 to allow the user to more easily grasp the ring 265 and/or more easily hang the ring 265 on a medical stand. In some configurations, the cap is not connected to any other member such that the operator knows to remove the cap. Labels also can be used to instruct the operator on how to set up the liquid conduit 118 and liquid source. Typically, humidification systems 100 utilize water to humidify gases passing through the humidification chamber 104. To indicate to the operator that the spike should be connected to a water bag rather to another type of liquid, such as saline, the liquid conduit 118 and/or the chamber 104 can include labels, reading "$H_2O$." Preferably, any such visual indicator, including the label, is positioned closer to the spike than to the body of the chamber when the conduit is stretched outward. The label on the liquid conduit 118 can also help draw the operator's attention to the water spike 164, which may not be obvious to the operator when concealed by the spike cap. The chamber 104 can also include labels to indicate the appropriate water level.

In some configurations, a spike can be secured to tubing using any suitable technique. For example, the spike can be secured to tubing using adhesives, sonic welding, interference fit, or the like. A label then can be attached to the tubing. In some configurations, the label can be loosely looped over the tubing and can include a sticky end (e.g., exposed adhesive). In some configurations, the label can be positioned closer to the spike than to another end of the tubing. The tubing can be wound around a jig or the like and secured in a looped configuration using the label (e.g., using the sticky end to tack the end of the label to another portion of the label). When winding the tubing, the ends preferably are provided with enough slack to connect the tubing and spike to the chamber. The end without the spike can be secured to the chamber using any suitable technique. In some configurations, the end without the spike can be inserted into a water inlet hole of the water chamber and fixed with glue or the like. The ends of the loop of tubing can be placed over or between the inlet and outlet ports of the chamber. The spike can be secured into a receptacle. In some configurations, the receptacle can be formed in, or secured to, a portion of the chamber. In some configurations, the spike is secured to the chamber with the point extending away from the chamber for testing. Testing can be conducted on the assembled chamber. After testing, the spike can be removed from the chamber and the spike and tubing can be secured in any suitable manner for shipping, including those set forth above.

The humidification system 100 can include reusable temperature and/or flow probes at or near the humidification chamber 104. For example, a flow sensor can be positioned in the chamber inlet 110 to sense the flow rate of the gases entering the chamber 104 from the gases supply 130. A temperature sensor can be positioned in the chamber inlet 110 to sense the temperature of the gases entering the chamber 104 from the gases supply 130. A temperature sensor can be positioned in the chamber outlet 112 to sense the temperature of the humidified gases leaving the chamber 104. A flow sensor can also or alternatively be positioned in the chamber outlet 112 to sense the flow rate of gases leaving the chamber 104 to be delivered to the user.

Figure 5B:
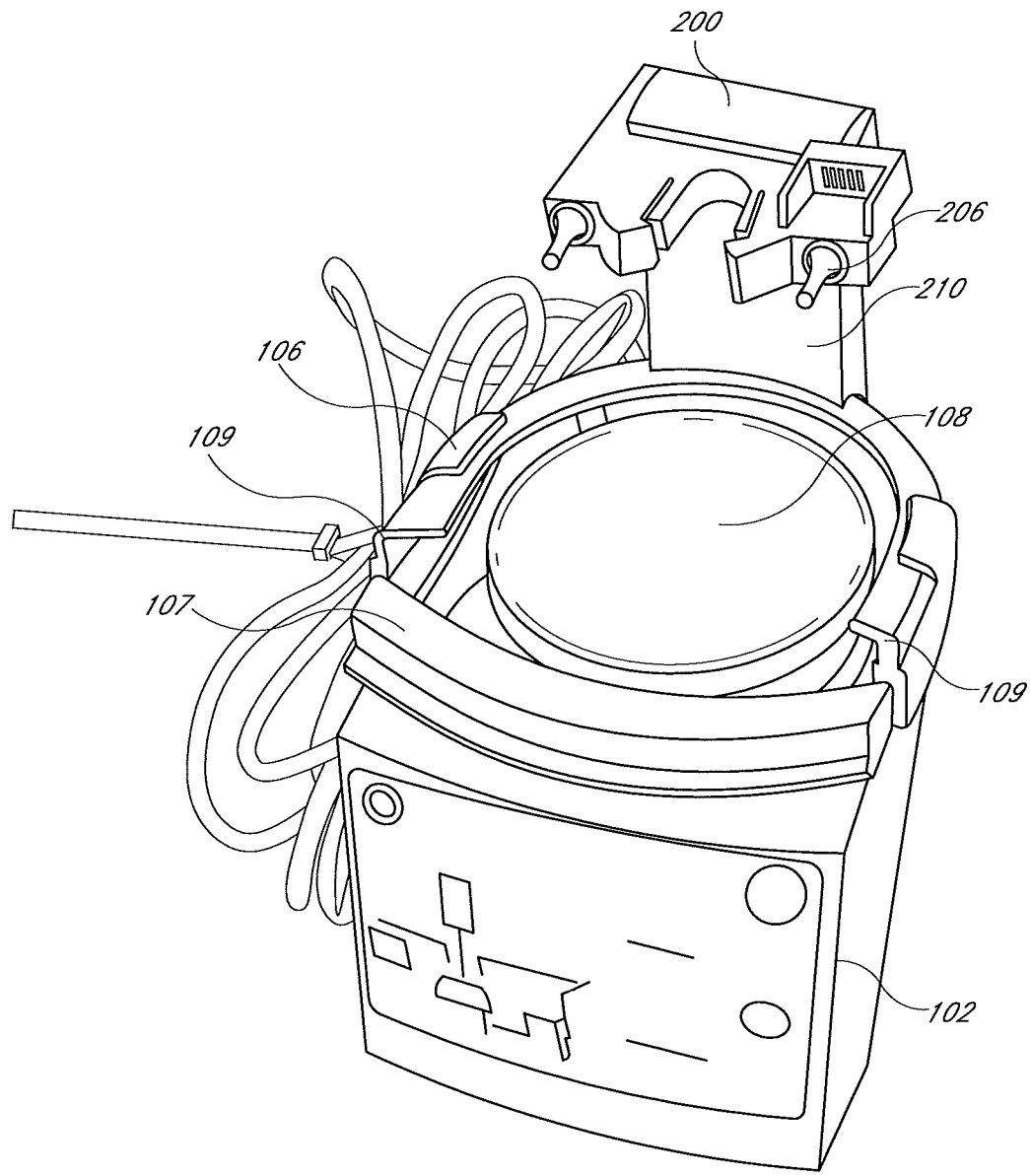
FIG. 5B illustrates a sensor cartridge coupled to a heater base.
Figure 5C:
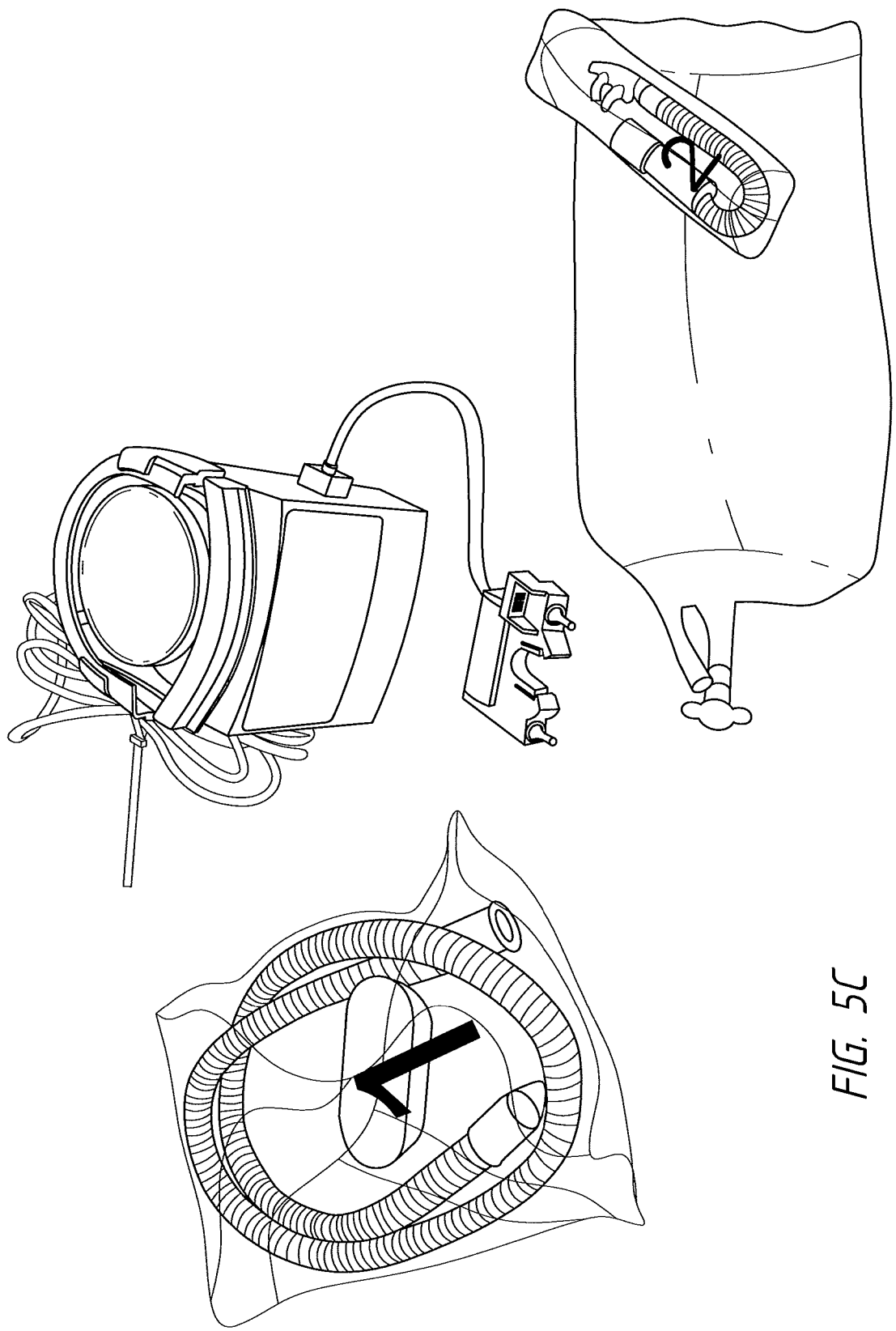
FIG. 5C illustrates a sensor cartridge connected to a heater base with an electrical cable.

Reusable temperature and/or flow sensor probes 206 can be integrated into a sensor cartridge module 200, as shown in FIG. 5B. FIG. 5C shows the sensor cartridge module 200 connected to the heater base with an electrical cable. The sensor cartridge module 200 in FIG. 5B, however, is mechanically and electrically connected to the heater base 102 via a spine 210 and can therefore provide for the transfer of power to the sensors while also providing a mounting location for the sensors, for example but without limitation. In some configurations, the spine 210 and the port cap can have an interfacing configuration such that movement of the chamber with the port cap in position toward the spine during mounting of the chamber to the heater base will cause the spine to lift the port cap from the chamber. Such a configuration increases the likelihood of the operator removing the port cap from the chamber. Other suitable configurations also can be used.

Figure 6:
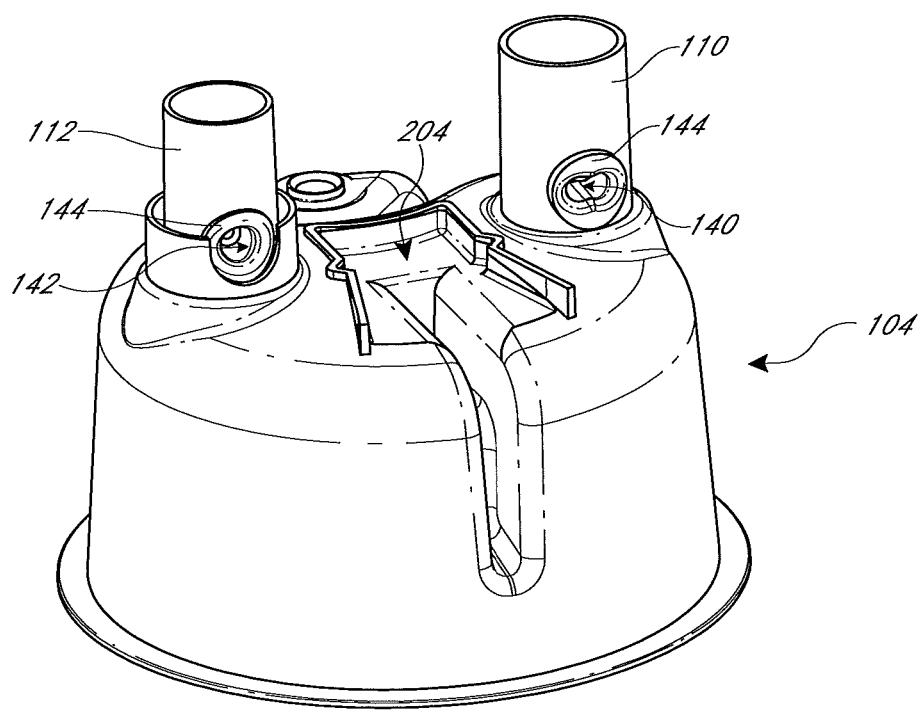
FIG. 6 illustrates a humidification chamber.

The sensor cartridge module 200 also allows for the transfer of data between the sensors and the processor 114 in the heater base 102. The chamber inlet 110 and outlet 112 can have apertures 140, 142 therethrough, for example as shown in FIG. 6. Probe membranes or grommets 144 sized and shaped to receive the temperature and/or flow probes 206 can be positioned within and pneumatically seal the apertures 140, 142. In the configuration of FIG. 5B, the operator is encouraged to position the chamber base below the rim edge 106 because otherwise the probes attached to the spine will not properly align with the respective apertures.

Correct insertion of the chamber 104 into the heater base 102 can automatically position the sensor probes 206 within the apertures 140, 142 of the chamber inlet 110 and outlet 112. This can advantageously allow for an easier set-up compared to separate reusable sensors, which must be manually inserted and electrically connected to the heater base 102, and reduce the possibility of improper electrical connection, improper pneumatic sealing and/or assembly. The probe membranes 144 protect the probes from direct contact with the gases passing into and out of the chamber 104. The probes therefore can be reused without requiring cleaning and storage of the probes 206 and disconnection and reconnection of wires between uses.

To help guide the operator through installation of the chamber 104 on the heater base 102 and proper connection with the sensor cartridge module 200, the chamber 104 and sensor cartridge module 200 can include lead-in features, such as corresponding male and female connections. For example, one or more of the base 102 and the cartridge module 200 can include structures that mate with structures 201 on the chamber 104. In the configuration of the chamber 104 shown in FIG. 4F, the structures 201 are recessed portions. Thus, the chamber 104 can have a shorter vertical height on the portion closest to the heater base 102 when mounted while the chamber 104 has a taller vertical height on the portion that is positioned away from the cartridge module 200. Such a configuration reduces the likelihood of the chamber being inserted into the base 102 backwards, which can result in damage to the sensors. The cooperating formations greatly increase the likelihood that coupling of the chamber 104 to the base 102 is only achieved in a correct rotational orientation of the chamber 104. Moreover, the cooperating structures can provide visual cues to the proper rotational orientation of the chamber 104. The cooperating structures can be a male on the base and a female on the chamber, a female on the base and a male on the chamber, or any combination of male and female portions on the base and the chamber.

By way of another example, the sensor cartridge module 200 can include a central male projection 202 configured to slide into a female recess 204 in the chamber 104. Alternatively, the chamber 104 can include a male projection configured to slide into a center of the sensor cartridge module 200. Preferably, the female recess 204 is configured in such a manner that only one orientation of the chamber relative to the male projection 202 is possible. Any other configuration or snap together assembly can be used. In some configurations, the chamber 104 can include a chamfered or angled edge or protrusion 205 on the lateral sides, for example, but without limitation. These protrusions 205 can cooperate with a structure of the base 102 or on the cartridge module 200. The cooperation preferably helps to pull or encourage the chamber 104 into a fully seated position relative to the base 102. Thus, the protrusions 205 and the cooperating structures provide another example of structures that can orient and properly position the sensor probes 206 relative to the chamber. These means for orienting the chamber relative to the heater base also advantageously aid proper positioning of the sensor probes 206 within the chamber ports. Advantageously, when the chamber 104 docks on the sensor cartridge module 200, the sensor probes can be automatically inserted into the chamber ports to the appropriate distance or depth. In other words, the risk of the probes 206 not fully inserting to the ports of the chamber 104 can be reduced or eliminated. Preferably, the connection between the sensor cartridge module 200 and the chamber 104 is generally horizontally (e.g., parallel with an upper surface of the heater plate).

In some configurations, the chamber can have recess that accommodates a protrusion from the spine or other portion of the heater base. Such a configuration can help guide the chamber into position on the heater base in a desired rotational orientation. In some configurations, rather than being translated into position, the chamber can be rotated into position on the heater base. For example, slots can be provided with posts that can slide vertically downward into the slots such that rotation of the chamber will position the posts under the rim edge 106. In some configurations, if the sensor cartridge module 200 is mounted to the chamber before the chamber is mounted to the heater base, rotation of the chamber can establish an electrical connection between components mounted to the chamber (e.g., sensors) and the heater base. Rotation of the chamber also defines a horizontal connection direction. Other configurations also are possible.

Some humidification systems 100 also include temperature and/or flow rate sensors at various locations in the breathing circuit to monitor conditions of the gases as they travel through the system 100 to and from the user 128. Some such systems include reusable temperature sensors at or near the user end of the inspiratory conduit 122 to ensure the gases reaching the user 128 are at an appropriate temperature. Because the various conduits of the circuit are typically disposable, reusable temperature sensors must be separately coupled to the inspiratory conduit 122 during set-up and must further be connected to the heater base 102 for power and data transfer. The user may forget to connect the sensor and/or sensor cable entirely, or may inadvertently fail to fully insert the sensor into the inspiratory conduit 122, which can skew the sensor data. According to some embodiments of the present disclosure, a single-use user end temperature sensor and associated sensor cable can be integrated with the inspiratory conduit 122. This can advantageously eliminate the steps of connecting a separate sensor and sensor wires during set-up, as well as the steps and time required to clean and store reusable sensors.

In some embodiments, the sensor cartridge module 200 can allow for power and data transfer between the heater base 102 and the inspiratory conduit 122 user end temperature sensor and an inspiratory conduit 122 heater wire. The inspiratory conduit 122 chamber end connector can include an electrical connection for coupling to a corresponding connection on the sensor cartridge module 200. This provides a simpler alternative to using a reusable sensor cable to provide an electrical connection between the user end temperature sensor and the heater base 102 and a reusable heater wire adapter cable to provide an electrical connection between the inspiratory conduit 122 heater wire and heater base 102. The user end temperature sensor and heater wire can be coupled to the electrical connection of the inspiratory conduit 122 chamber end connector via wires that are integrated in or run alongside the exterior of the inspiratory conduit 122.

If the expiratory conduit 124 includes a heating element, e.g., a heater wire, the heating element is typically powered via an electrical cable connecting the heating element to the heater base 102. To help simplify set-up, both ends of the heating element electrical cable can have plugs of the same design. Corresponding sockets can be located on the heater base 102 and the expiratory conduit 124 gases supply end connector. Either end of the heating element electrical cable can be coupled to either the expiratory conduit 124 gases supply end connector socket or the socket of the heater base 102. The operator therefore does not need to spend excess time determining the correct orientation for the heating element electrical cable.

Figure 7A:
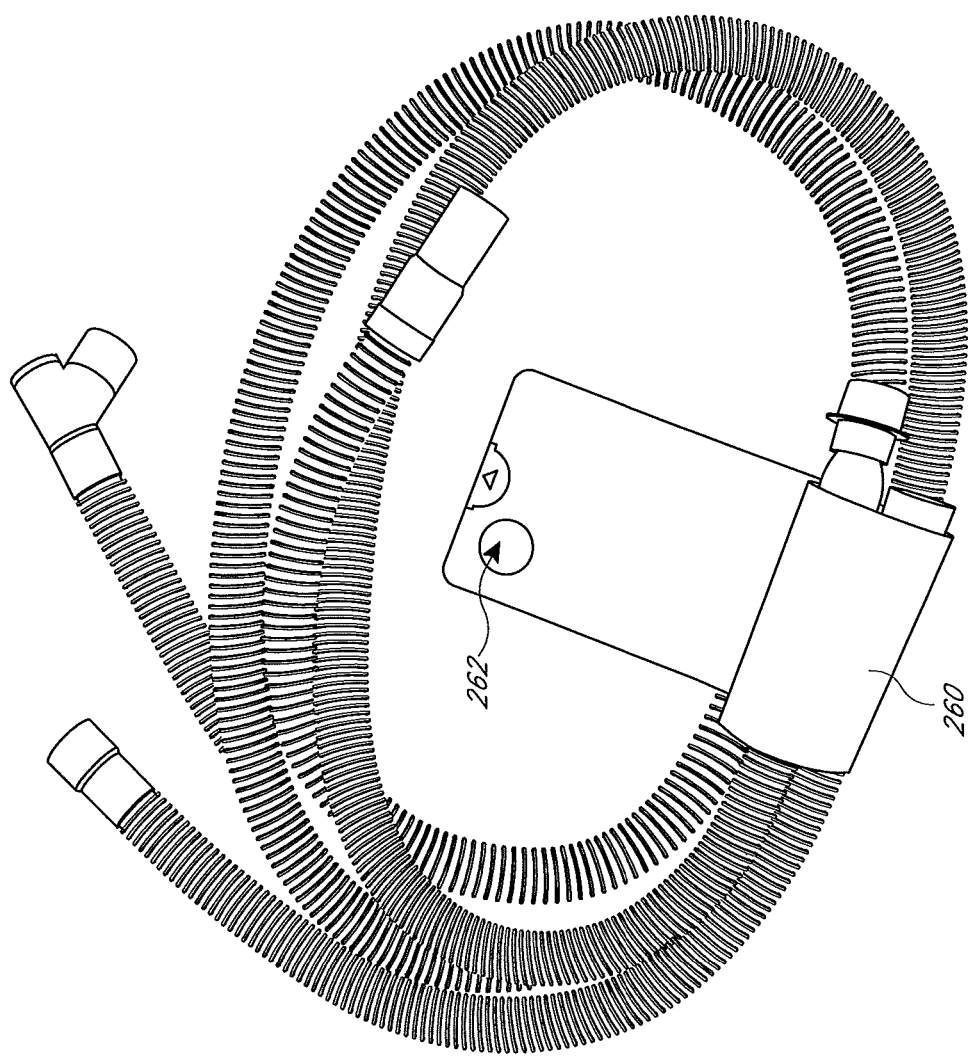
FIG. 7A illustrates breathing conduits as packaged.

As explained herein, the breathing circuit can include multiple conduits requiring multiple connections to the chamber 104, the interface 126, and/or the gases supply 130. The length of the conduits can make them difficult to handle and control during set-up, increasing the risk of the conduits being accidentally dropped on the ground and possibly contaminated. To improve handling and control during removal from packaging and set-up, the circuits can be packaged and held together in a looped configuration with a circuit sleeve 260 as shown in FIG. 7A. In some embodiments, the sleeved conduits can be packaged in a protective plastic bag or the like. In some embodiments, the circuit sleeve 260 is made of cardboard or a thin plastic sheet, although other materials are also possible. The circuit sleeve 260 can be looped or wrapped around the conduits and closed or held together with, for example, staples, tape, and/or an adhesive, e.g., glue. In some embodiments, ends of the sleeve 260 have interlocking features to close the sleeve 260 around the conduits, for example, interlocking slits or a tab and corresponding slot. The conduits can also be held in a looped configuration by tape, rubber bands, straps, or the like.

The looped configuration can advantageously allow the operator to hang the conduits on, for example, the forearm, the heater base, or another object to free up the operator's hands for other set-up tasks. In some embodiments, the circuit sleeve 260 includes a hole 262 that can be used to hang the looped conduits on a hook, for example, a hook used to hang the water bag or an I.V. bag, as an alternative to placing the conduits on other hospital surfaces that can increase the risk of contamination. The circuit sleeve 260 can be positioned on the conduits to conceal selected conduit connectors and help direct the operator's attention to visible conduit connectors, which can be the connectors that should be connected first during the set-up process. If the operator makes the appropriate connections with the visible conduit connectors before removing the circuit sleeve 260 to expose the remaining connectors, the operator will have a reduced number of possible connections, thereby making it easier and more likely to correctly complete the set-up. In some embodiments, the circuit sleeve 260 can include set-up instructions, in writing and/or pictures, to help direct a preferred set-up sequence to achieve the correct set-up. The circuit sleeve 260 can also be positioned on the conduits to cover and/or isolate any sharp edges or corners (e.g., portions of the connectors) to help reduce the possibility of damage to, for example, other circuit components, the chamber, and/or the packaging material during shipping or the like.

Figure 7B:
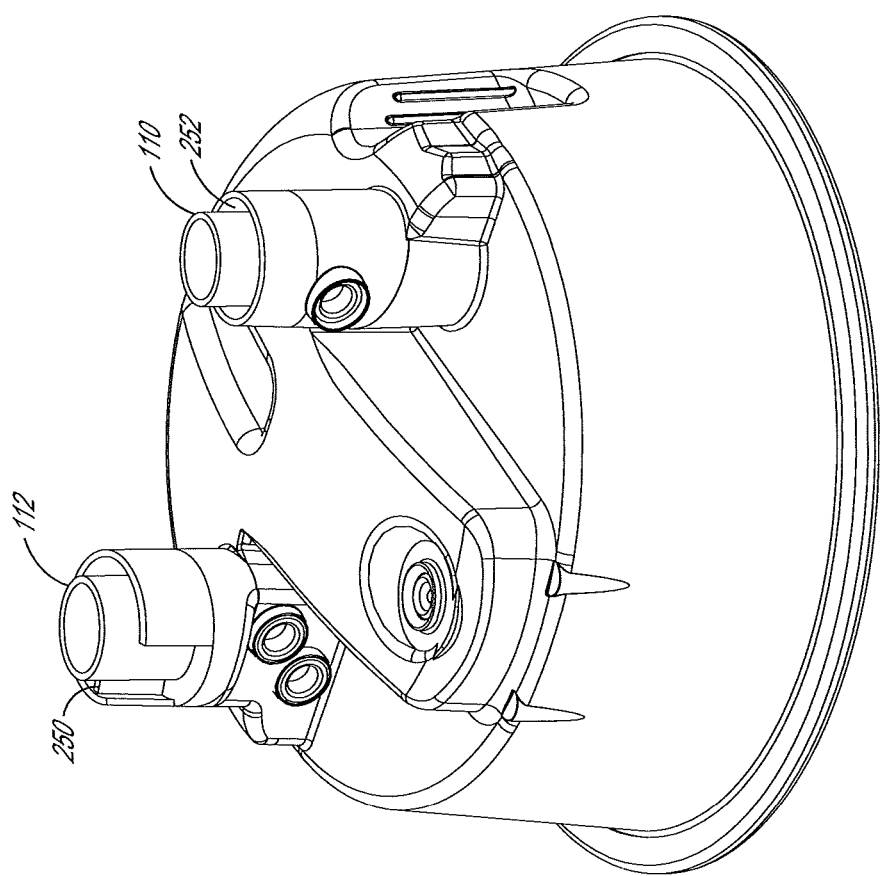
FIG. 7B illustrates a humidification chamber with features to promote proper connections.
Figure 8:
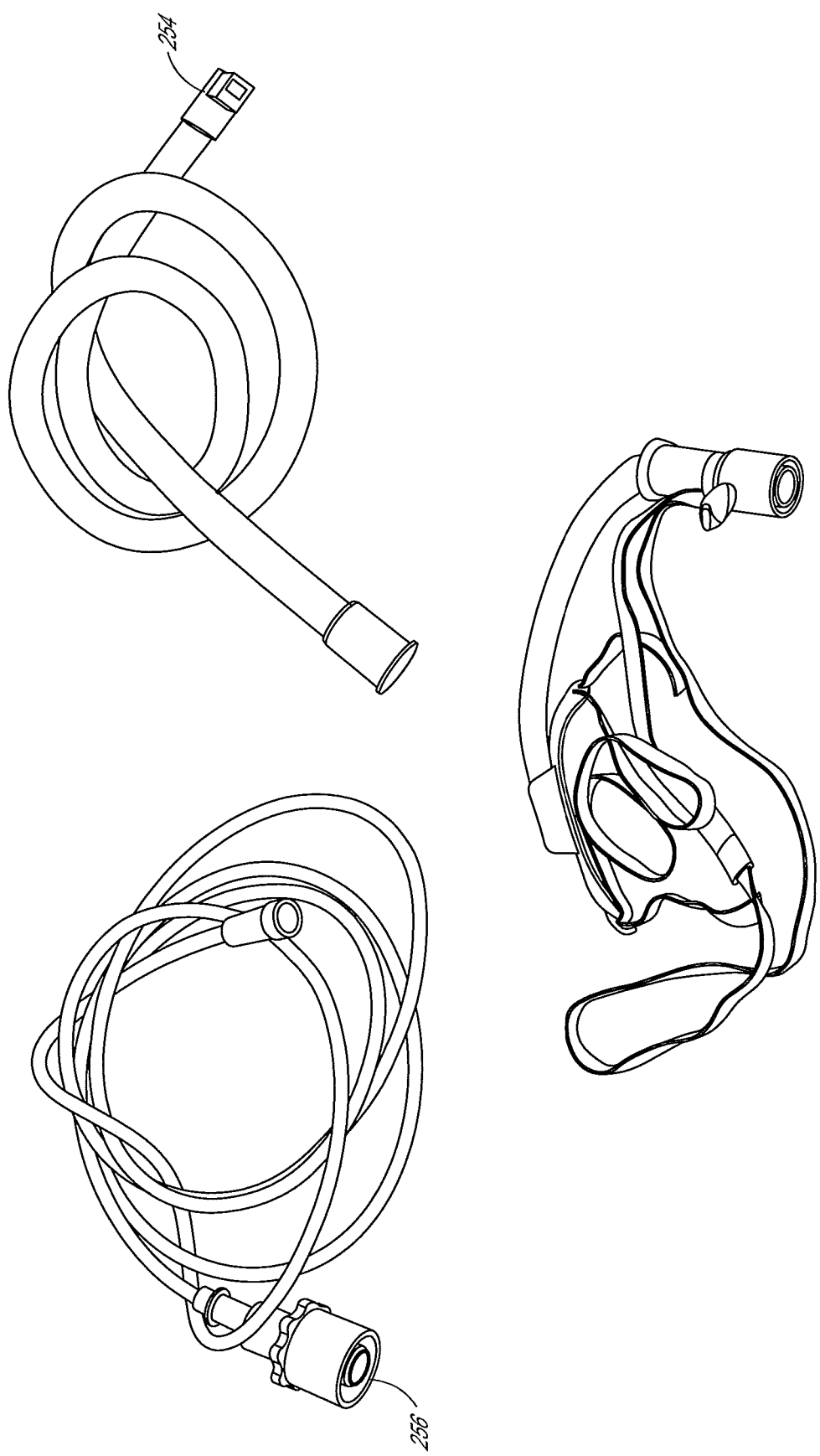
FIG. 8 illustrates conduits having features corresponding to those shown in FIG. 7B.

To help reduce the likelihood of incorrect connections during set-up, the conduit connectors, chamber inlet 110 and outlet 112, gases supply output 132 and input 130, interfaces 126, and/or Y-piece 127 can have varying diameters to help prevent incorrect connections from being made. In some embodiments, some or all of the connections can include details, such as rib details, that allow the appropriate components to be connected, but inhibit improper connections. For example, the chamber outlet 112 or inspiratory conduit port can include a rib detail 250 circumferentially surrounding the port 112 as shown in FIG. 7B. The inspiratory conduit chamber connector can include a corresponding rib detail 254 configured to engage the chamber outlet port rib detail 250 as shown in FIG. 8. The chamber inlet or supply conduit port can similarly include a circumferential rib detail 252 to engage a corresponding rib detail 256 on the supply conduit chamber connector. Other components, such as an inspiratory tube user end connector, expiratory tube user end connector, expiratory tube gases supply end connector, and/or supply conduit gases supply end connector can include outwardly extending rib details. In some configurations, different diameters can be used to make it difficult if not impossible to physically connect the wrong conduit to the wrong port. In addition, as described above, it is possible to form each end of each hose to have a unique configuration to help reinforce the desired connections. Other configurations are also possible.

In some embodiments, various components can be color coded to help guide the operator through the set-up process and help reduce the likelihood of incorrect connections. For example, the supply conduit 120 chamber end connector and chamber 104 inlet 110 port can be similarly colored to a first color, for example, green, to indicate to the operator that those two components are intended to be connected. Similarly, the inspiratory conduit chamber end connector and chamber outlet port can be color-coordinated to a second color, for example, blue. For a dual-limb circuit, the interface 126 and/or Y-piece 127 can be color-coordinated to a third color, for example, grey. For a single-limb circuit, the interface and the inspiratory conduit patient-end connector can be color-coordinated to a fourth color, for example, blue. The sensor cartridge module 200 temperature and flow probes 206 can be color-coordinated with probe membranes 144, for example turquoise. An adapter cable and plugs for the expiratory conduit heating element can be color-coordinated with sockets on the expiratory conduit gases supply end connector and the heater base 102, for example, yellow. The components intended to be discarded during set-up, for example, the port caps 160, 170, winder 166, a Y-piece cap, and/or a cap for the water spike 164 can be colored similarly, for example, semi-transparent yellow or orange. Preferably, the cap for the water spike 164 is transparent, translucent or otherwise configured with slots, gaps, holes or the like to indicate to the operator that the spike is positioned within the cap. The supply conduit gases supply end connector and expiratory conduit gases supply end connector can be color-coded, for example, pink. In some embodiments, the conduits themselves can be differentiated through color. For example, the supply conduit 120 can be green, the inspiratory conduit 122 can be blue, and the expiratory conduit 124 can be white. In some embodiments, colors may be selected so that operators with reduced color recognition (such as red-green color blindness) are still able to differentiate the different components. In some arrangements, where an order is preferred, the color coding to be that over color mixing (e.g., red for first connections, orange for second connections, yellow for third connections, green for fourth connections and blue for fifth connections, for example but without limitation). Thus, patterns can be used to encourage proper progression as well as proper connections. In such configurations, LED, lights or color filters over lights can be used to show the color of the connections on the electric display or the colors can simply be shown on a display screen. Of course, other configurations and color palettes are also possible. In some embodiments, user instructions and/or errors can refer to the different components by their color.

In addition to or instead of color-coordinating the various components, the components can include corresponding symbols and/or text to indicate parts intended to be connected together. In some configurations, the first connections can be labeled "1" or "A" with the second connections being labeled "2" or "B," by way of example. In some embodiments, one or more of the conduits can include labeling indicating the proper direction of gas flow through the conduit in use. For example, the supply conduit 120 can include one or more arrows and, optionally, text similar to "TO HUMIDIFIER," pointing from the gases supply 130 end to the chamber 104 end. Similarly, the inspiratory conduit 122 can include arrows and optional text (e.g., "TO PATIENT") pointing from the chamber end to the user end, and the expiratory conduit 124 can include arrows and optional text (e.g., "FROM PATIENT") pointing from the user end to the gases supply end. Any suitable combinations or selection of shapes, colors, sizing, and/or symbols can be used to help a user make the desired connections and/or make the desired connections in the desired order. Further, in some embodiments, connectors of different components may be configured not to be able to connect to one another. For example but without limitation, the inspiratory conduit can have a connector that connects to only the outlet of the humidifier. In such embodiments, the connectors would reduce the likelihood of improperly connecting the component because the components would be very difficult, if not impossible, to connect incorrectly.

Figure 9A:
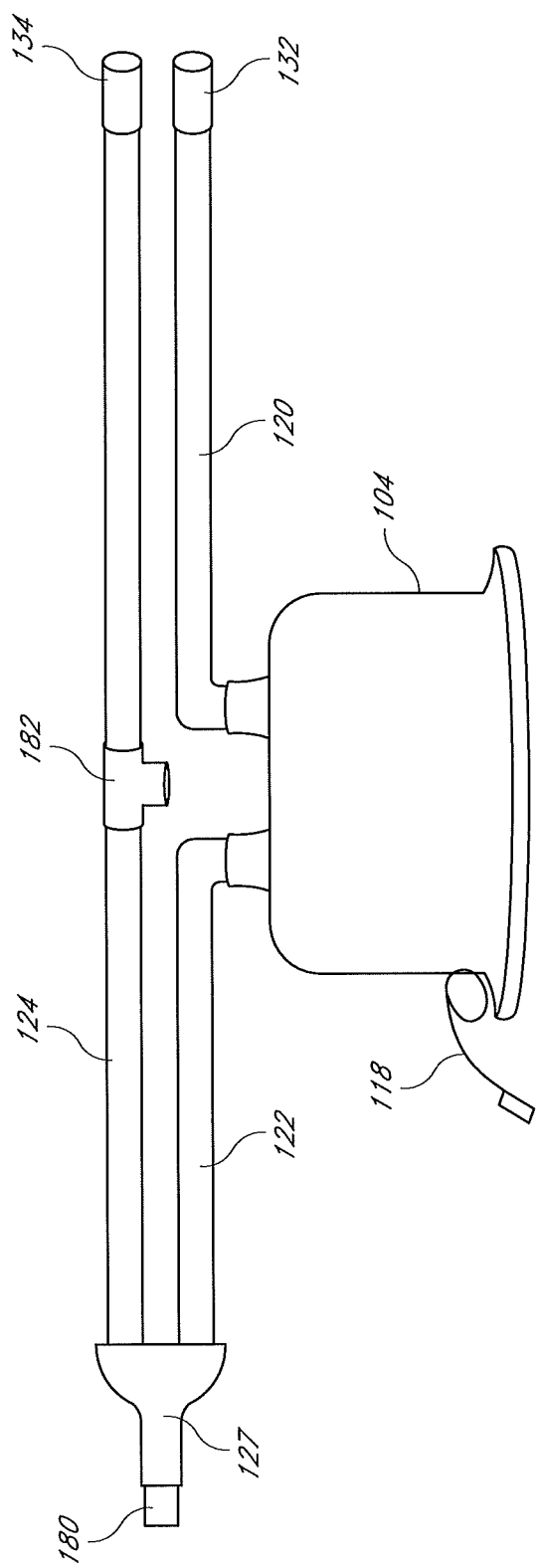
FIG. 9A illustrates a one-piece circuit.

To further simplify set-up of the breathing circuit, in some embodiments, the supply 120 conduit, the inspiratory 122 conduit, and, optionally, the expiratory 124 conduit can be coupled into a one-piece circuit, for example as shown in FIG. 9A. In some embodiments, the user ends of the inspiratory 122 conduit and the expiratory 124 conduit can be coupled to a Y-piece 127 configured to be coupled to the interface 126 in use. The Y-piece 127 can be packaged with a disposable cap 180 covering the user end to help inhibit contamination of the conduits and connections during setup. The electrical connectors and cables for temperature and flow sensors and heating elements can also be integrated into the one-piece circuit. In some embodiments, the chamber 104 can be provided pre-coupled with the one-piece circuit as well.

The conduits can be joined together or coupled via, for example, a mesh-type wrap or sheath surrounding at least some portion of the conduits. In some configurations, multiple portions of the conduits to be joined to form a multiple lumen structure can be joined with separate connecting means, including but not limited to mesh-type wrap, sheaths, belts, connectors, clips or the like. In some embodiments, the supply conduit 120 and the inspiratory conduit 122 can be removably coupled to the expiratory conduit 124 with individual clips. This can advantageously allow for the expiratory conduit 124 to be unclipped from the supply 120 conduit and the inspiratory 122 conduit and removed from the circuit when not needed.

Figure 9B:
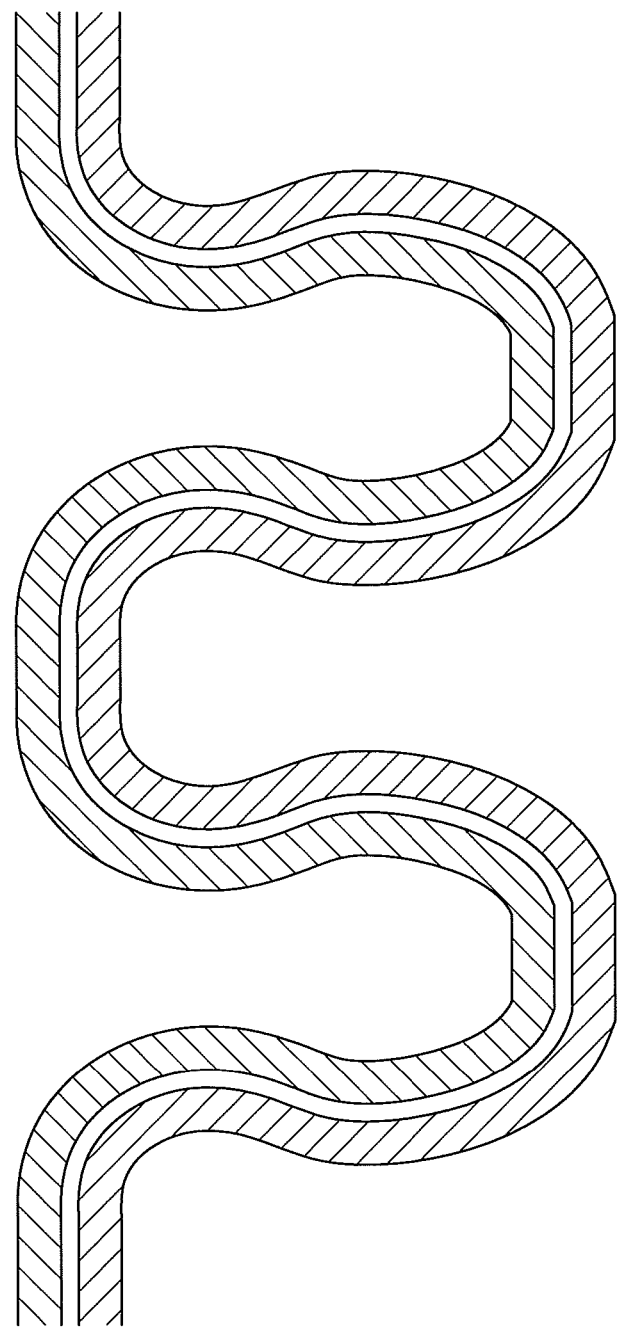
FIG. 9B illustrates a releasable connection system for a one-piece circuit.

In some embodiments, two or more of the conduits are structured to releasably connect together. In some embodiments, all of the conduits are structured to releasably connect together. A first conduit (e.g., the inspiratory conduit) can comprise a first portion of one of a hook material or a loop material and a second conduit (e.g., the expiratory conduit) can comprise a second portion of the other of a hook material or a loop material. The first and second portions can be configured to releasably connect together in a hook-and-loop arrangement. Other releasable connection systems can additionally or alternatively be used, such as a series of magnets whereby the two portions include magnets of opposite polarity, for example but without limitation. In another configuration, the outer wall of the inspiratory conduit and the outer wall of the expiratory conduit can be corrugated such that the peaks and troughs of the corrugation are mushroom-shaped. In such a configuration, the peaks of one conduit are configured to releasably snap-fit into the troughs of the other conduit such as shown in FIG. 9B, for example but without limitation. In such a configuration, the conduits may be directly connected to one another. The size and shape of the peaks and troughs can be the same on both conduits or can be complementary to reduce or eliminate the likelihood of, for example but without limitation, two expiratory conduits connecting together.

The one-piece circuit advantageously reduces the number of connections required during set-up and reduces the possibility of incorrect assembly. Additionally, during set-up of traditional systems, the various components may be placed on a table or bed to allow for sorting and identification. Components can be misplaced or fall to the floor, thereby risking damage and/or contamination. The one-piece circuit advantageously helps reduce these problems. The one-piece circuit with integrated electrical connectors and cables also allows for the various electrical connections to be made during set-up with the components to be connected being positioned in close proximity to each other. In some embodiments, a heating element connector plug 182 of the expiratory conduit 124 can be located along the length of the expiratory conduit 124 rather than at the gases supply 130 connector. The plug 182 can be positioned and configured to be connected to a socket on the sensor cartridge module 200 or elsewhere on the heater base 102, for example, on the front of the heater base 102 to improve visibility of and access to the socket. In such embodiments, the plug 182 may be automatically connected to the sensor cartridge module 200 when the expiratory conduit 124 and/or the chamber 104 is connected to the heater base 102.

Various features can help improve the ergonomics of the humidification system 100. For example, the socket on the expiratory conduit gases supply end connector can be oriented at, for example, about a 45° angle from a plane defined by the end of the conduit. The angle can enhance the visibility of the socket when the expiratory conduit 124 is connected to the either horizontally or vertically oriented return 134 of the gases supply 130. The angle can also help reduce the likelihood that the socket will be obstructed by other components or equipment making set-up more difficult. The heater base 102 socket can be located on a front face of the heater base 102 to enhance visibility and ease of access as compared to placement of the socket on, for example, a side of the heater base 102 or elsewhere.

In some embodiments, the expiratory conduit 124 gases supply 130 end connector and/or the supply conduit 120 gases supply 130 end connector can have an elbow shape. For example, the connectors can have an angle of about 120°. The elbow shape can advantageously allow the operator to position the direction of the expiratory conduit 124 and/or supply conduit 120 to and from the gases supply 130 so that the conduits do not obstruct other system components, such as the heater base 102 display. Any or all of the connectors, such as one or more of the expiratory conduit 124 and the supply conduit 120 gases supply end connectors and the inspiratory conduit 122 and the expiratory conduit 124 user end connectors can include grip details to help the operator more easily grip the connectors and perform a twisting motion for inserting and removing medical taper connectors. The grip details can be especially beneficial for operators wearing surgical gloves.

Figure 11:
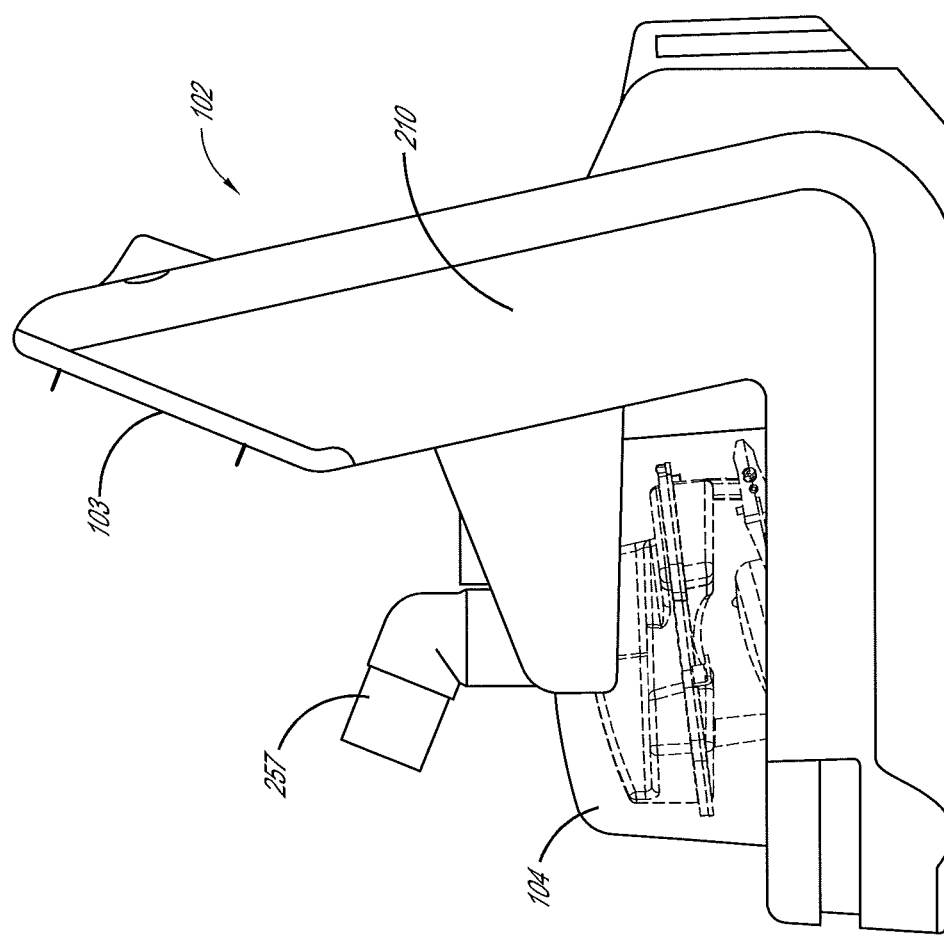
FIG. 11 illustrates a heater base and a humidification chamber.

In some embodiments, the heater base display 103 can be located on an upper surface of the spine 210, for example as shown in FIG. 11, for easier viewing. In the illustrated embodiment, the upper surface of the spine 210 and therefore the display 103 are oriented at an angle. The angled orientation can advantageously allow for an improved or easier view of the display 103 for the operator, particularly, for example, if the heater base 102 is positioned below the operator's horizontal line of sight. In some embodiments, the upper surface and/or display 103 can be oriented at an angle of about 22° from vertical, although other angles are also possible. In some embodiments, one or both of the supply conduit and inspiratory conduit chamber end connectors can have an angled or elbow shape. For example, in the embodiment of FIG. 11, the supply conduit chamber end connector 257 has an elbow shape so that it can be angled away from the heater base 102. The angled or elbow configuration can advantageously inhibit or prevent the connector and/or conduit from substantially obscuring the display 103, which serves to improve display visibility. In some embodiments, one or both of the supply and inspiratory conduit chamber end connectors can have an angle of about 112° so that the connector extends from the chamber port at an angle of about 22° above horizontal when coupled to the port, although other angles are also possible. In some embodiments, the spine 210, display 103, and/or one or both chamber end connectors can be configured so that the connector(s) is below the display 103 and/or a bottom edge of the upper surface of the spine 210, e.g., the connector(s)

extends below a line extending from the bottom edge of the display 103 perpendicular to the plane of the display and/or below a line extending from the bottom edge of the upper surface of the spine 210 perpendicular to the plane of the upper surface.

Figure 10:
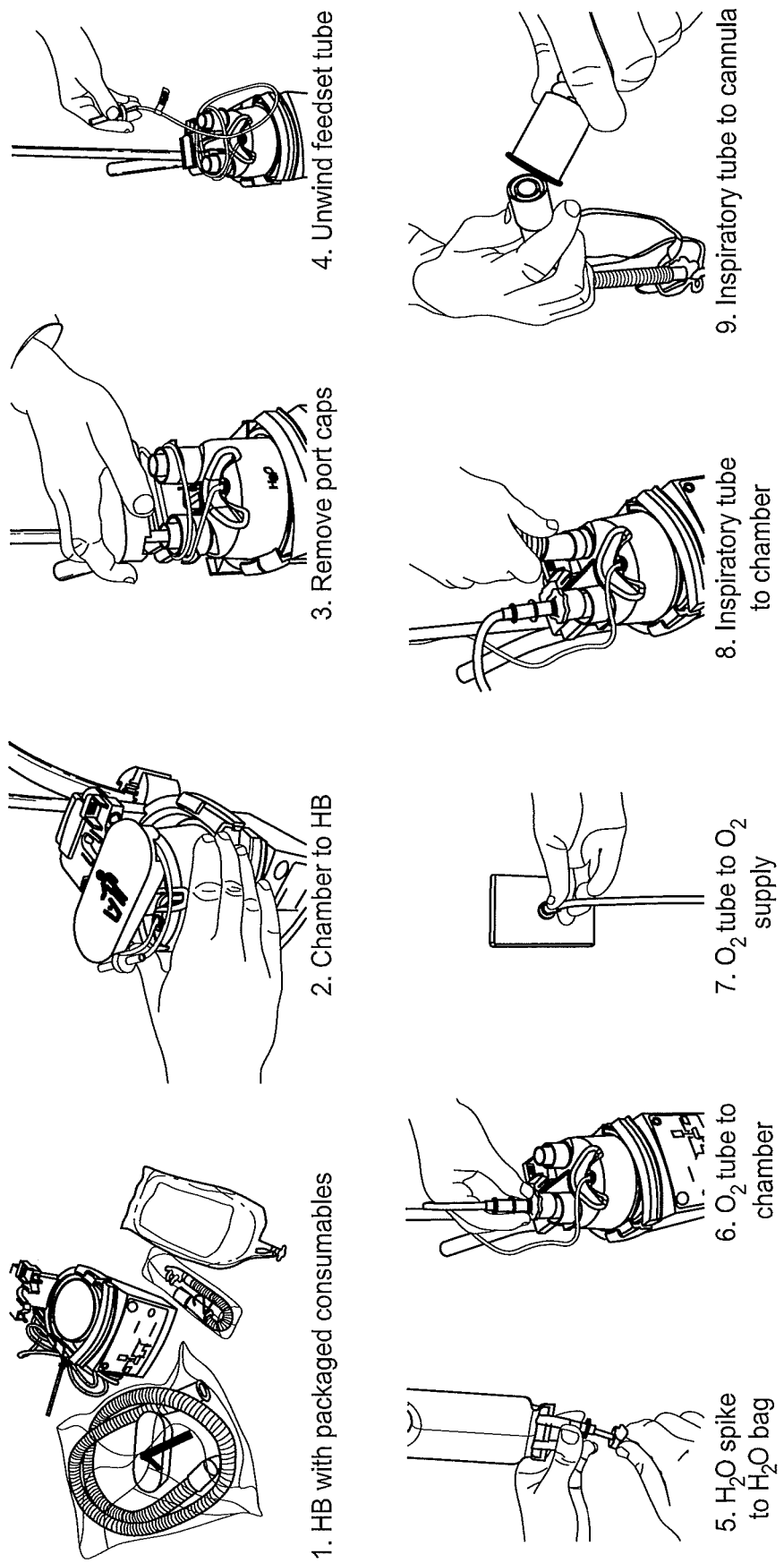
FIG. 10 illustrates a method for setting up a humidification system.

Additional features can assist the operator with the overall set-up process. For example, packaging for the consumable components of the system 100 can include a schematic diagram illustrating the set-up procedure and/or step-by-step instructions. FIG. 10 illustrates a sequential method for setting up a humidification system 100. The method can include some or all of: installing the chamber 104 on the heater base 102, removing the port cap(s) 160, 170, removing the spike 164 from the winder 166, unwinding the liquid conduit 118 and removing the winder 166 from the chamber 104, coupling the spike 164 to a liquid source, coupling the supply conduit 120 to the chamber inlet 110, coupling the supply conduit 120 to the gases supply 130, coupling the inspiratory conduit 122 to the chamber outlet 112, and coupling the inspiratory conduit 122 to the Y-piece 127 or interface 126. The method can further include coupling the expiratory conduit 124 to the interface 126 or the Y-piece 127 and the gases supply 130.

Figure 12:
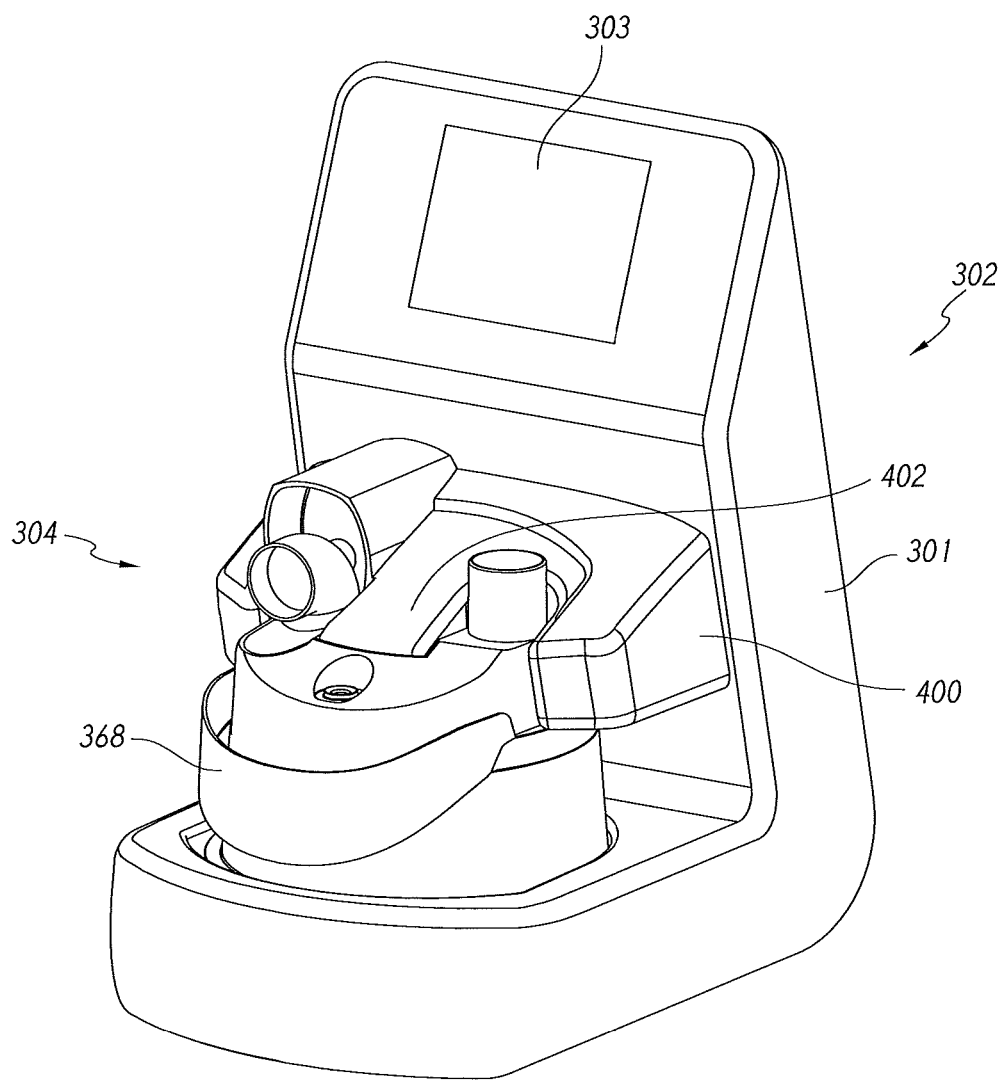
FIG. 12 illustrates a chamber installed on a heater base having a sensor cartridge.

Another example embodiment of a humidification chamber 304 installed on a heater base 302 having a sensor cartridge module 400 is shown in FIG. 12. The heater base 302, sensor cartridge module 400, and/or chamber 304 can include any of the features shown and described herein with respect to other embodiments.

Like the heater base display 103 of FIG. 11, the heater base display 303 of the heater base 302 shown in FIG. 12 can be located on an upper surface of the spine 301 for easier viewing. The upper surface of the spine 301 and therefore the display 303 can also be oriented at an angle as shown to allow for an improved or easier view of the display 303. In some embodiments, the upper surface and/or display 303 can be oriented at an angle of about 22° from vertical, although other angles are also possible. In some embodiments, the display 303 or one or more portions of the display can be touchscreen. The display 303 can include touchscreen portions in combination with physical buttons, knobs, and/or the like. Touchscreen portions can advantageously provide greater user interaction possibilities than physical buttons and knobs alone. In some embodiments, the display 303 can include any of the features described in U.S. Provisional Application No. 61/893,758, filed Oct. 21, 2013, the entirety of which is hereby incorporated by reference herein.

Figure 13A:
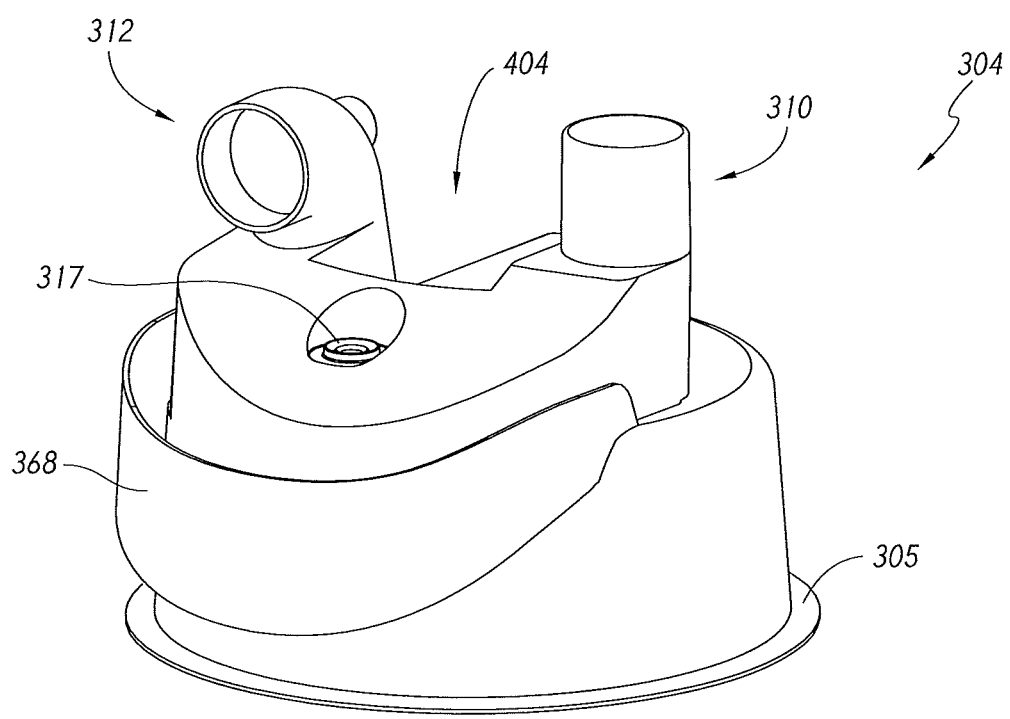
FIGS. 13A-13B illustrate the chamber of FIG. 12.
Figure 13B:
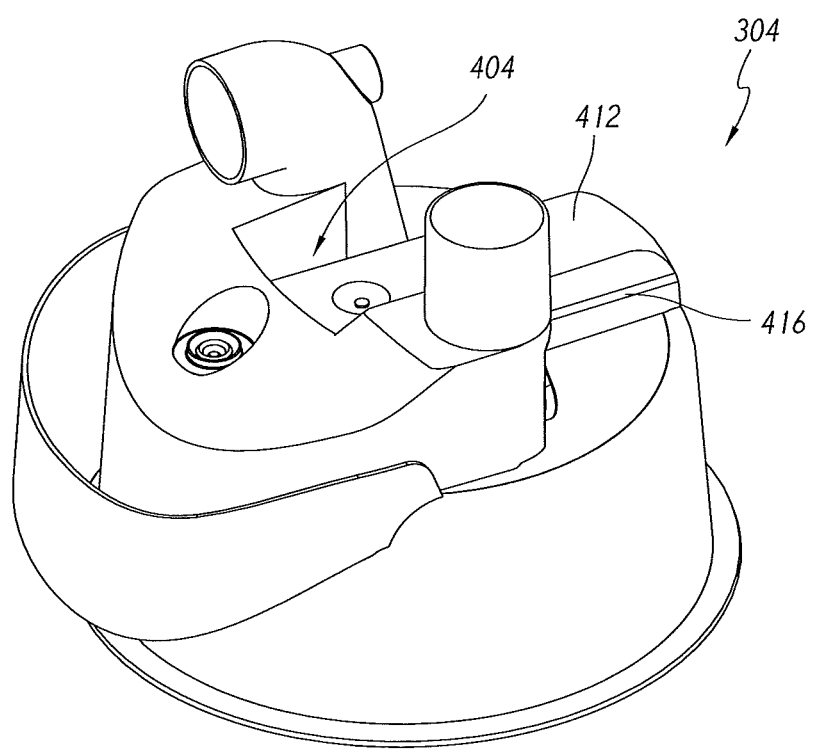

Similar to humidification chamber 104, humidification chamber 304 includes a protruding portion 305, an inlet 310, an outlet 312, and a liquid inlet 317, as shown in FIGS. 13A-13B. As shown, the liquid inlet 317 can be positioned near a front of the chamber 304. The liquid conduit 118 can extend from the liquid inlet 317 and can be secured in the liquid inlet 317 with an adhesive such as glue or any other suitable technique. This placement places the liquid conduit 118 farther from the heater base display 303, which can advantageously reduce possible obstruction of or interference with the display 303 by the liquid conduit 118. This can be particularly advantageous if the display 303 is a touch screen display such that contact by the liquid conduit 118 could be interpreted as a display input. Placement near the front of the chamber 304 can also help prevent or inhibit the liquid conduit 118 from being caught between the heater base 302 and chamber 304 when the chamber 304 is installed on the heater base 302. In the illustrated embodiment, the inlet 310 extends upward from the chamber 304, and the outlet 312 has an elbow shape such that the outlet 312 extends upward then bends to extend toward the front of the chamber 304. In other words, the outlet 312 extends away from the heater base 302 when the chamber 304 is installed on the heater base 302. In the illustrated embodiment, the outlet 312 bends to an angle of about 90°.

Figure 14A:
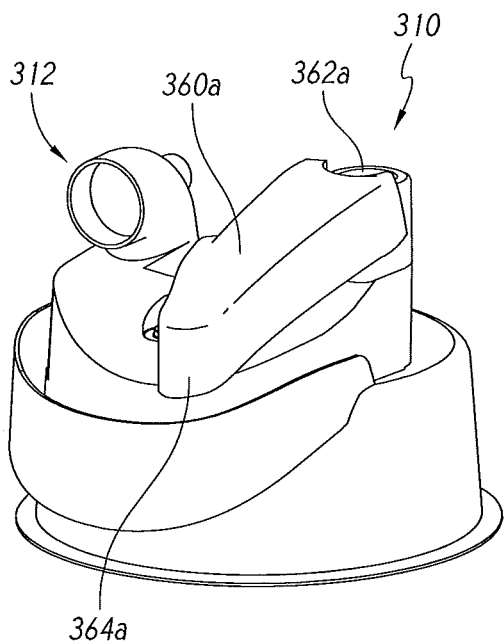
FIGS. 14A-14F illustrate various views of a port cap installed on the chamber of FIGS. 12-13B.
Figure 14B:
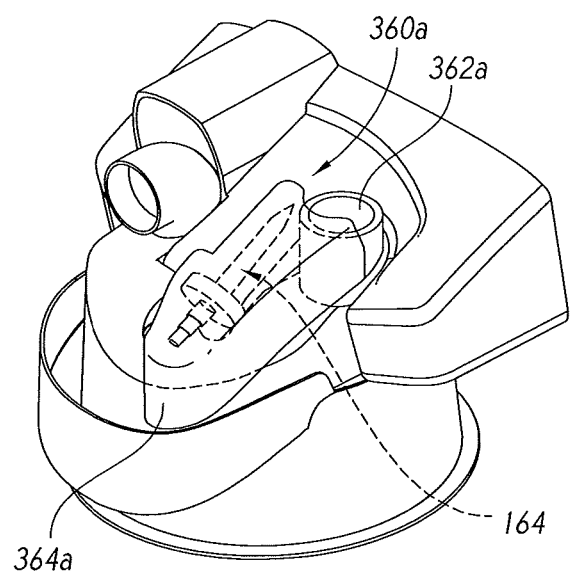
Figure 14C:
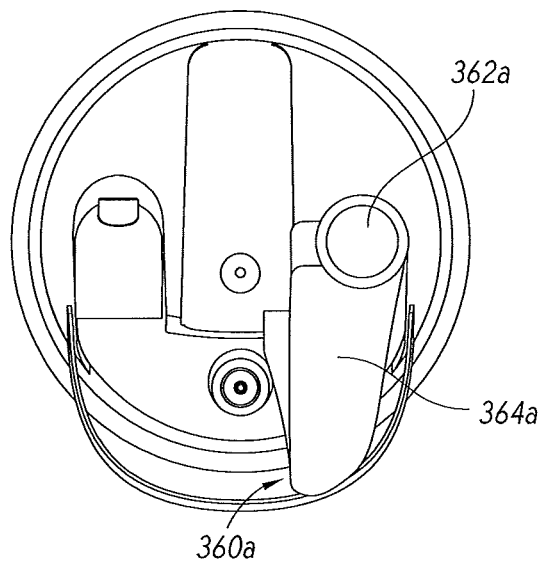
Figure 14D:
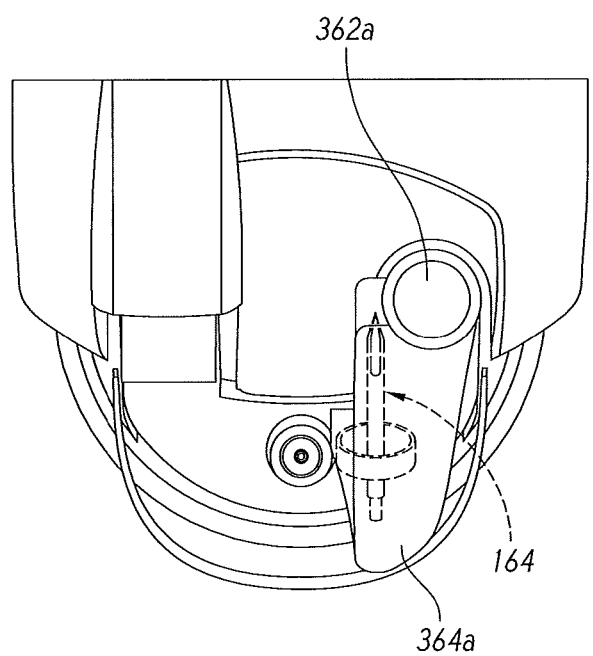
Figure 14E:
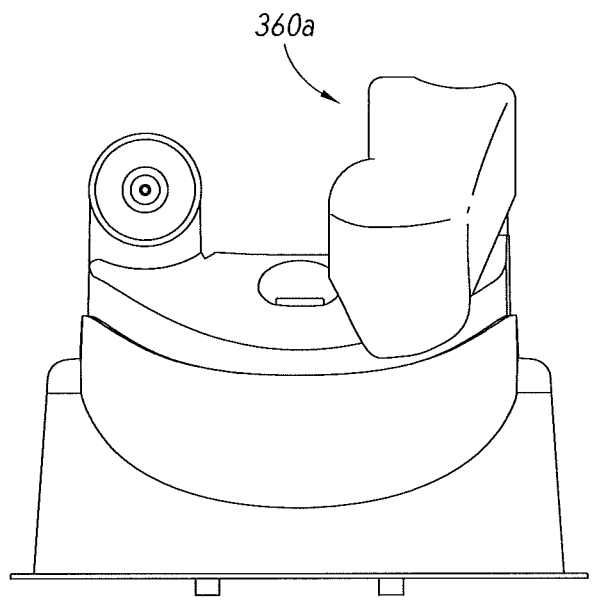
Figure 14F:
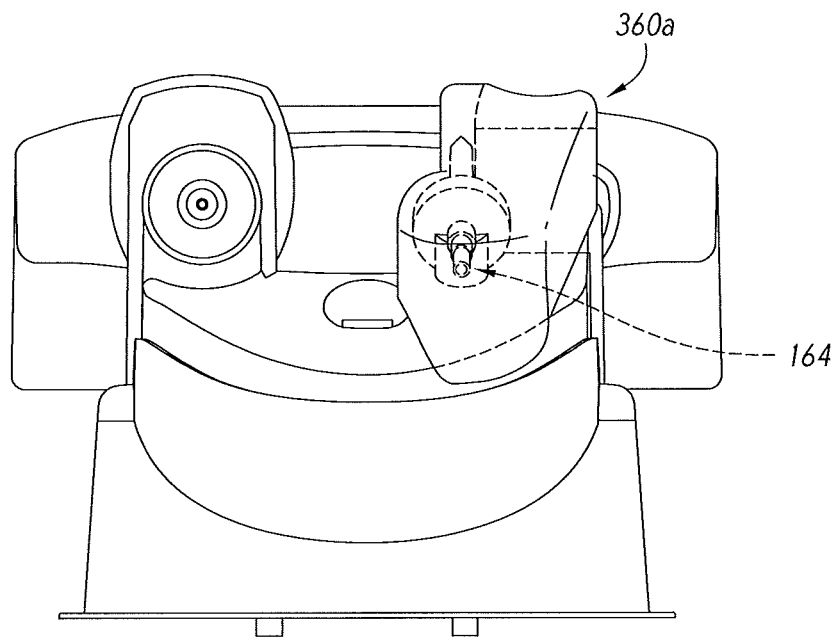
Figure 14G:
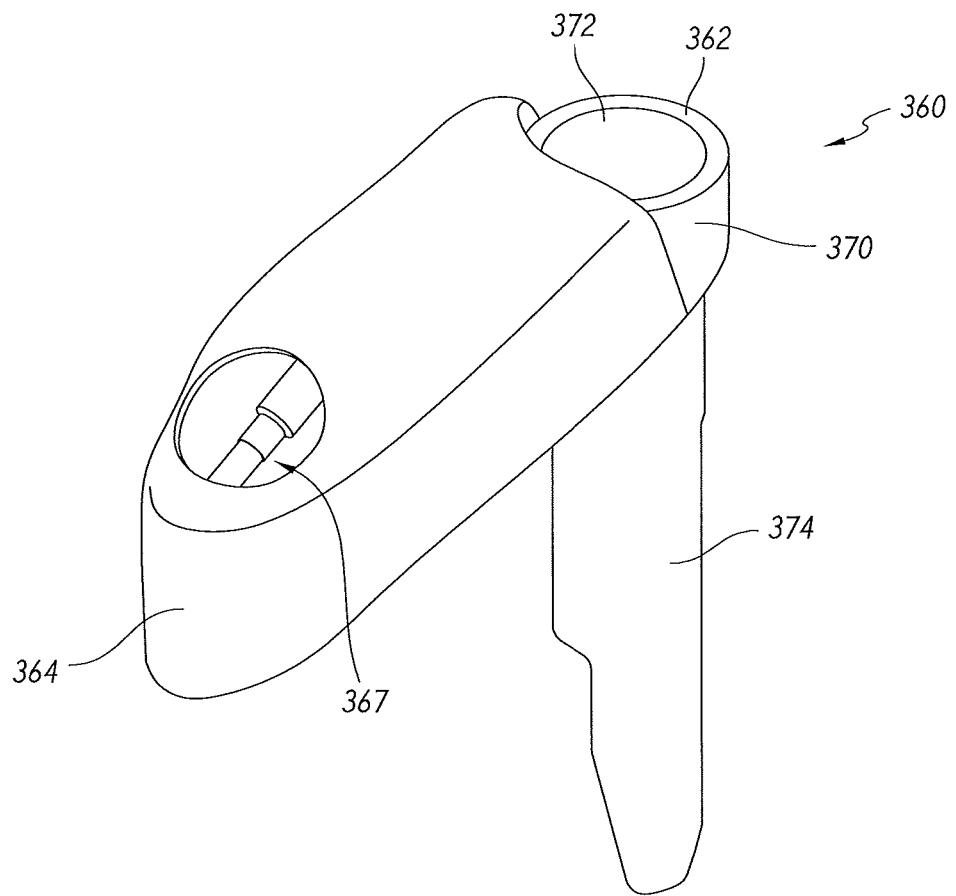
FIGS. 14G-14H illustrate a port cap.
Figure 14H:
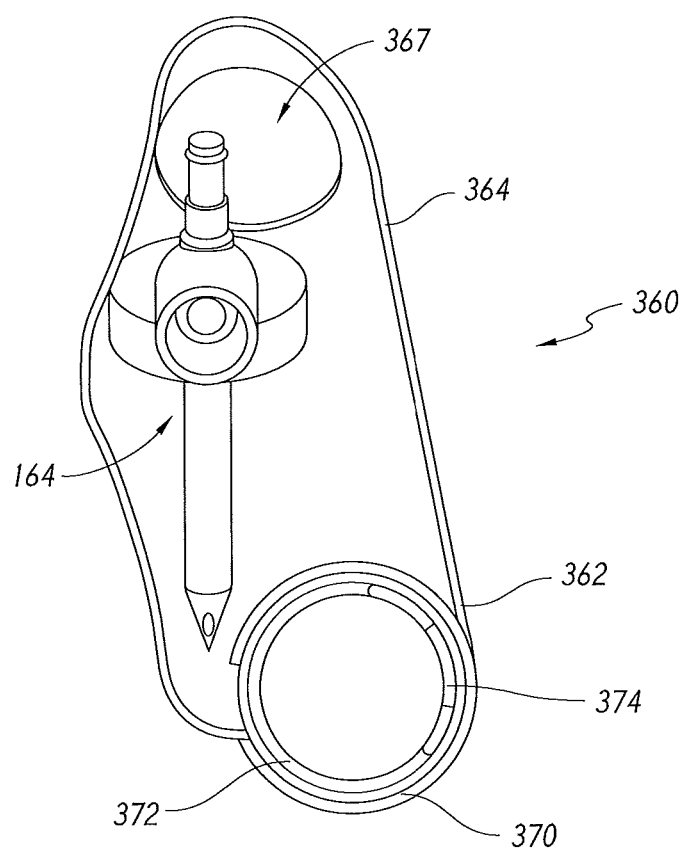
Figure 141:
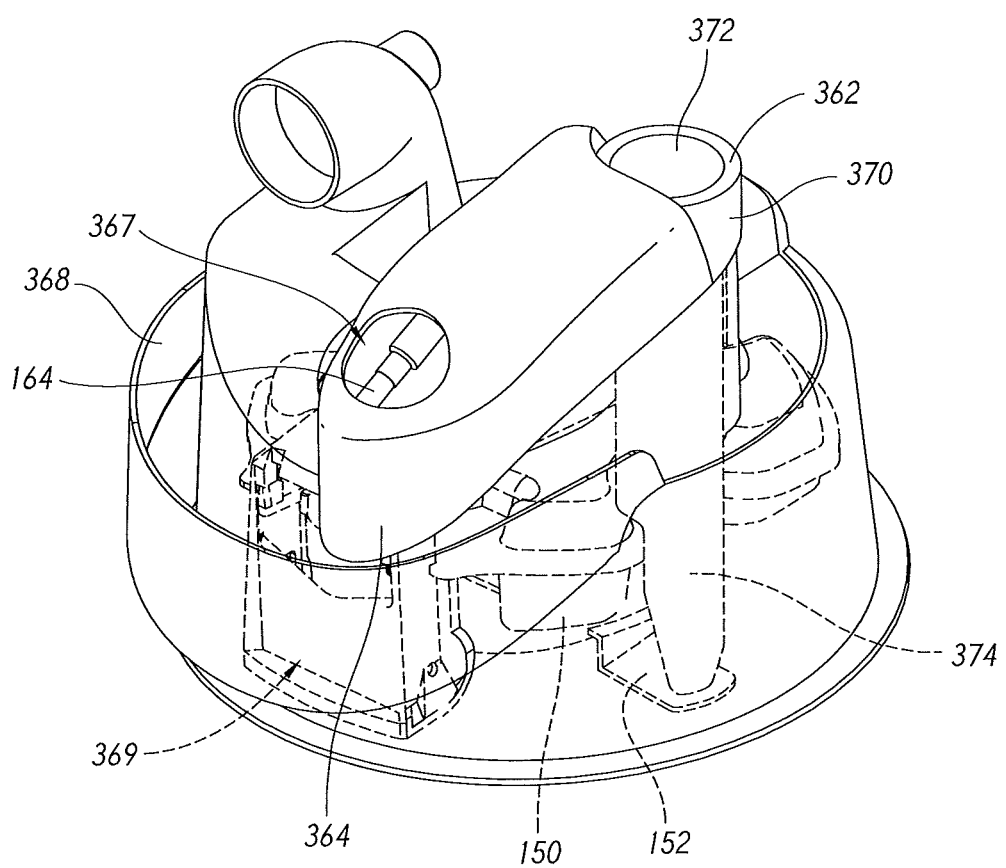
Figure 14J:
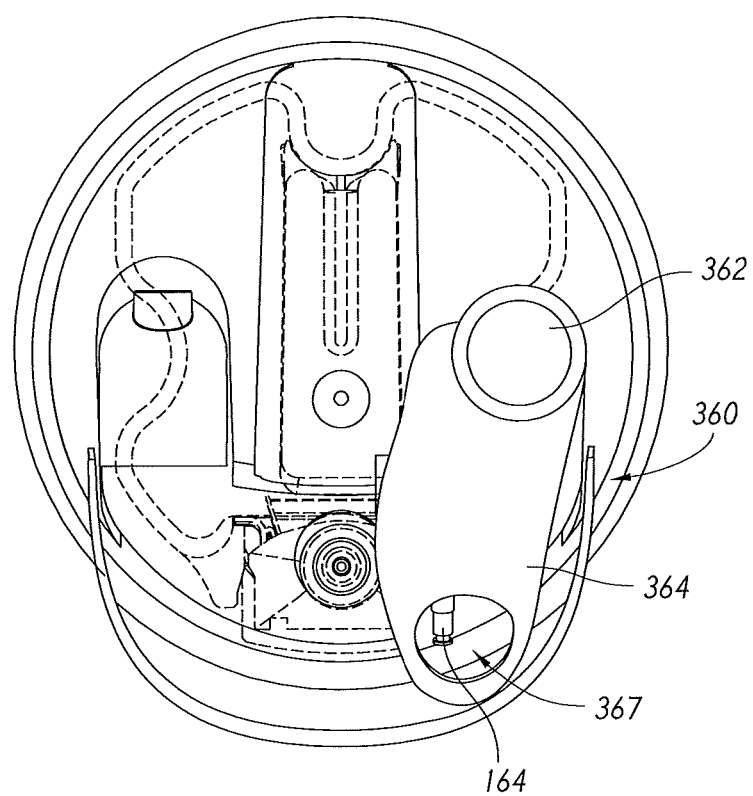
Figure 14K:
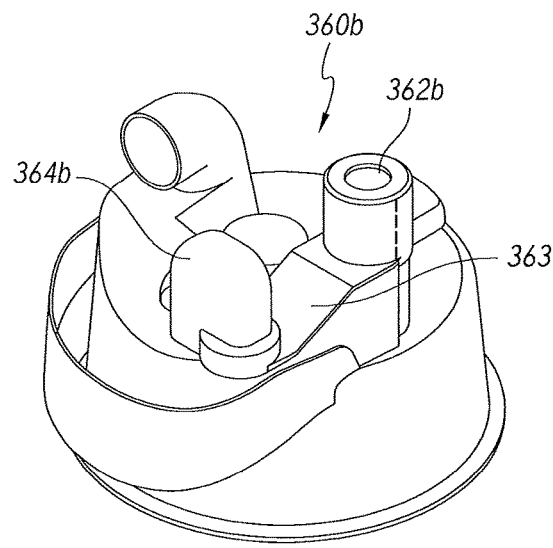
FIGS. 14K-14P illustrate a port cap installed on the chamber of FIGS. 12-13B.
Figure 14L:
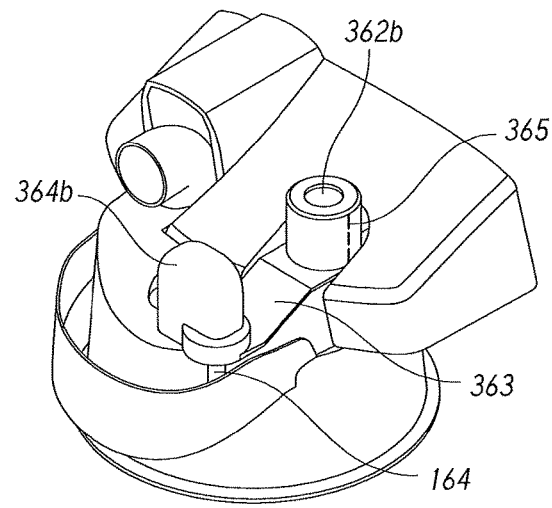
Figure 14M:
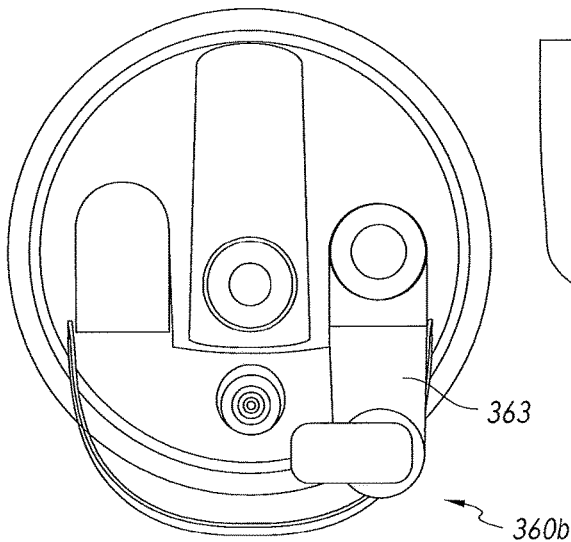
Figure 14N:
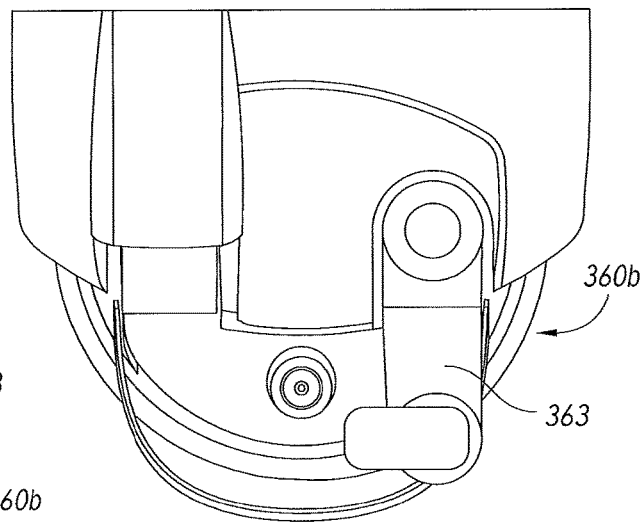
Figure 14O:
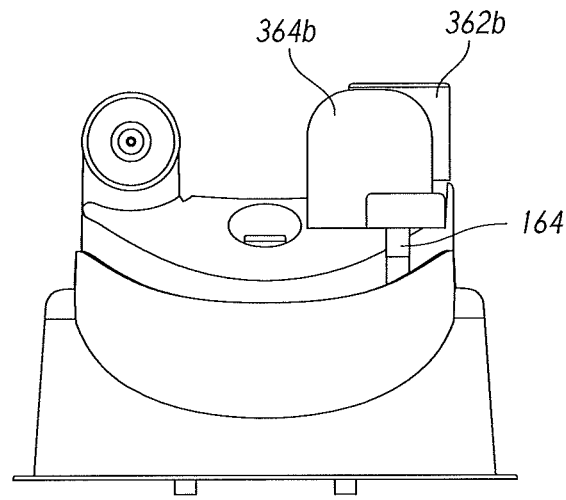
Figure 14P:
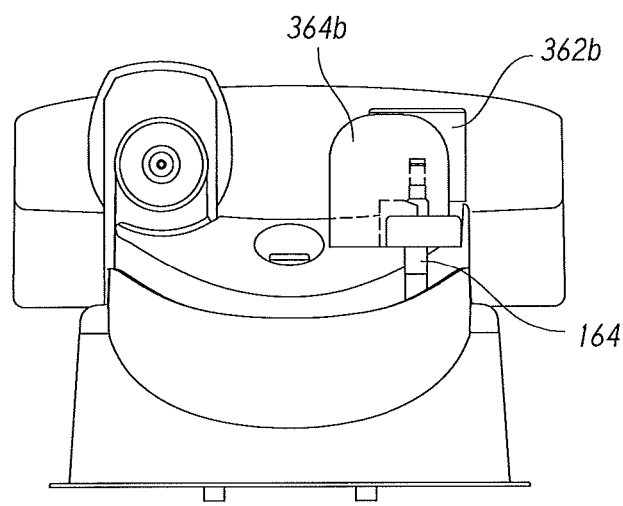

In some embodiments, the chamber 104 can be packaged with a single port cap 360, 360a, 360b having a single float-retaining leg, for example as shown in FIGS. 14A-14P. In the illustrated embodiments, the port cap 360 is configured to cover the inlet 110, and the float-retaining leg extends into the inlet 310 to restrain the float(s). As shown, the port cap 360 can also cover the spike 164. Covering the spike 164 with the port cap 360 can advantageously encourage the user to remove the port cap 360 before use, thereby freeing the float(s). Positioning the spike 164 under the port cap 360 also prevents or inhibits the user from being able to connect the spike 164 to a water bag before the float-retaining leg has been removed from the inlet 310 to free the float(s) so that the float(s) can function to, for example, prevent or inhibit overfill.

Use of a single port cap 360 can advantageously allow for the outlet 312 to have an elbow configuration as compared to capping both the inlet 310 and outlet 312 ports. In some embodiments, the chamber 304 is shipped and stored in a hygienic consumable package. Therefore, leaving the outlet 312 uncovered does not significantly increase the risk of contamination of the chamber 304 during shipping or storage. A single port cap 360 can also allow for the inspiratory conduit 122 to be preassembled with the chamber 304 if desired. In some embodiments, the inspiratory conduit 122 includes a connector configured to couple the conduit 122 to the outlet 312. For example, the connector and/or outlet 312 can include various features as described in U.S. Provisional Application No. 61/919,485, filed Dec. 20, 2013. The connector can be configured to clip onto the chamber 304, which can advantageously allow for the inspiratory conduit 122 and chamber 304 to be preassembled in the packaging for shipping and storage. This can advantageously reduce the number of connections the user is required to make.

In the embodiment of FIGS. 14A-14F, the port cap 360a includes a first portion 362a configured to cover the inlet 310 and a second portion 364a that extends forward from the first portion 362a and is configured to cover the spike 164 in a shipping position, as shown in FIGS. 14B, 14D, 14F. In some configurations, the spike 164 can be in a horizontal shipping position. A top surface of the first portion 362a can be downwardly offset from a top surface of the second portion 364a so that the top of the first portion 362a is at least substantially flush with the top of the inlet port 310. In the embodiment of FIGS. 14K-14P, the port cap 360b includes a first portion 362b configured to cover the inlet 310, a second portion 364b configured to cover the spike 164 in a vertical shipping position adjacent the front of the chamber 304 as shown in FIGS. 14L, 14N, and 14P, and a ramped intermediate portion 363 extending between and connecting the first portion 362b and the second portion 364b.

The second portion 364a, 364b of the port cap 360a, 360b can include features configured to retain the spike 164 when the port cap 360a, 360b is removed from the chamber 304, for example as shown in FIGS. 14G-14H. In some embodiments, the port cap 360a, 360b includes a hook, loop, hole or the like that a user can use to more easily remove the port cap 360a, 360b and/or to hang the port cap 360a, 360b containing the spike 164 on a medical stand until the user is ready to connect the spike 164 to a water bag. For example, FIGS. 14G-14J illustrate a port cap 360 that is generally similar to the port cap 360a of FIGS. 14A-14F but also includes a loop hole 367 in the second portion 364. The loop hole 367 can also allow the user to see a portion of the spike 164 so that the user is further prompted to remove the port cap 360 to access the spike 164. In the illustrated embodiment, the port cap 360 also includes a graphic, for example, a graphic of a person disposing of trash in a bin. This can advantageously indicate to the user that the port cap 360 is intended to be removed and discarded.

The port cap 360, 360a, 360b can be secured to the inlet 310 by friction between the two components. In some embodiments, for example as shown in FIGS. 14G-14J, the first portion 362, 362a, 362b of the port cap 360, 360a, 360b can include an outer ring 370 configured to at least partially encircle an outer perimeter of the inlet 310 and an inner ring 372 configured to at least partially encircle an inner perimeter of the inlet 310. In some embodiments, the port cap 360, 360a, 360b is secured to the inlet 310 by friction between an inner surface of the inlet 310 and an outer surface of, for example, the inner ring 372. In other embodiments, the port cap 360, 360a, 360b can be secured to the inlet 310 by friction between an inner surface of the outer ring 370 and an outer surface of the inlet 310. The first portion 362, 362a, 362b further includes the float-restraining leg 374. In some embodiments, the float-restraining leg 374 is formed integrally with and/or is a continuation of the inner ring 372. For shipping and storage, the port cap 362, 362a, 362b is coupled to the chamber 304 such that the leg 374 extends into the inlet 310 to engage a tab 152 extending from the float 150.

In some embodiments, the first portion 362b of the port cap 360b of FIGS. 14K-14P can include one or more tear strips 365, for example as shown in FIG. 14L. The first portion 362b can include a second tear strip 365 located on an opposite side of the first portion 362b from the tear strip 365 shown in FIG. 14L. In use, the user pulls up on the second portion 364b to begin removing the port cap 360b. The forces on the second portion 364b cause the intermediate portion 363 to begin to lift, which in turn applies an upward force to the first portion 362b. When the second portion 364b has been lifted a sufficient amount and/or a sufficient amount of force has been applied to the second portion 364b and transferred through the intermediate portion 363 to the first portion 362b, the first portion 362b begins to tear along the tear strip(s) 365. The first portion 362b therefore can open similar to a clamshell to allow the user to more easily remove the port cap 360b from the inlet 310.

The feedset or liquid conduit 118 can be wound into a looped configuration and secured with a label 218, for example as shown in FIGS. 4G and 4H and described in the accompanying disclosure herein. The end of liquid conduit 118 secured to the liquid inlet 117 and the end of the liquid conduit 118 secured to the spike 164 can extend from the looped portion in the same direction so that the label 218 can slide off of the liquid conduit 118 as the user is setting up the system. Alternatively, the ends of the liquid conduit 118 can extend from the looped portion in opposite directions, and the user can release the liquid conduit 118 from the looped configuration by tearing the label 218. In some embodiments, this can allow for easier and quicker set-up because removing the label 218 to release the liquid conduit 118 can be easier and quicker than unwinding the liquid conduit 118 from a winder.

In some embodiments, the chamber 304 includes a handle 368 in lieu of or in addition to grips 168. In some embodiments having an elbow shaped outlet 312, a conduit or conduit connector coupled to the outlet 312 will extend forward. This could make it more difficult for a user to grasp the grips 168. Therefore, the handle 368 can advantageously improve access to the chamber 304 and make it easier for the user to grasp the chamber 304 when the conduit is connected to the outlet 312. The handle 368 and/or grips 168 can advantageously allow the user to grasp the chamber 304 more easily during installation and/or removal of the chamber 304 from the base 302. The handle 368 and/or grips 168 can also allow the user to apply the force required to remove the chamber 304 from the base 302 more easily. The handle 368 and/or grips 168 are visually intuitive such that a user will typically understand the function of these features without requiring specific instructions. The handle 368 can also act as a brace, support, or pocket for the liquid conduit 118 during shipping and storage. For example, the handle 368 can provide a partially enclosed capture area and/or shelf 369 (shown in FIG. 14I) for the liquid conduit 118 during shipping and storage.

Figure 25:
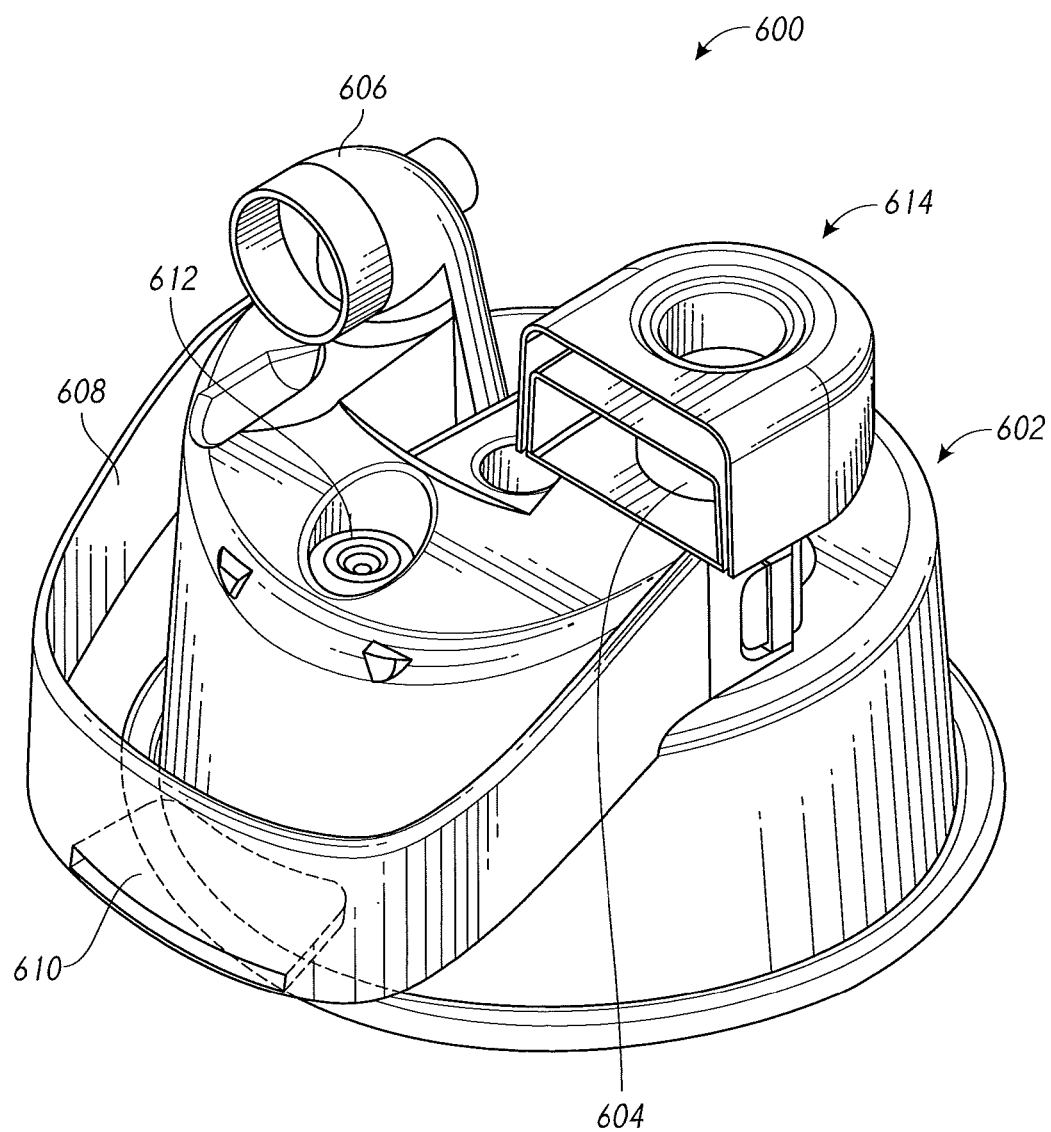
FIG. 25 illustrates a perspective view of a chamber assembly.

With reference now to FIG. 25, a further chamber assembly 600 is illustrated. The chamber assembly can include a chamber 602 that includes an inlet port 604 and an outlet port 606. In the illustrated configuration, the inlet port 604 extends generally vertically while the outlet port 606 extends generally horizontally or at some angle other than generally vertically. The chamber 602 also includes a handle 608. A shelf 610 can extend between a portion of the handle 608 and the body of the chamber 602. In some configurations, the shelf 610 may not be attached to one of the body of the chamber 602 and the handle 608. The chamber assembly 600 also includes a water fill port 612. In some configurations, the water fill port 612 is positioned between the handle 608 and the ports 604, 606. Other configurations are possible. The chamber assembly 600 can have any suitable configuration. In some configurations, components illustrated in FIG. 25 may be omitted, or may be removed and replaced by components from any of the above-described embodiments, or the like.

Figure 26:
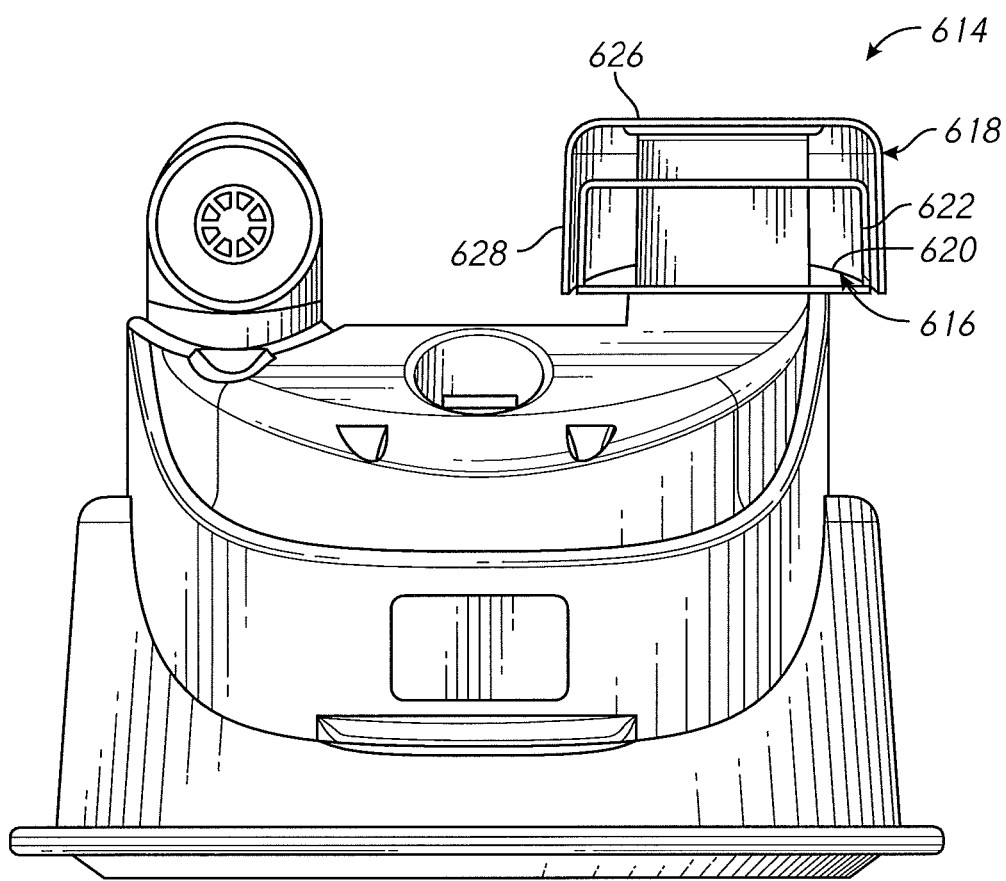
FIG. 26 illustrates a front elevation view of a chamber assembly.
Figure 31:
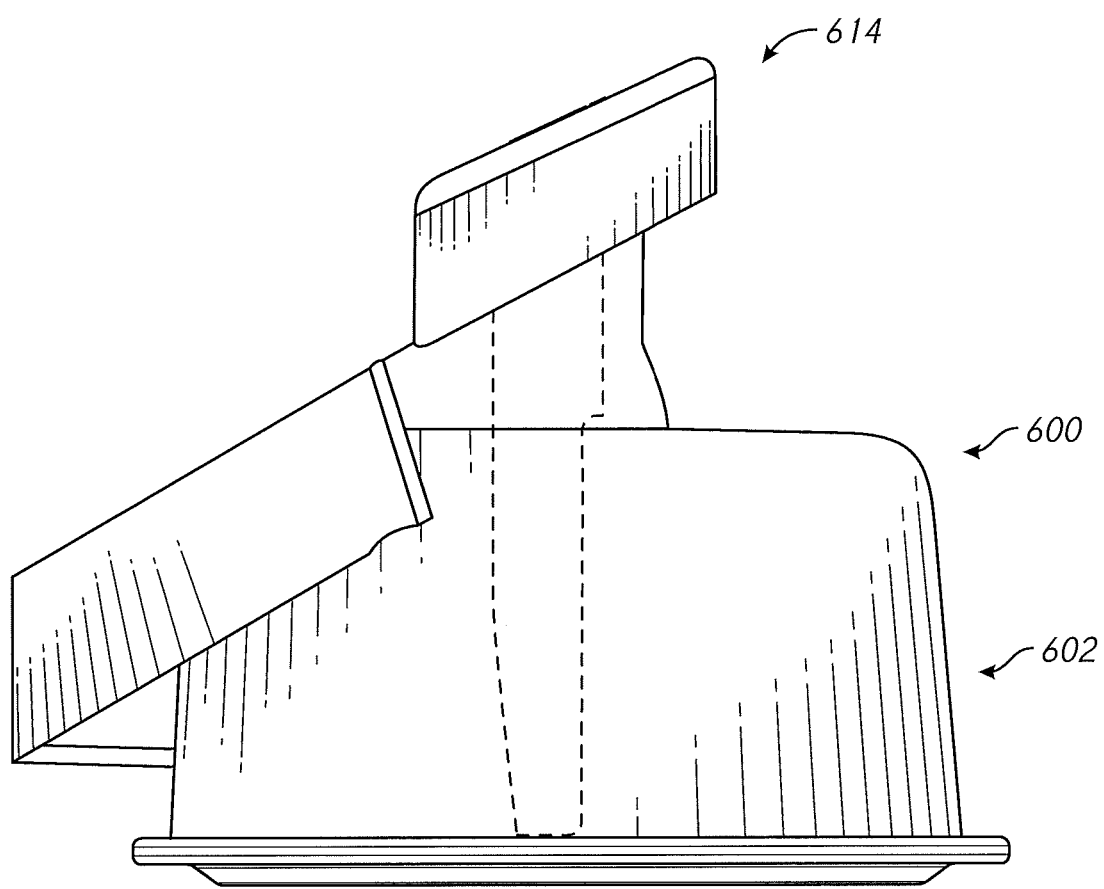
FIG. 31 illustrates another side elevation view of a chamber assembly with an alternative port cap.

In the illustrated configuration, a port cap 614 covers the inlet port 604 during shipping and storage, for example. FIG. 31 illustrates a varied industrial design for the port cap 614. With reference to FIG. 26, the port cap 614 can be a two piece configuration. The port cap 614 can include a collar 616 and a post 618. The collar 616 and the post 618 can be separable. The collar 616 can have a port encircling support 620. The support 620 can have any suitable configuration. In some configurations, the support 620 is a generally planar surface that includes an opening that is sized and configured to receive the inlet port 604.

A retainer 622 can extend upwardly from the support 620. The retainer 622 can define a forward-facing opening. In some configurations, the retainer 622 can be formed by a rectangular frame that is positioned generally forward of the inlet port 604. The retainer 622 and the support 620 can be integrally formed in some configurations.

The post 618 can be inserted into the inlet port 604. The post 618 can include a lid 626. The lid 626 can overlie at least a portion of the inlet port 604. The lid 626 can overlie at least a portion of the collar 616. In some configurations, the lid 626 can overlie the entire collar 616. In some configurations, the lid 626 can include a downwardly extending flange 628. The flange 628 can generally enshroud three sides of the collar 616. In some configurations, the flange 628 is slightly spaced from the retainer 622.

Figure 28:
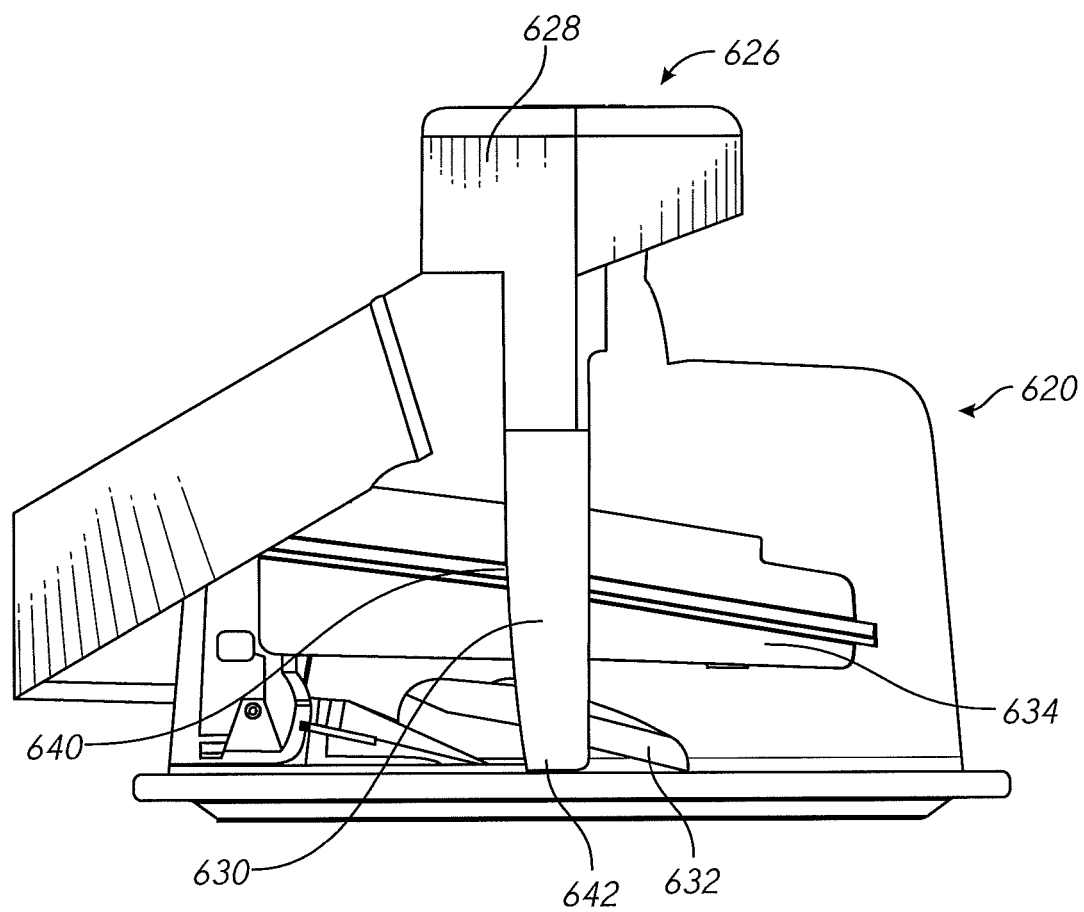
FIG. 28 illustrates a side elevation view of a chamber assembly with the internal components shown.

With reference to FIG. 28, the post 618 of the port cap 614 also can include a finger 630. The finger 630 can be integrally formed with the lid 626. The finger 630 is configured to be received inside of the chamber 602. The chamber 602 can include one or more float 632, 634. The floats 632, 634 control operation of a valve that, in turn, controls admission of fluid into the chamber 602 through the water delivery conduit 624. Further description of the float system can be found in U.S. Provisional Application No. 61/873,777, filed on Sep. 4, 2013 and U.S. Provisional Application No. 61/870,156, filed on Aug. 26, 2013, each of which is hereby incorporated by reference in its entirety.

Figure 29:
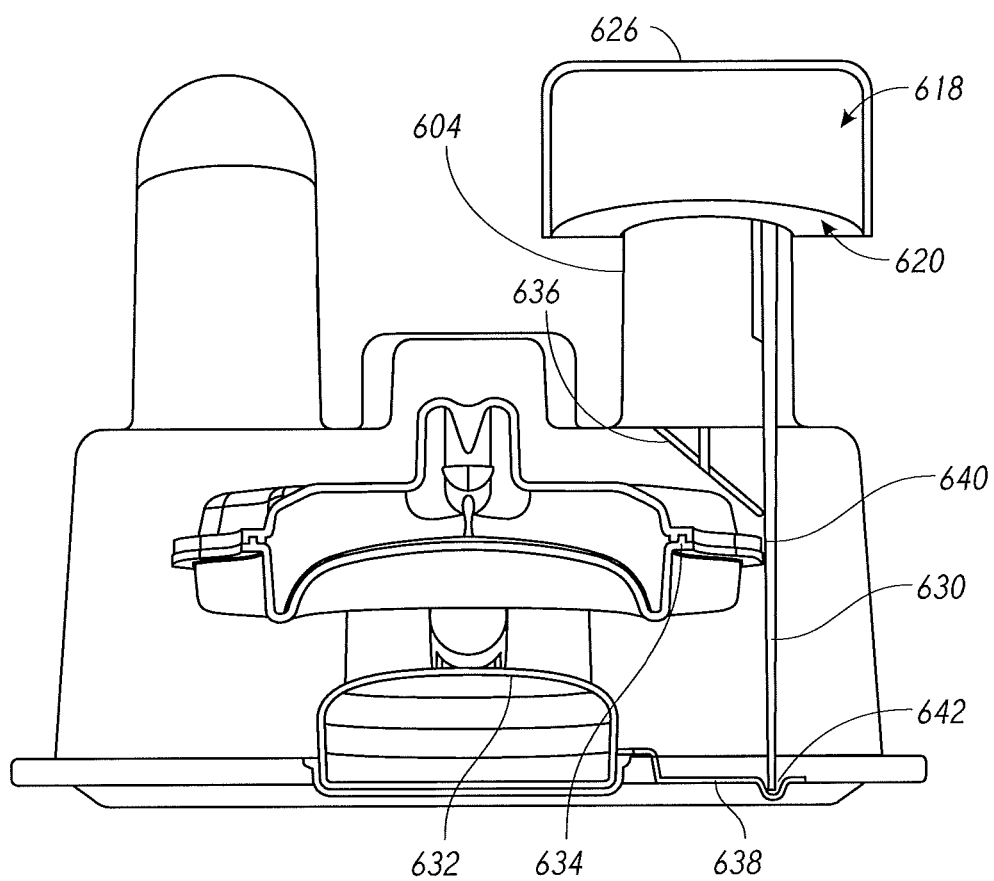
FIG. 29 illustrates a front elevation view of a chamber assembly.

With reference to FIG. 29, the inlet port 604 of the chamber 602 can include one or more internal structures 636. The one or more internal structures 636 can be used to address flow or splashing within the flow passing through the inlet port 604. In the illustrated configuration, the one or more internal structures 636 can be a baffle. The baffle 636 extends at least partially below the inlet port 604.

The finger 630 is configured to extend through the inlet port 604 and beyond the one or more internal structures 636. The finger 630 can have a portion above the structures 636 and a portion below the internal structures 636. The finger 630 can be connected to the lid 626 at a location generally vertically higher than the internal structures 636 and the finger 630 can contact at least one of the floats 632, 634 at a position vertically lower than the internal structures 636.

In the illustrated configuration, the finger 630 can include a first contact structure 640 and a second contact structure 642. The first contact structure 640 can be positioned between the second contact structure 642 and the lid 626. The first contact structure 640 can contact the primary float 634 while the second contact surface 642 can contact the secondary float 632. The secondary float 632 can include the control tab 638 and the second contact surface 642 can contact the control tab 638. A similar configuration also can be used with the primary float 634 and the first contact structure 640.

Figure 27:
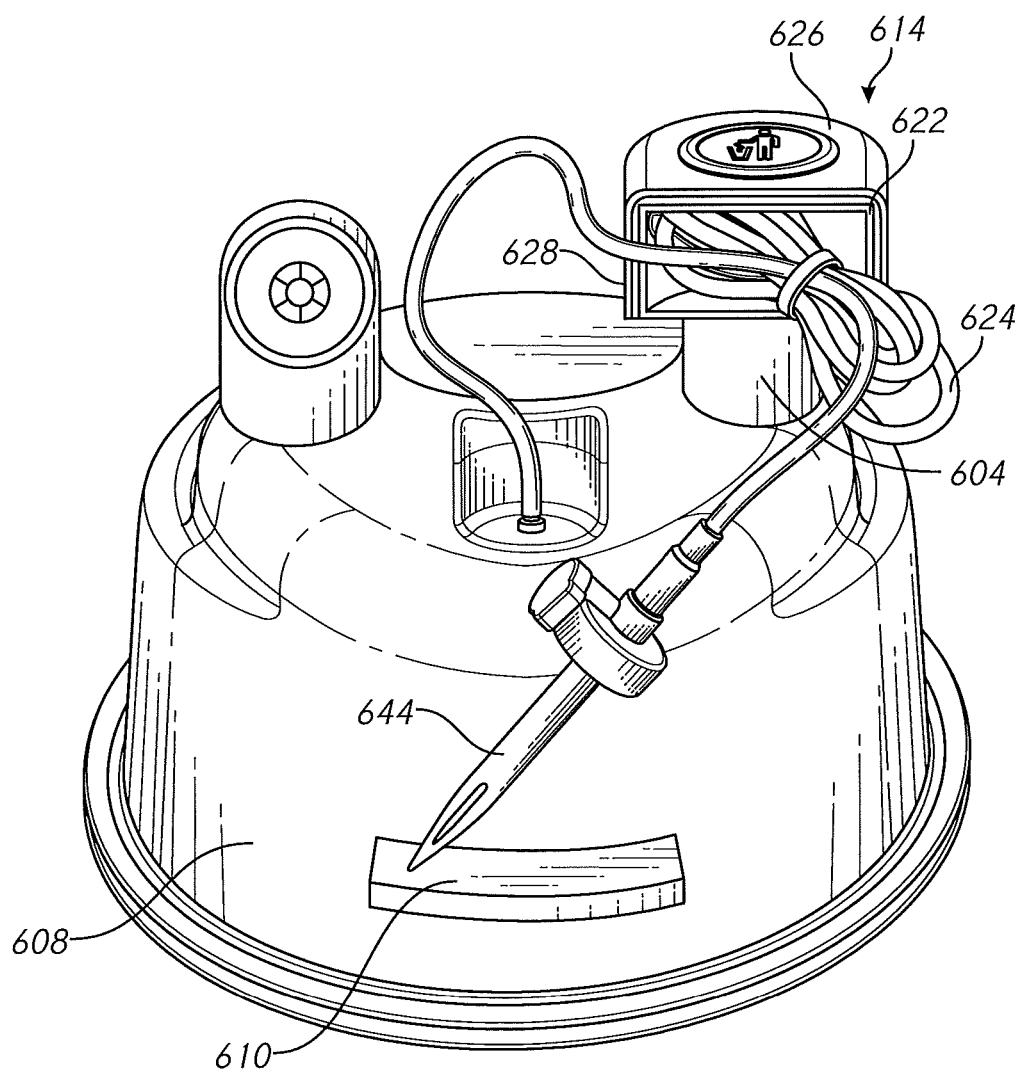
FIG. 27 illustrates a front elevation view of a chamber assembly with a feedset attached.

As shown in FIG. 27, a water delivery conduit 624 can be wrapped about the inlet port 604. The wrapped water delivery conduit 624 can be inserted into the port cap 614 through the forward facing opening defined by the retainer 622. The wrapped water delivery conduit 624 can be positioned such that the inlet port 604 extends through the loop with the support 620 underlying the loop. The post 618 can be inserted into the port 604 with the finger 630 extending beyond the baffle 636. The finger 630 can hold the secondary float 632 and the primary float 634 in such a position that the valve that controls the flow of water into the chamber is open. The finger 630 can be secured in position by friction forces between the post 618 and the inlet port 604. The lid 626 and the flange 628 generally enclose the wrapped water delivery conduit 624. As shown in FIG. 27, a spike 644 can be connected to the water delivery conduit 624. The spike 644 can be housed between the handle 608 and the chamber 602. In some configurations, the spike 644 can be supported by the shelf 610 that is positioned within at least a portion of a gap defined between the handle 608.

Figure 30:
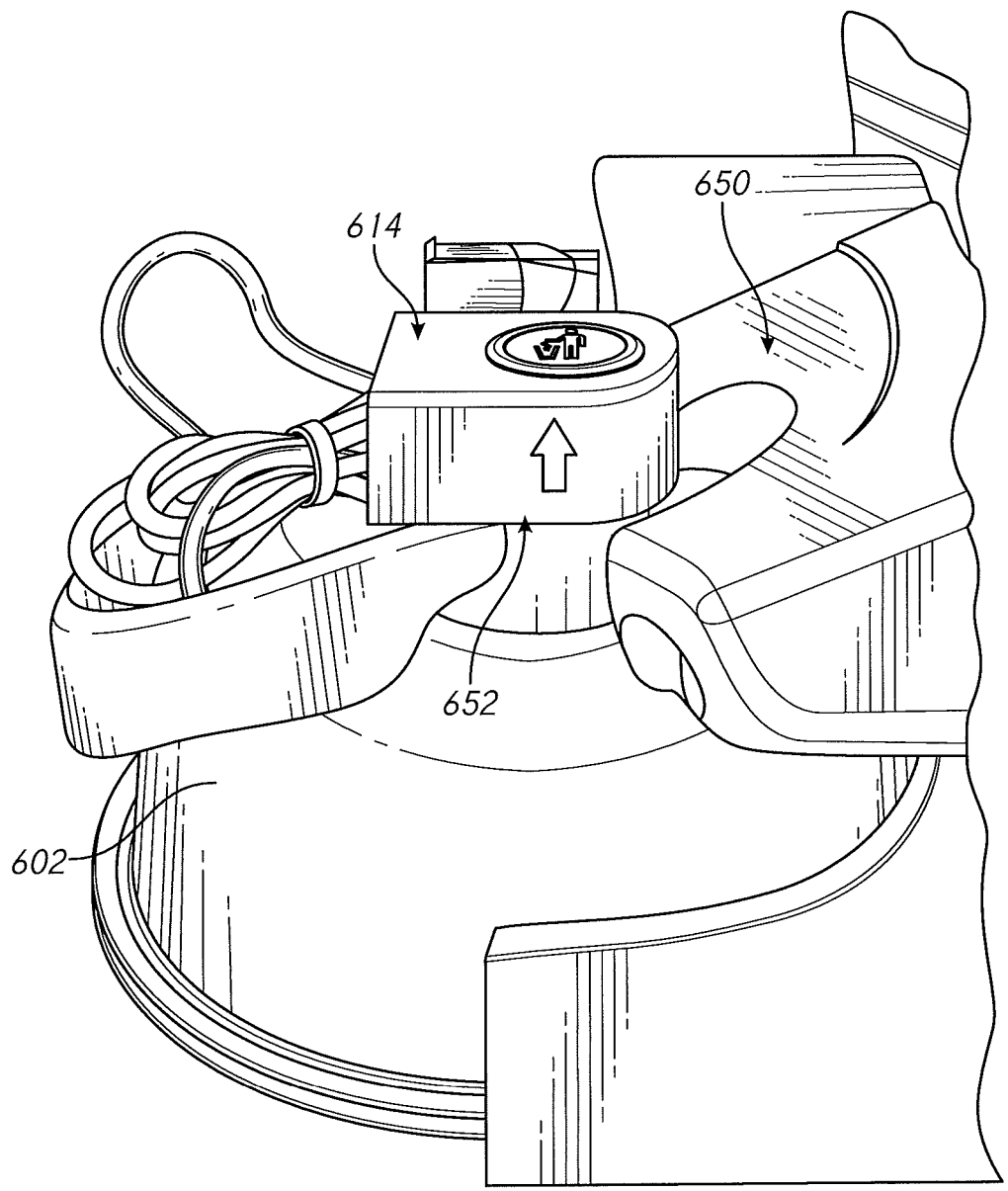
FIG. 30 illustrates an enlarged side perspective view of a chamber assembly showing a port cap being removed during insertion.

With reference now to FIG. 30, during insertion of the chamber 602 into the heater base, at least a portion of the port cap 614 can be lifted from the chamber 602. In the illustrated configuration, the heater base can include a lifting surface 650. The lifting surface 650 can contact a contact surface 652 of the port cap 614 during insertion of the chamber 602 into the heater base. In some configurations, the contact surface 652 is a portion of the post 618. In some configurations, the contact surface 652 is a portion of the flange 628. In some configurations, the contact surface 652 is a lower edge of the flange 628. In some configurations, the contact surface 652 is a portion of the collar 616. In some configurations, the contact surface 652 is a lower surface of the collar 616.

As the chamber 602 is docked into position, the lifting of the post 618 releases the floats 632, 634. In addition, the lifting of the post 618 reveals the coiled fluid delivery conduit 624. In addition, because the post 618 includes the finger 630 and because the coiled delivery conduit 624 wraps around the finger 630, removal of the finger 630 enables removal of the conduit 624. For at least these reasons, the connection of the spike 644 to a fluid source prior to releasing of the floats 632, 634 is unlikely. Thus, overfilling of the chamber 602 is less likely with the illustrated port cap 614.

With reference to FIGS. 32-37, an additional chamber assembly 700 is illustrated. The chamber assembly can include a chamber 702 that includes an inlet port 704 and an outlet port 706. In the illustrated configuration, the inlet port 704 extends generally vertically while the outlet port 706 extends generally horizontally or at some angle other than generally vertically. The chamber 702 also includes a handle 708. A shelf 710 can extend between a portion of the handle 708 and the body of the chamber 702. In some configurations, the shelf 710 may not be attached to one of the body of the chamber 702 and the handle 708. The chamber assembly 700 also includes a water fill port 712. In some configurations, the water fill port 712 is positioned between the handle 708 and the ports 704, 706. Other configurations are possible. The chamber assembly 700 can have any suitable configuration. In some configurations, components illustrated in FIG. 32 may be omitted, or may be removed and replaced by components from any of the above-described embodiments, or the like. For example, although the example embodiment of FIG. 32 includes a handle 708 and shelf 710, the chamber assembly 700 need not include the handle 708 or shelf 710.

Figure 35:
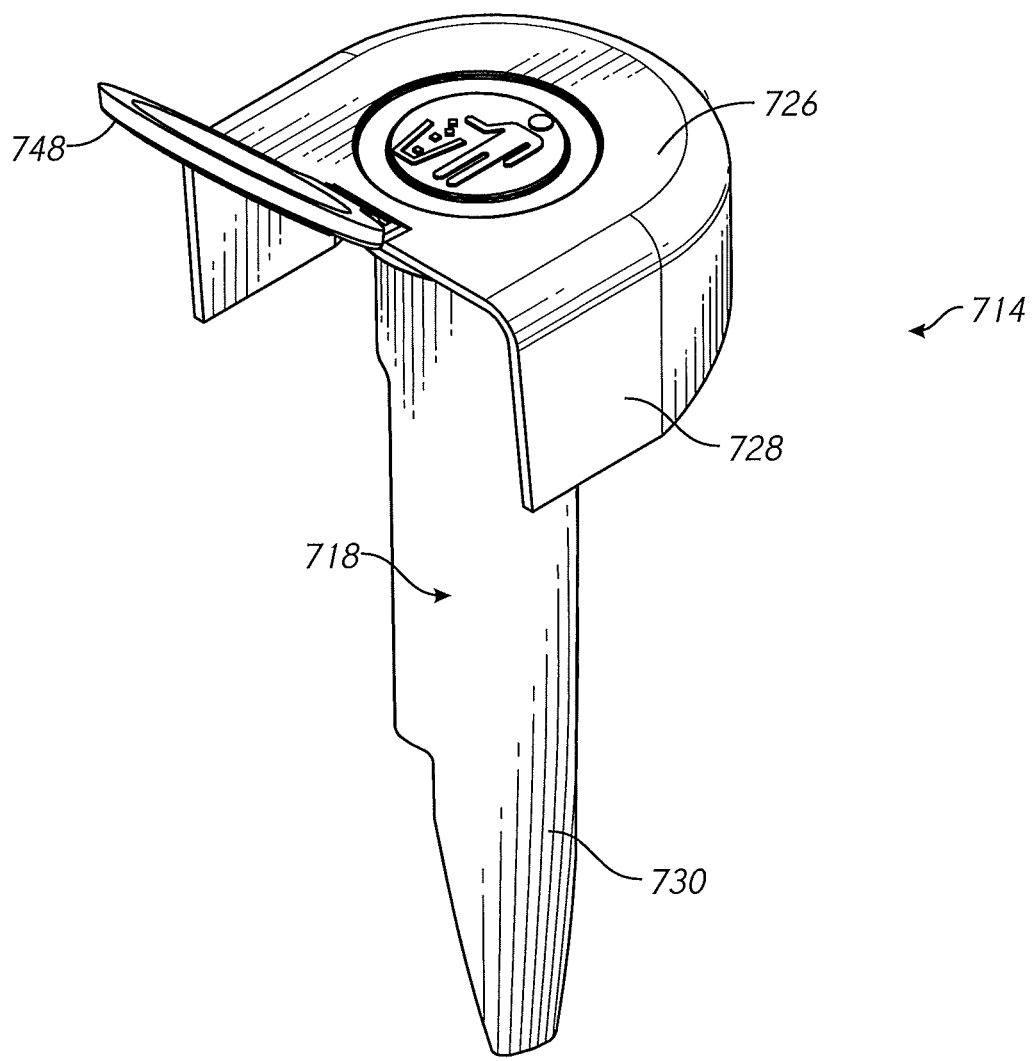
FIG. 35 illustrates a perspective view of a portion of a port cap.
Figure 36:
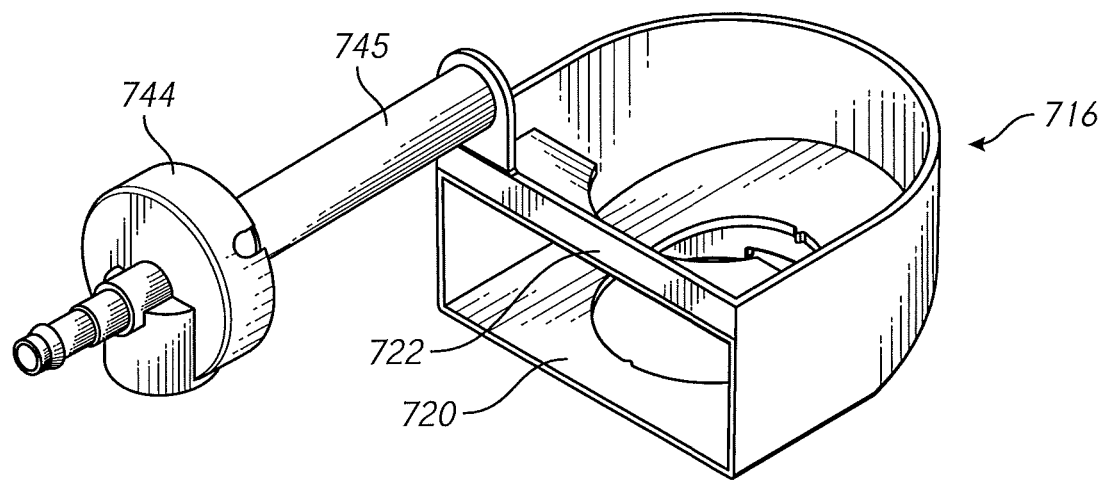
FIGS. 36 and 37 illustrate perspective views of a portion of a port cap.
Figure 37:
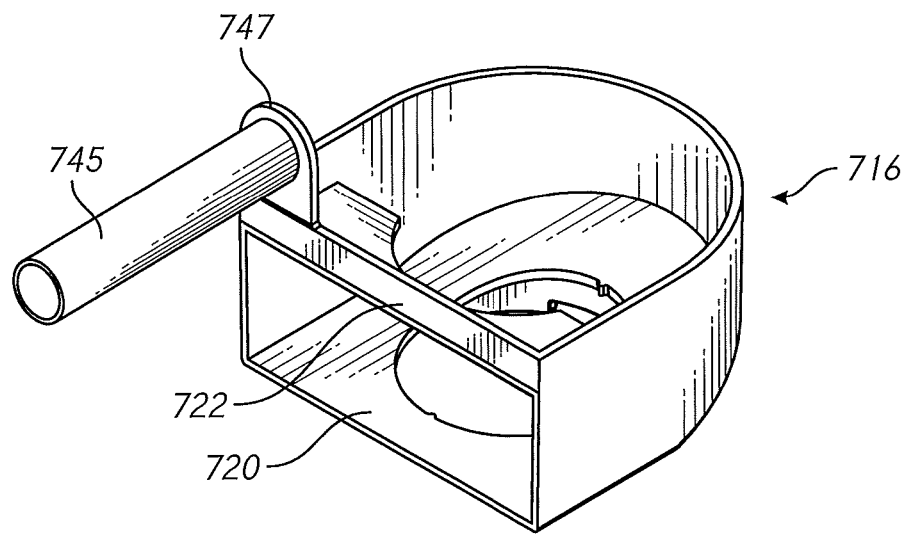

In the illustrated configuration, a port cap 14 covers the inlet port 704 during shipping and storage, for example. With reference to FIGS. 35-37, the port cap 714 can be a two piece configuration. The port cap 714 can include a collar 716 and a post 718. The collar 716 and the post 718 can be separable. The collar 716 can have a port encircling support 720. The support 720 can have any suitable configuration. In some configurations, the support 720 is a generally planar surface that includes an opening that is sized and configured to receive the inlet port 704.

A retainer 722 can extend upwardly from the support 720. The retainer 722 can define a forward-facing opening. In some configurations, the retainer 722 can be formed by a rectangular frame that is positioned generally forward of the opening for the inlet port 704. The retainer 722 and the support 720 can be integrally formed in some configurations.

The post 718 can be inserted into the inlet port 704. The post 718 can include a lid 726. The lid 726 can overlie at least a portion of the inlet port 704. The lid 726 can overlie at least a portion of the collar 716. In some configurations, the lid 726 can overlie the entire collar 716. In some configurations, the lid 726 can include a downwardly extending flange 728. The flange 728 can generally enshroud three sides of the collar 716. In some configurations, the flange 728 is slightly spaced from the retainer 722.

With reference to FIG. 35, the post 718 of the port cap 714 also can include a finger 730. The finger 730 can be integrally formed with the lid 726. The finger 730 is configured to be received inside of the chamber 702 and can be used to secure one or more floats in position in a similar manner to or the same as that described above.

Figure 32:
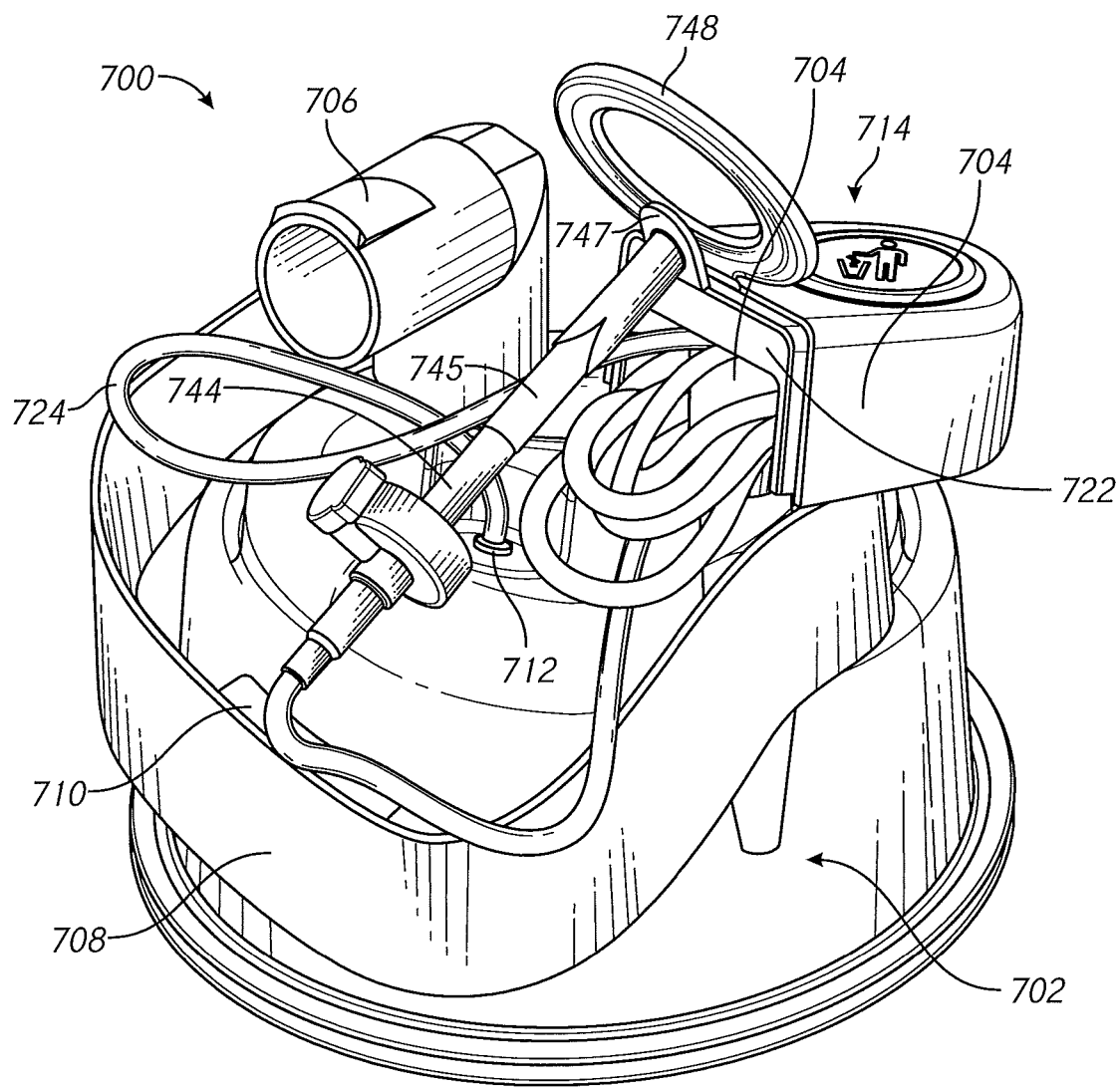
FIG. 32 illustrates a perspective view of a chamber assembly with a feedset attached.
Figure 33:
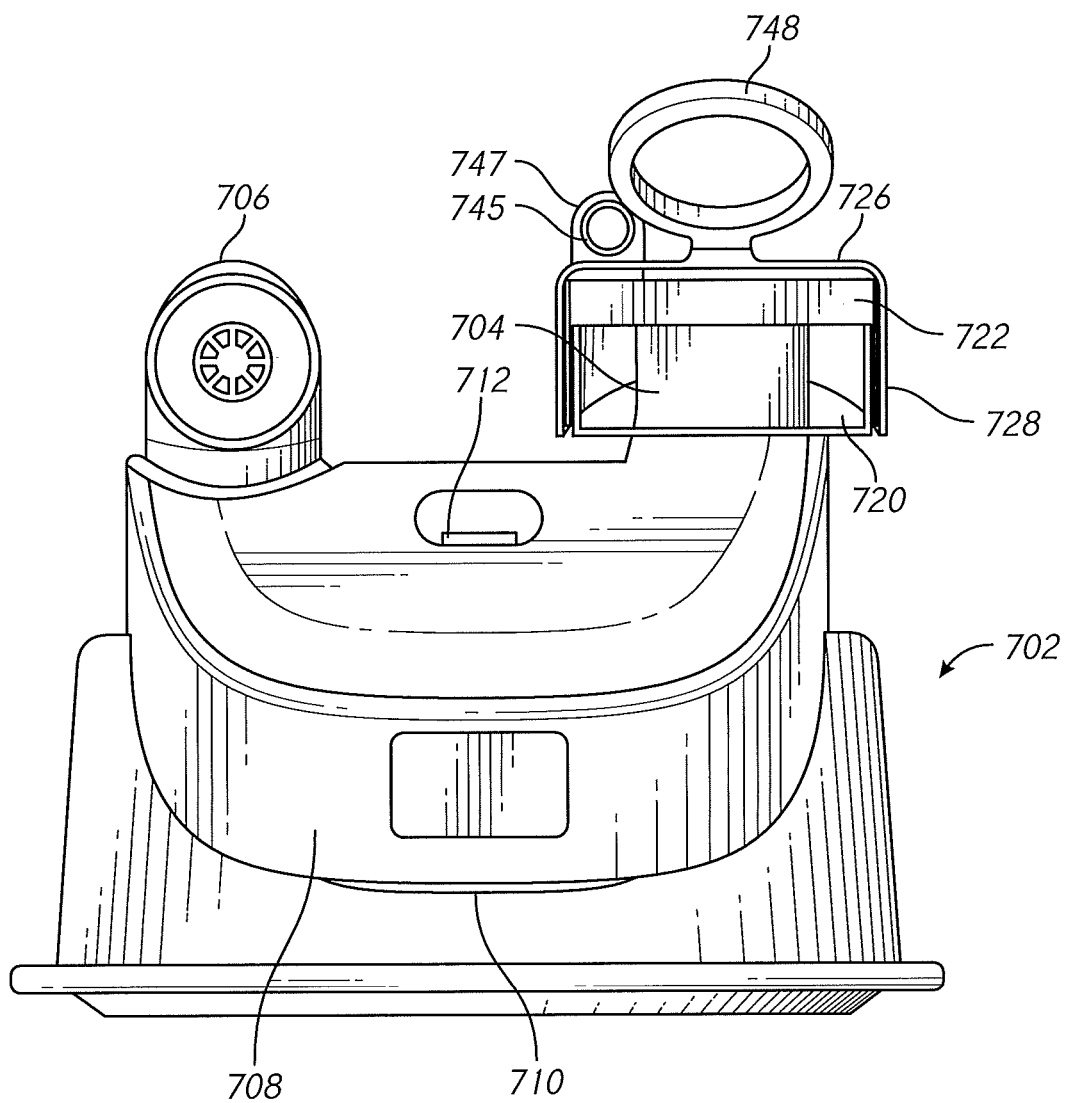
FIG. 33 illustrates a front elevation view of a chamber assembly.
Figure 34:
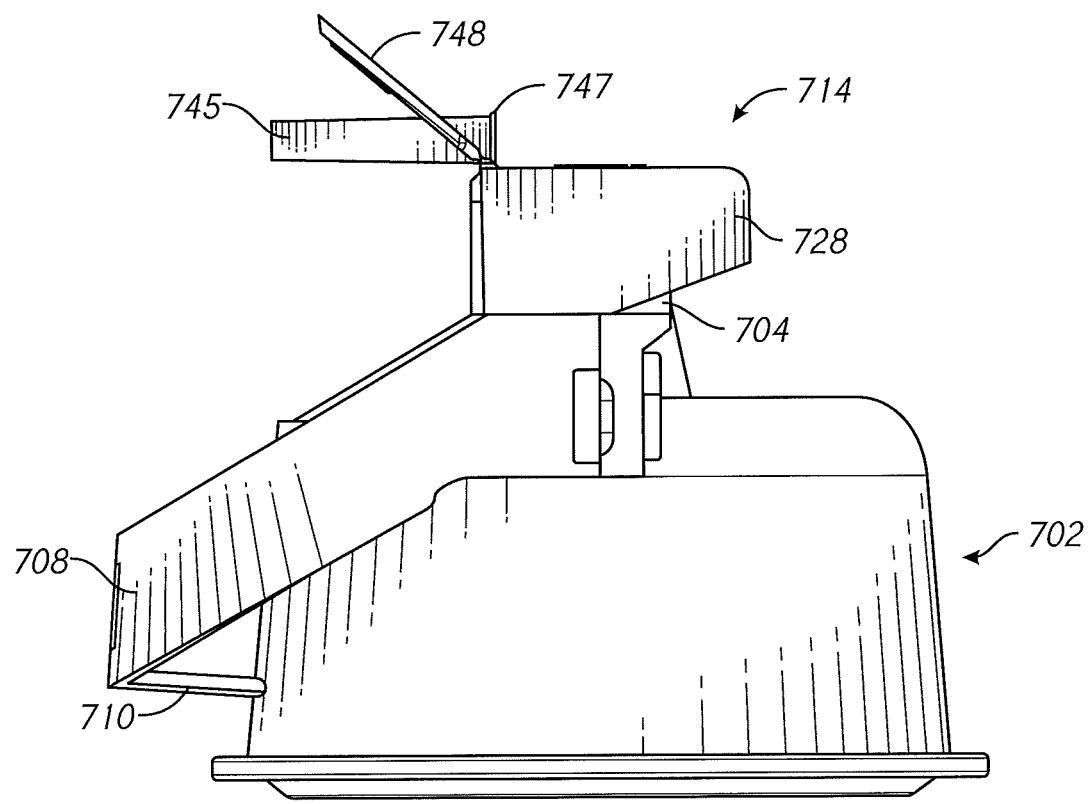
FIG. 34 illustrates a side elevation view of a chamber assembly.

As shown in FIG. 32, a water delivery conduit 724 can be wrapped about the inlet port 704. The wrapped water delivery conduit 724 can be inserted into the port cap 714 through the forward facing opening defined by the retainer 722. The wrapped water delivery conduit 724 can be positioned such that the inlet port 704 extends through the loop with the support 720 underlying the loop. The post 718 can be inserted into the port 704 with the finger 730 extending into the chamber 702.

The lid 726 and the flange 728 generally enclose the wrapped water delivery conduit 724. As shown in FIG. 32, a spike 744 can be connected to the water delivery conduit 724. The spike 744 can be received within a sleeve 745. In some configurations, the sleeve 745 is connected to the port cap 714. In some configurations, the sleeve 745 is connected to at least one of the collar 716 and the post 714. In the illustrated configuration, the sleeve 745 is connected to the collar 716. The sleeve 745 can be connected to the collar 716 in any suitable manner. The sleeve 745 can be joined to the retainer 722. In some configurations, the sleeve 745 can be integrally formed with the retainer 722. In some configurations, the sleeve 745 can be formed separate of the retainer 722 and secured thereto in any suitable manner. In the illustrated configuration, the sleeve is pivotally connected to the collar 716. In the some configurations, the sleeve 745 is pivotally connected to the retainer 722. In some such configurations, the sleeve 745 has a flange 747 that is connected to the retainer 722. In some such configurations, the flange 747 extends upward from an edge of the retainer 722. In such configurations, the sleeve 745 can pivot downwardly when then spike 744 is positioned within the sleeve 745.

With reference now to FIGS. 32 and 35, the port cap 614 can include a lifting structure 748. In some configurations, the lifting structure 748 can be joined to any suitable surface of the port cap 614. In the illustrated configuration, the lifting structure is joined to the lid 726. In some configurations, the lifting structure is joined to the front of the lid 726. In some configurations, the lifting structure 748 is pivotable relative to the port cap 614. The lifting structure 748 can have any suitable configuration. In the illustrated configuration, the lifting structure 748 is a ring. In some configurations, the lifting structure 748 can be a tab, hook or any other suitable structure. The lifting structure serves as a visual indicator to help encourage removal of the port cap 614 while also facilitating the removal.

Figure 15:
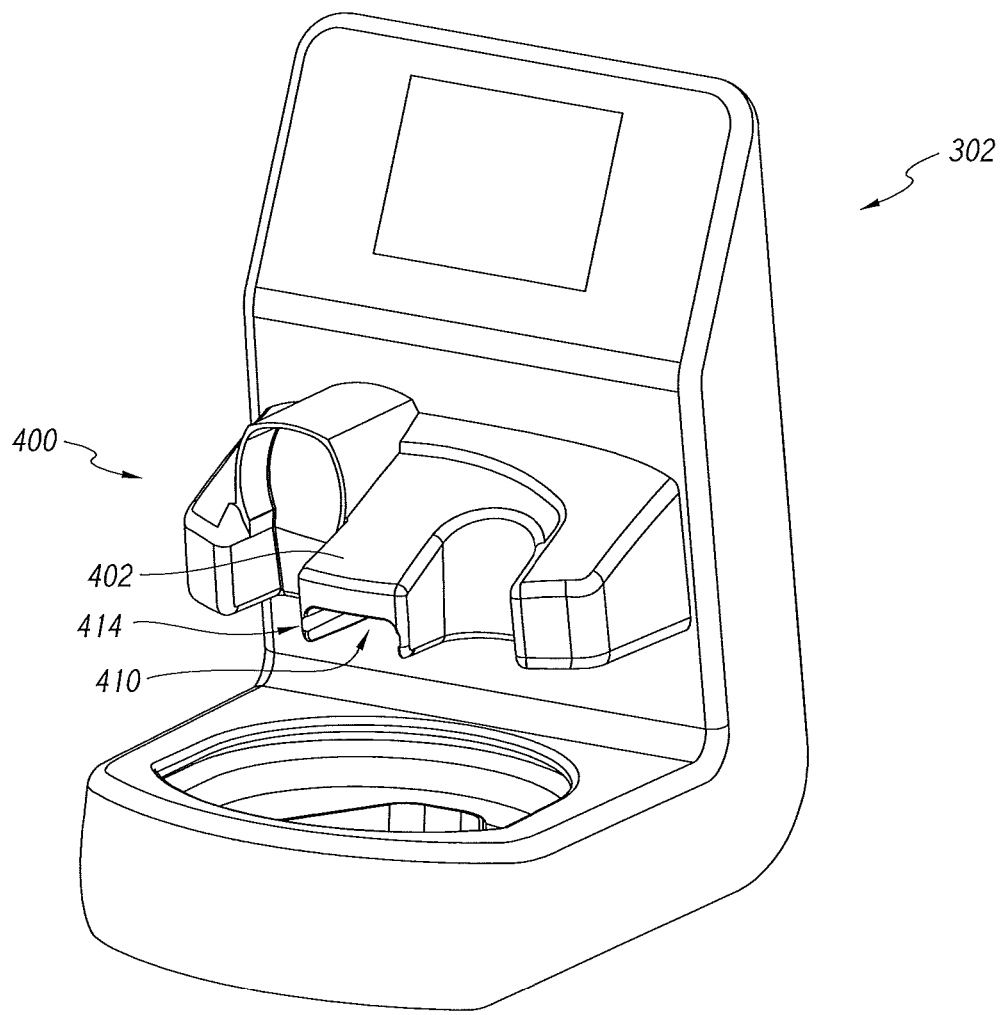
FIG. 15 illustrates the base having the sensor cartridge of FIG. 12 with the chamber removed.

The heater base 302 can include a sensor cartridge module 400 similar to sensor cartridge module 200. Similar to chamber 104 and sensor cartridge module 200, chamber 304 and sensor cartridge module 400 can include lead-in features to help guide the operator through installation of the chamber 304 on the heater base 302 and help prevent or inhibit improper set up. For example, as shown in FIGS. 12 and 15, the sensor cartridge module 400 can include a central male projection 402 configured to slide into a female recess 404 in the chamber 304 as shown in FIGS. 13A-13B. As shown, the recess 404 extends forward past a midpoint of or greater than halfway across the chamber 304, and the male projection 402 of the sensor cartridge module 400 extends past the midpoint of or greater than halfway across the chamber 304 when the chamber 304 is installed on the base 302. In some embodiments, this causes the male projection 402 to engage the chamber 304 before the chamber 304 otherwise engages the base 302, which can advantageously help guide the user in orienting the chamber 304 correctly on the base 302. For example, this feature can prevent or inhibit the user from attempting to install the chamber 304 by placing the protruding portion 305 above or on top of the rim edge 106. When the chamber 304 is properly installed, the top of the male projection 402 of the sensor cartridge module 400 and the top of the front of the chamber 304 can form an at least substantially continuous or consistent slope. This can advantageously provide a visual cue to the user that the chamber 304 has been properly installed.

In the illustrated embodiment, the sensor cartridge module 400 also includes a central channel 410 along a lower surface of the central male projection 402. The central channel 410 is configured to receive a central boss or raised portion 412 on the chamber 304. As shown, side walls of the central channel 410 can include generally horizontal grooves 414. The grooves 414 can be configured to receive corresponding rails 416 extending along the sides of the raised portion 412 of the chamber 304, as shown in FIG. 13B. When the chamber 304 is installed on the base 302 and coupled to the cartridge 400, the rails 416 sit in the grooves 414. The coupling configuration of the rails 416 in the grooves 414 can help inhibit the chamber 304 from excessive tilting.

The configuration and arrangement of, for example, the female recess 404 and raised portion 412 on the chamber 304 make the front and rear of the chamber 304 highly asymmetric. This asymmetry, the configuration of the sensor cartridge 400, and/or the corresponding lead-in features on the chamber 304 and sensor cartridge 400 advantageously prevent or inhibit the user from inserting the chamber 304 on the base 302 backwards or otherwise incorrectly setting up or misaligning the chamber 304 and/or base 302. The raised portion 412 also provides a visual guide as to the proper orientation of the chamber 304 for insertion on the base 302.

Figure 17:
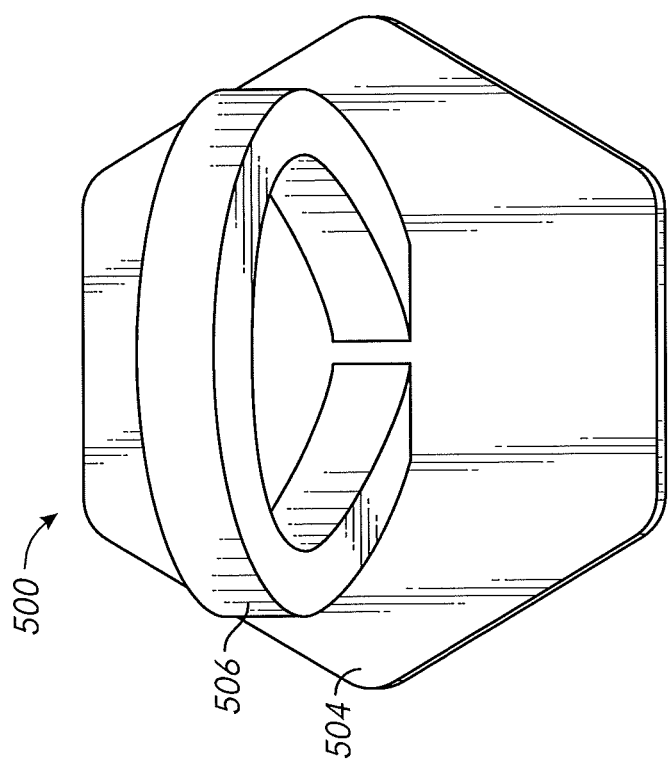
FIG. 17 illustrates a top perspective view of the end cap of FIG. 19.
Figure 16:
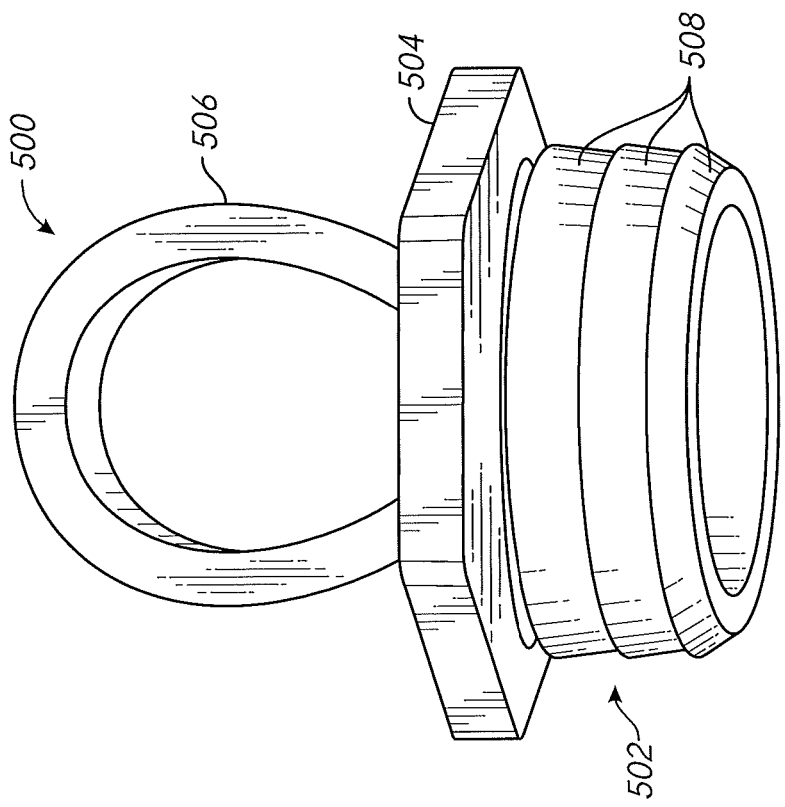
FIG. 16 illustrates a side view of an end cap for a Y-piece or conduit.

In some embodiments, one or more of the components of the breathing circuit assembly can be packaged for shipping and/or storage with an end cap 500 coupled to one or both ends of the conduit. An example embodiment of an end cap is shown in FIGS. 16-17. For example, an end cap 500 can be included on the end of Y-piece 127 as shown in FIGS. 18 and 19. The end cap 500 includes a body 502 configured to be inserted into the Y-piece, a flange 504, and a hook or pull ring 506.

The body 502 comprises frustoconical tapers 508. The tapers 508 promote a friction fit between the end cap 500 and Y-piece. The tapers 508 also create a seal with the Y-piece. The illustrated embodiment includes three tapers 508, although more or fewer are also possible. Multiple tapers 508 provide redundancy to help ensure a sufficient seal and friction fit. However, too many tapers 508 can create too great of a contact area. This can make the end cap 500 difficult to remove. In some embodiments, the body 502 can be sized to fit different sized Y-pieces, for example, both adult and infant Y-pieces.

The flange 504 is located on the end of the end cap 500 facing the bases or widest parts of the tapers 508. As shown, the flange 504 has a hexagonal shape. The hexagonal shape helps seal the end of the Y-piece and aids end cap 500 removal. A width or diameter of the flange 504 is greater than an outer diameter of the Y-piece to create an overhang. For example, for a 22 mm diameter Y-piece, the flange 504 can have a width of about 24 mm. The hexagonal shape can also provide a visual indicator that the Y-piece connector is blocked and further inhibits the user from attempting to attach other components while the end cap 500 is in place, which may be more likely if the flange 504 was round. Other non-circular shapes also can be used.

The hook 506 extends from the flange 504. The hook 506 advantageously allows the user to more easily grasp and remove the end cap 500 when needed. The hook 506 also allows the circuit to hang on a medical stand 520 when not in use and/or during system set up, as shown in FIGS. 18 and 19. The hook 506 can have a diameter of at least 8 mm to allow the hook 506 to accommodate medical stand hooks 522.

The body 502, flange 504, and hook 506 can be integrally formed or molded to create a single-piece end cap 500. The end cap 500 should be made of a material that is sufficiently strong while remaining soft or pliant enough to inhibit damage to the Y-piece. In some embodiments, the end cap 500 can be made of Thermolast K. In other embodiments, the end cap 500 can be made of Santoprene having a Shore A hardness of between about 20 and 80, for example, about 55. Santoprene has a higher friction coefficient than some alternative materials, which can help improve end cap 500 retention in the Y-piece.

Alternative embodiments of end caps 500 are illustrated in FIGS. 20A-24E. In these embodiments, the flange 504 is circular rather than hexagonal. Additionally, as shown, the hook or pull ring 506 extends from a side of the flange 504 rather than a top of the flange 504. In some configurations, the hook can be a tab with an aperture defined through the tab. In any event, in the illustrated configurations, the aperture or hook can be positioned off to one lateral side of an axis extending through the body that engages with the component to which the cap is mounted. In other words, the aperture or hook is positioned off to one side of the body and/or flange. Locating the hook 506 to the side of the flange 504 can cause the force used to remove the end cap 500 to be applied in a rotational direction rather than a linear direction. This arrangement can advantageously allow the end cap 500 to be removed with less force.

Figure 20A:
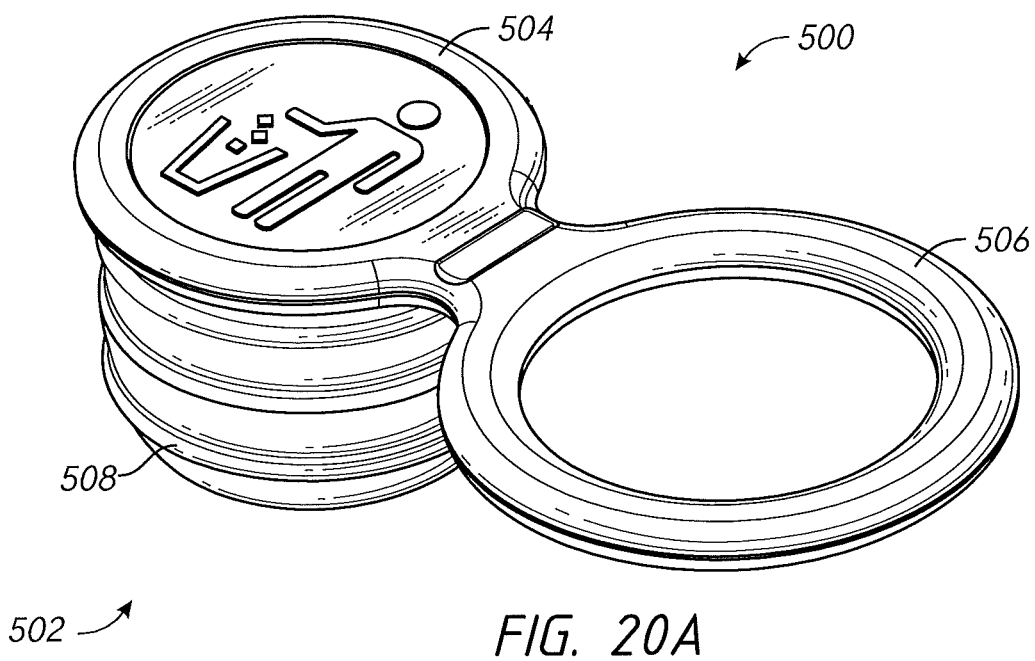
FIG. 20A illustrates a perspective view of an alternative end cap.
Figure 20B:
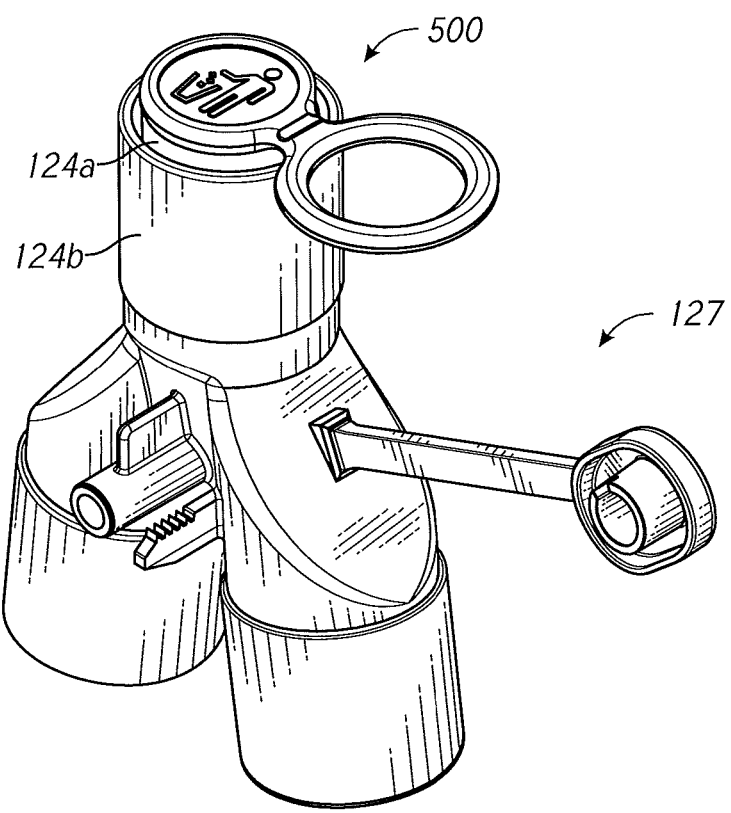
FIG. 20B illustrates the end cap of FIG. 20A coupled to a Y-piece.
Figure 21A:
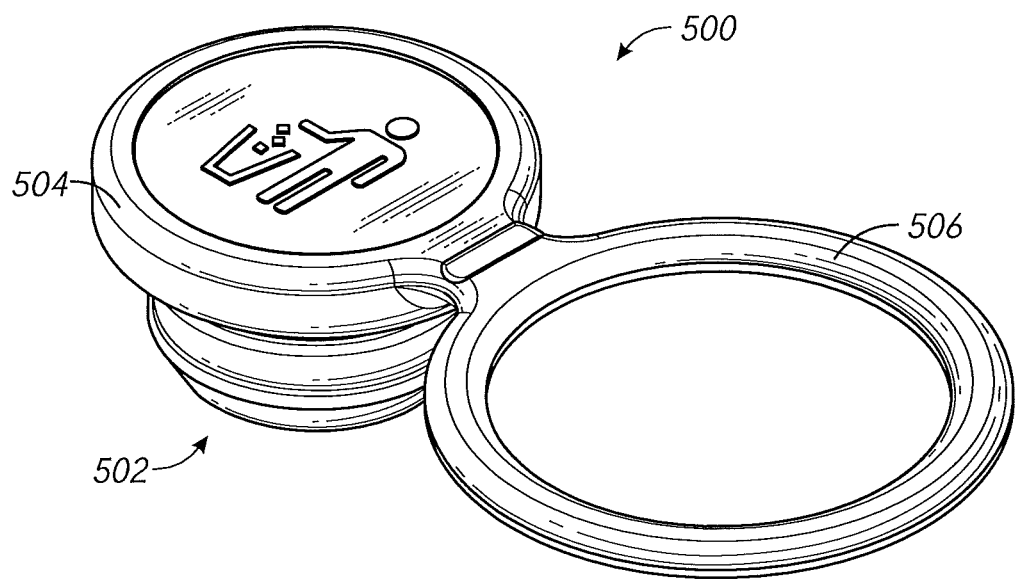
FIG. 21A illustrates a perspective view of an alternative end cap.
Figure 21B:
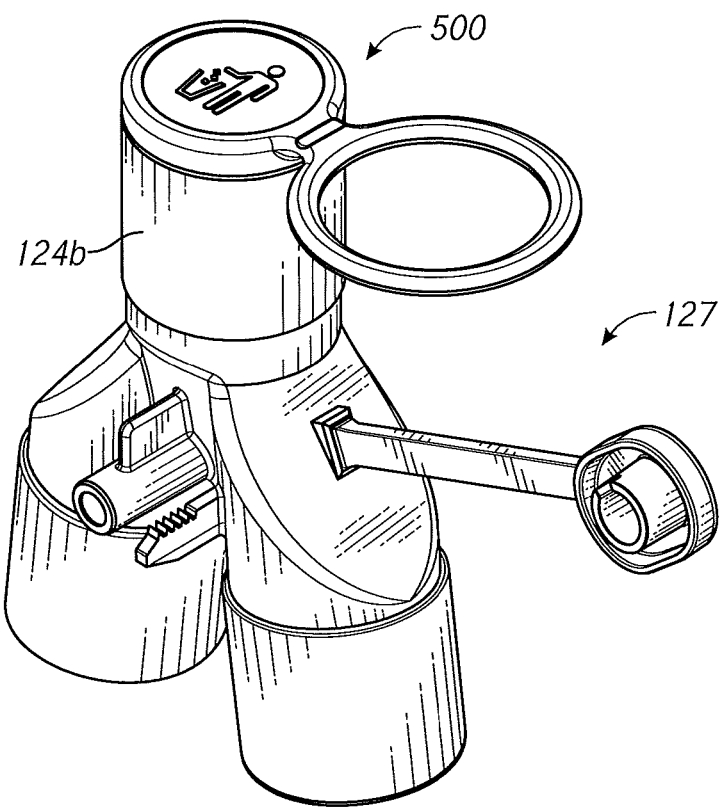
FIG. 21B illustrates the end cap of FIG. 21A coupled to the Y-piece.
Figure 22A:
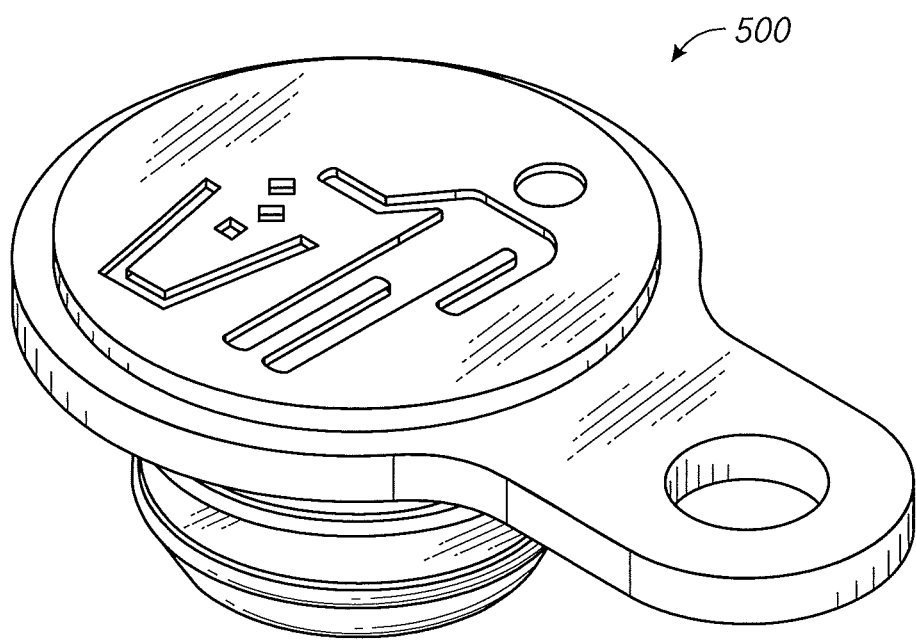
FIG. 22A illustrates a perspective view of an alternative end cap.
Figure 22B:
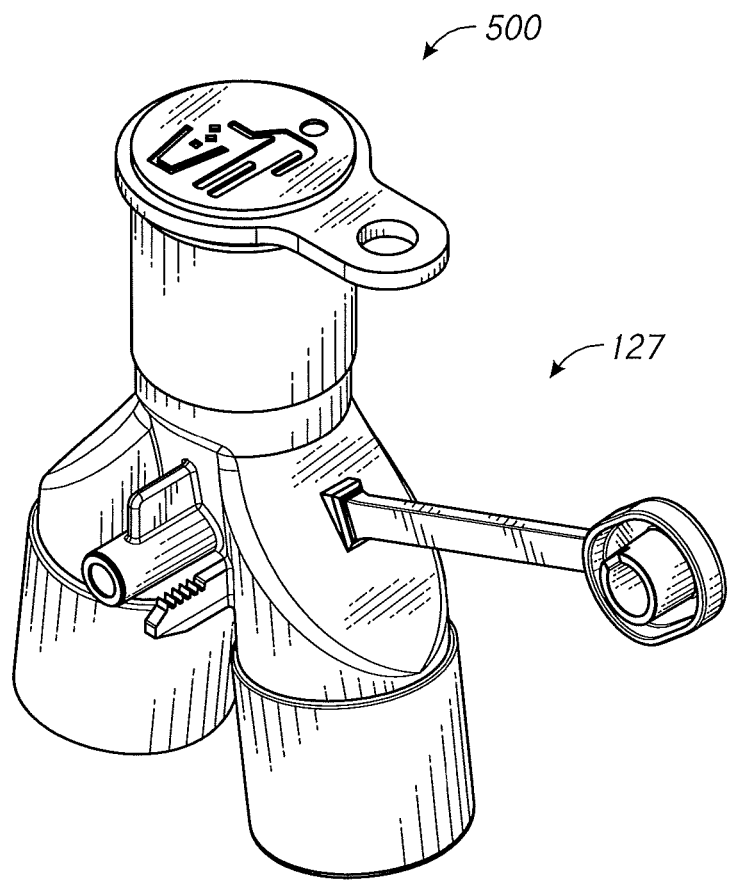
FIG. 22B illustrates the end cap of FIG. 22A coupled to the Y-piece.
Figure 23A:
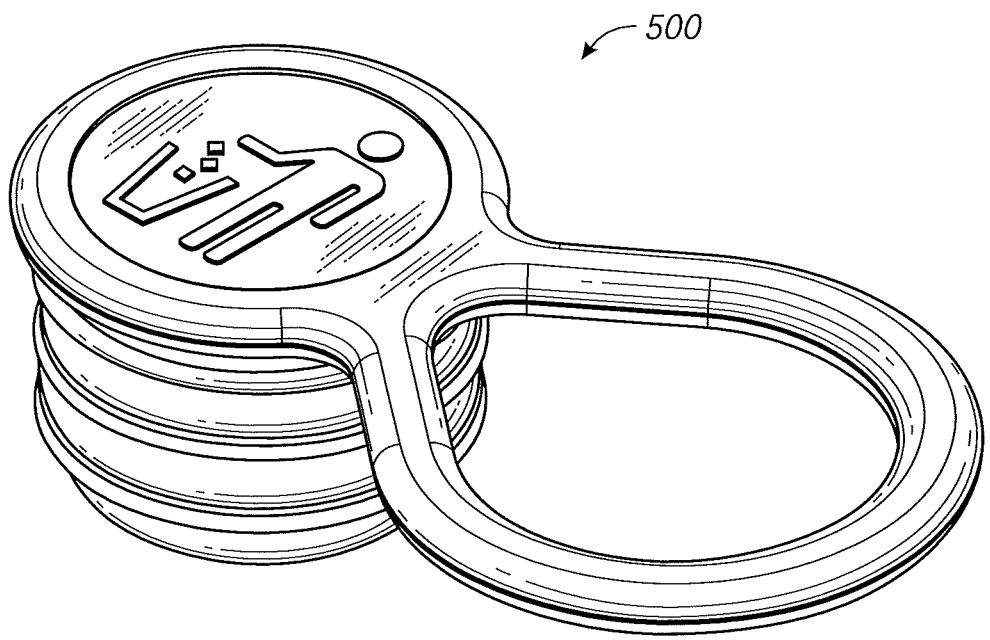
FIG. 23A illustrates a perspective view of an alternative end cap.
Figure 23B:
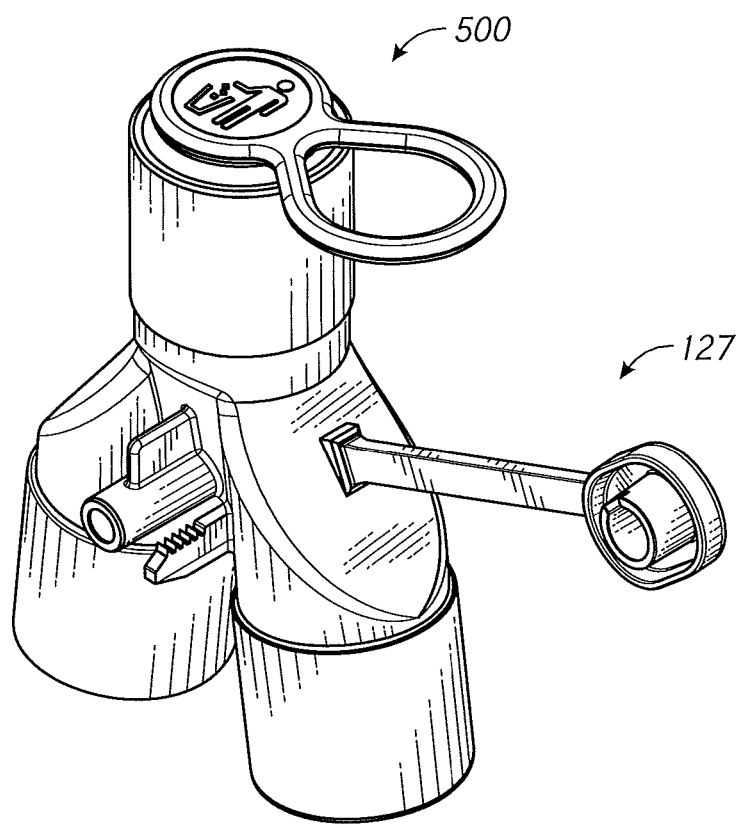
FIG. 23B illustrates the end cap of FIG. 23A coupled to the Y-piece.
Figure 24A:
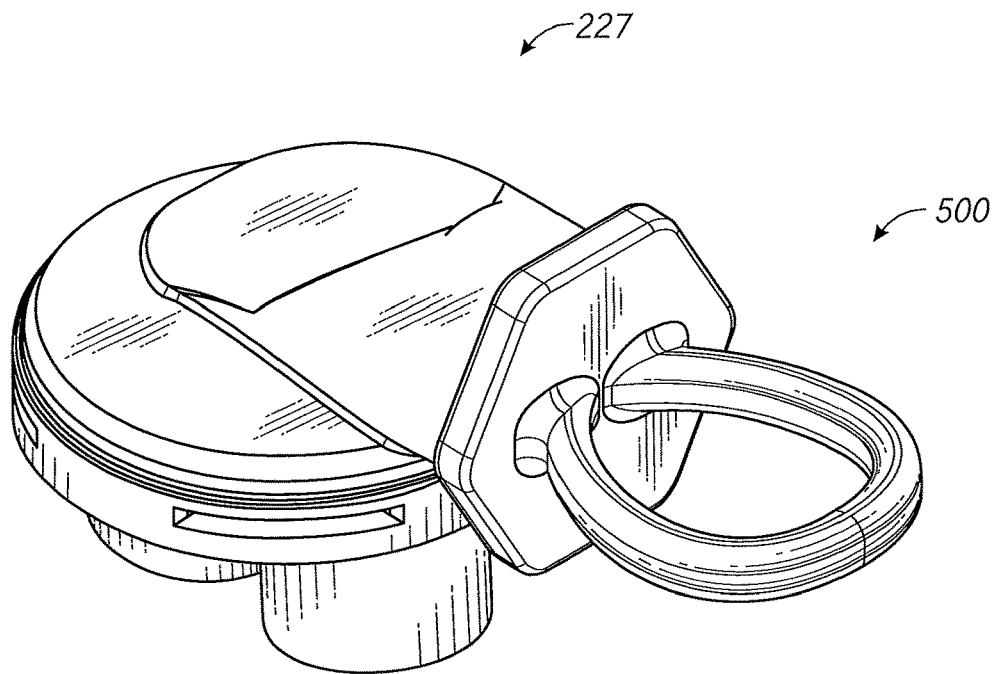
FIGS. 24A-24E illustrate the end caps of FIGS. 16, 20A, 21A, 22A, and 23A, respectively, coupled to an alternative Y-piece.
Figure 24B:
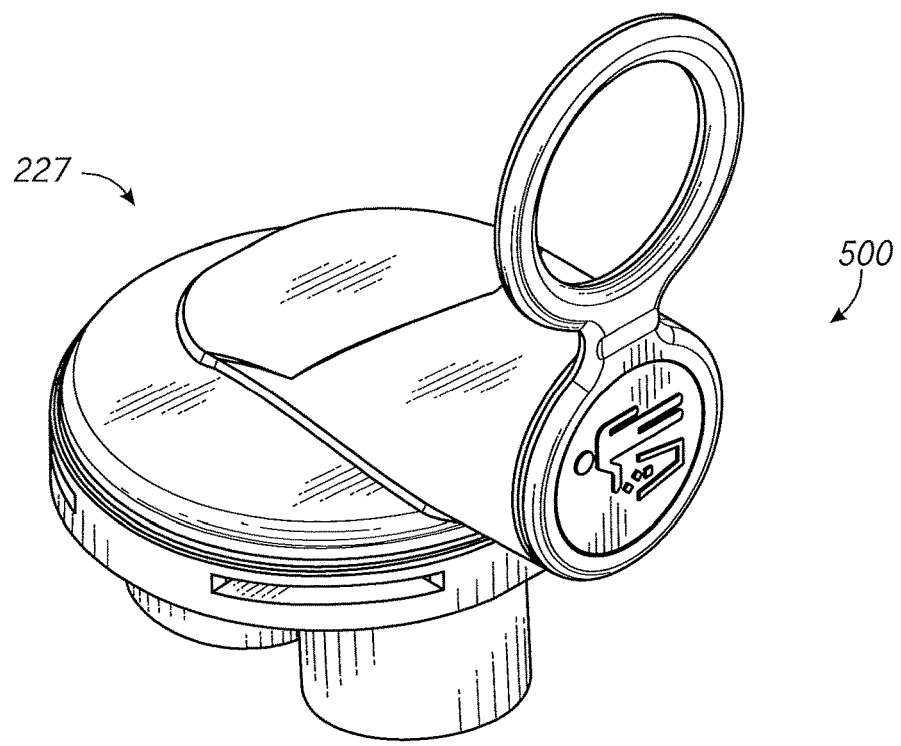
Figure 24C:
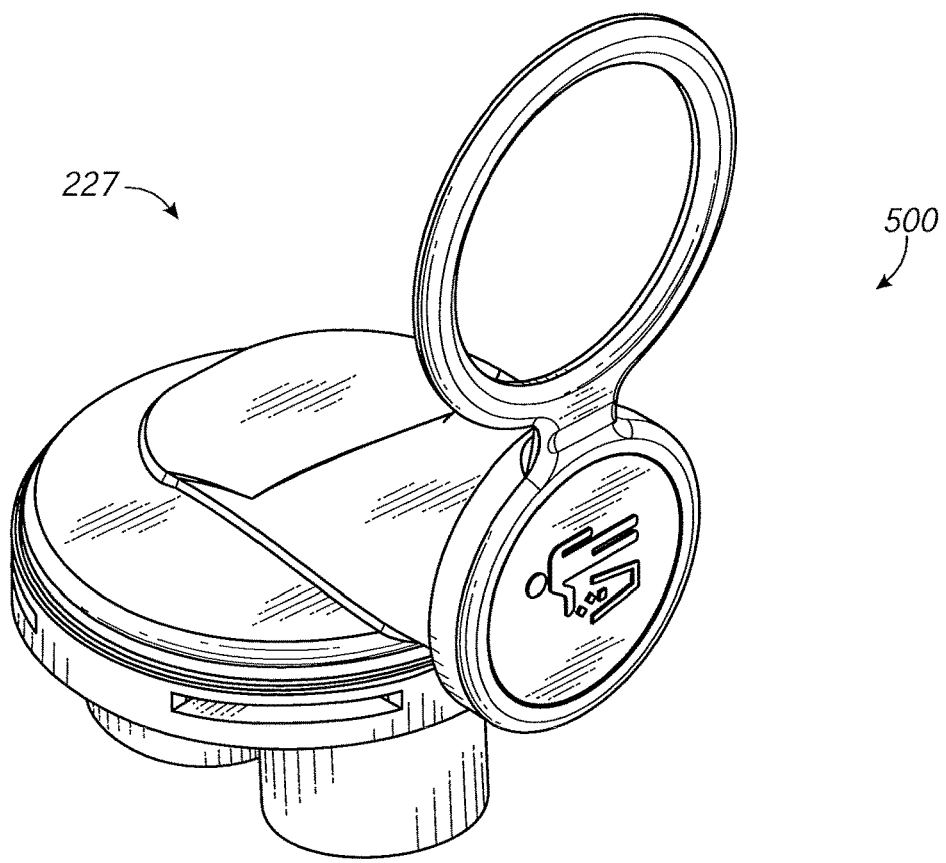
Figure 24D:
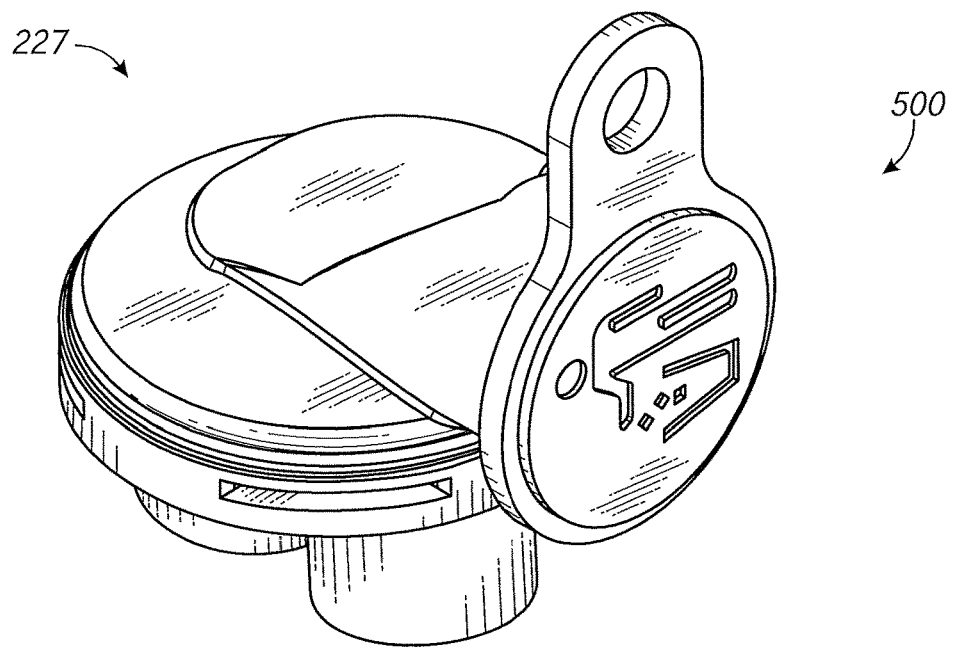
Figure 24E:
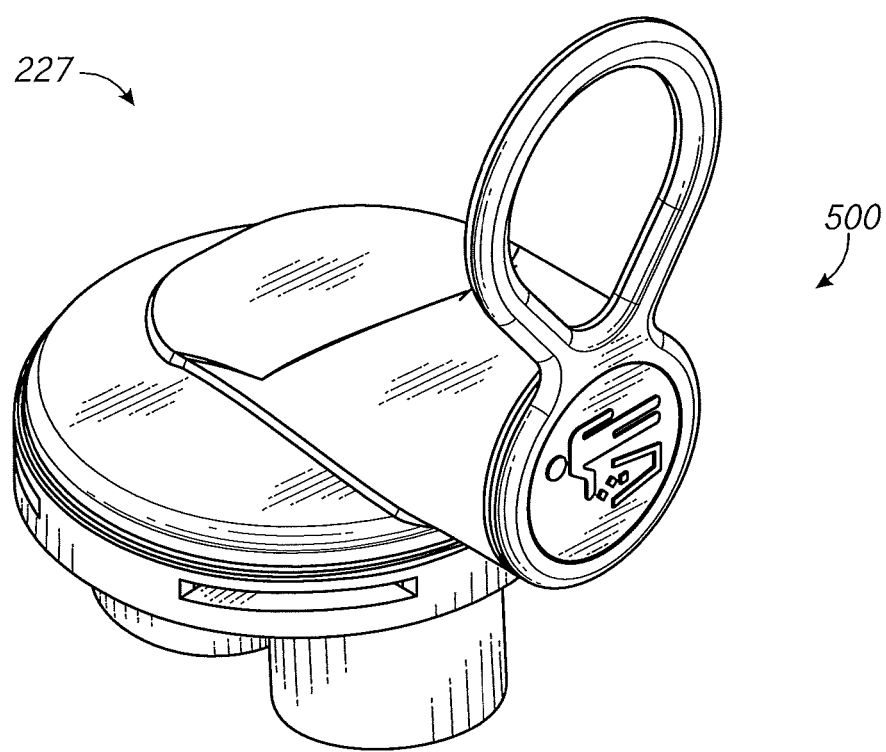

The hook 506 and flange 504 can have varying dimensions. For example, the embodiment of FIGS. 21A and 21B has a larger diameter hook 506 and larger diameter flange 504 than the embodiment of FIGS. 20A and 20B. If the end cap 500 of FIGS. 20A and 20B is connected to a Y-piece 127 having an inner shell 124a and an outer shell 124b, the flange 504 covers only the inner shell 124a as shown in FIG. 20B. The flange 504 of the end cap 500 of FIGS. 21A and 21B covers both the inner shell 124a and the outer shell 124b as shown in FIG. 21B. FIGS. 22A and 23A illustrate additional embodiments of end caps 500, and FIGS. 22B and 23B illustrate the end caps of FIGS. 22A and 23A, respectively, coupled to a Y-piece 127. FIGS. 24A-24E illustrate the end caps of FIGS. 16, 20A, 21A, 22A, and 23A, respectively, coupled to an alternative Y-piece 227. The Y-piece 227 of FIGS. 24A-24E can be used for an infant patient.

Figure 38:
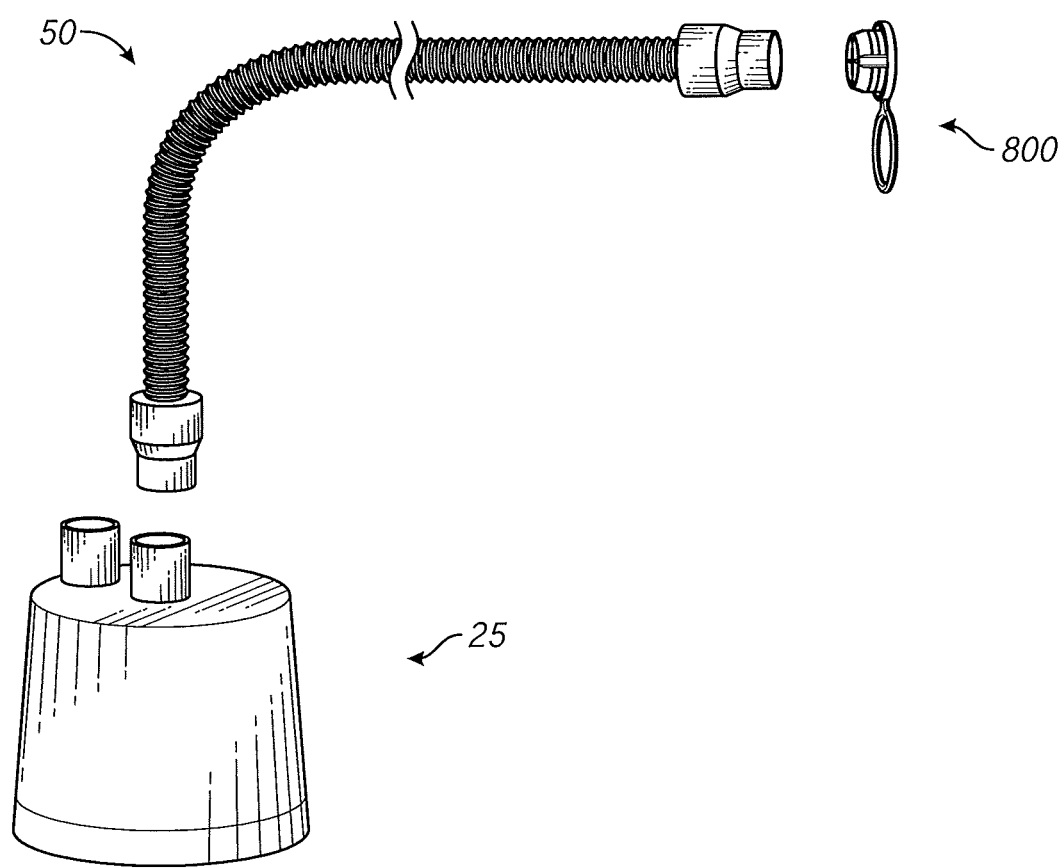
FIG. 38 illustrates a schematic of a medical system.

FIG. 38 illustrates a system comprising a chamber 25, a circuit 50 and a cap 800. The chamber 25 is configured to hold a liquid, such as, for example, water. The chamber 25 is configured to couple with a heating apparatus that, in use, heats the liquid and, thereby, forms vapour. The chamber is configured to couple with a gases source such that gases provided to the chamber are heated and take up the vapour as they travel through the chamber. The heated, humidified gases are delivered by the circuit 50 to the patient. The cap 800 is configured to be attached to the circuit 50. The illustrated circuit 50 is an example of a circuit to which the cap 800 can be attached and is not meant to be limiting. In an embodiment, the cap 800 is configured to couple with an intermediate respiratory component, such as, for example, a wye-piece, or an additional circuit.

Sealing, as herein described, refers to at least partial sealing of a medical component, such as, for example, a circuit. Sealing prevents, or at least partially prevents, dust, or larger contaminants, such as a finger, for example, from entering the circuit. Sealing could be achieved by the use of a tortuous path, a cap, or a cap that provides a tortuous path. The tortuous path substantially seals or at least partially seals the circuit (i.e., may not result in a completely air impervious seal).

FIGS. 39A-39D illustrate the cap 800 in more detail. The cap 800 comprises a ring 801 connected to a plug 804. The ring 801 may be connected to the plug 804 by a throat 802. The plug 804 comprises a disc 814 and a body 805. The disc 814 comprises an upper surface 816 and a lower surface 818. The disc 814 has a diameter that is larger than the diameter of the body 805. The disc 814 further comprises a lip 808 that extends from the lower surface 818. The plug 804 comprises a roughly cylindrical structure defining a tube. The tube comprises a first end and a second end. The first end is sealed by the lower surface 818 of the disc 814. The second end is branched by a pair of ribs 812 that are perpendicular to each other. The ribs 812 are coupled with the lower surface 818 and abut an internal wall of the body 805. The plug 804 comprises four segments of three frustoconical tapers 806 adjacent to the body 805. Each of a plurality of channels 810 is defined between adjacent segments of the frustoconical tapers 806. The plurality of channels 810 extend into the lower surface 818.

The ring 801 has a diameter large enough to insert a finger. For example, the diameter may be greater than 8 mm. In the illustrated embodiment, the diameter is 25 mm. The ring 801 is configured to enable easy removal of the cap 800 from the circuit 50. The ring 801 is configured to allow the cap 800 to be removed from the circuit 50 without use of excessive force while the retaining force created by friction between the body 805 and the circuit 50 remains enough to hold the cap 800 in place when the circuit 50 is hung. In an embodiment, the cap 800 is configured to be removed by a force in the range of 5-30 Newtons (N). In an embodiment, the cap 800 is configured to be removed by a force in the range of 5-15 N. In an embodiment, the cap 800 is configured to be removed by a force of about 15 N. This provides a retention force that is strong enough to support the weight of the circuit 50 and yet allows a user to insert and remove the cap 800 without impacting the usability of the circuit 50.

The ring 801 enables the circuit 50 to be hung on a supporting structure, such as a medical stand or hook, for example. This facilitates easy storage of the circuit 50 prior to use, during a pause in use, or following use. The system can be set up prior to use and be ready for use by a patient.

The plug 804 is coupled with the ring 801 by the throat 802. This causes leverage to be applied to the plug 804 when a force is applied to the ring 801, which reduces the force required to remove the cap 800 from the circuit 50. The length of the throat 802 can be increased to increase the amount of leverage applied to the plug 804. In the illustrated embodiment, the length of the throat 802 is 3 mm. The width of the throat 802 can also be increased to increase the amount of leverage applied to the plug 804. In an embodiment, the ring 801 is directly coupled to the plug 804 with no intervening throat. This reduces the overall size of the cap 800 but increases the force required to remove the cap 800 from the circuit 50.

The body 805 of the plug 804 couples with the circuit 50. In the illustrated embodiment, the body 805 is configured to be a male component. Thus, the body 805 is received by the circuit 50 and extends into the interior of the circuit 50. The body 805 is configured to be held in place in the circuit 50 by, for example, a friction fit. In the illustrated embodiment, the body 805 is configured to fit a 22 mm taper circuit connector. A male component renders the cap 800 independent of the external configuration of the circuit connector. Thus, the cap 800 can be used with different circuits having the same internal connector size, for example, a 22 mm taper.

In an embodiment, the body 805 comprises a female component that is configured to receive the circuit 50. This protects the interior of the circuit from potential damage due to interaction with the body 805.

The size of the cap 800, or the plug 804, can be scaled to fit, for example, 8.5 mm, 12 mm, 15 mm, 17 mm, 22 mm, 23 mm, or 30 mm tapers. This enables the cap 800 to be used with a variety of medical components, such as, but not limited to, a wye-piece, medical circuits or interface circuits of different sizes.

The body 805 comprises four segmented groups, each comprising three frustoconical tapers 806. The groups of frustoconical tapers 806 are configured to form a sealing interface with the interior of the circuit 50. The sealing interface is formed using a friction fit between the frustoconical tapers 806 and the interior of the circuit 50. The frustoconical tapers 806 hold the cap 800 in place in the circuit 50 during use until sufficient force is applied to remove the cap 800 from the circuit. Three frustoconical tapers 806 are chosen such that the force required to remove the cap 800 from the circuit 50 is within the capabilities of a user and yet exceeds other forces encountered during use.

In an embodiment, a single frustoconical taper 806, or two frustoconical tapers 806, form the sealing interface with the interior of the circuit 50. The single or two frustoconical tapers 806 reduce the length of the body 805 that is inserted into the interior of the circuit 50 while facilitating sealing between the body 805 and the interior of the circuit. The single or two frustoconical tapers 806 reduce the force required to remove the cap 800 from the circuit 50.

In a further embodiment, four or more frustoconical tapers 806 form the sealing interface with the interior of the circuit 50. Four or more frustoconical tapers 806 improve the sealing between the body 805 and the interior of the circuit 50.

Figure 39A:
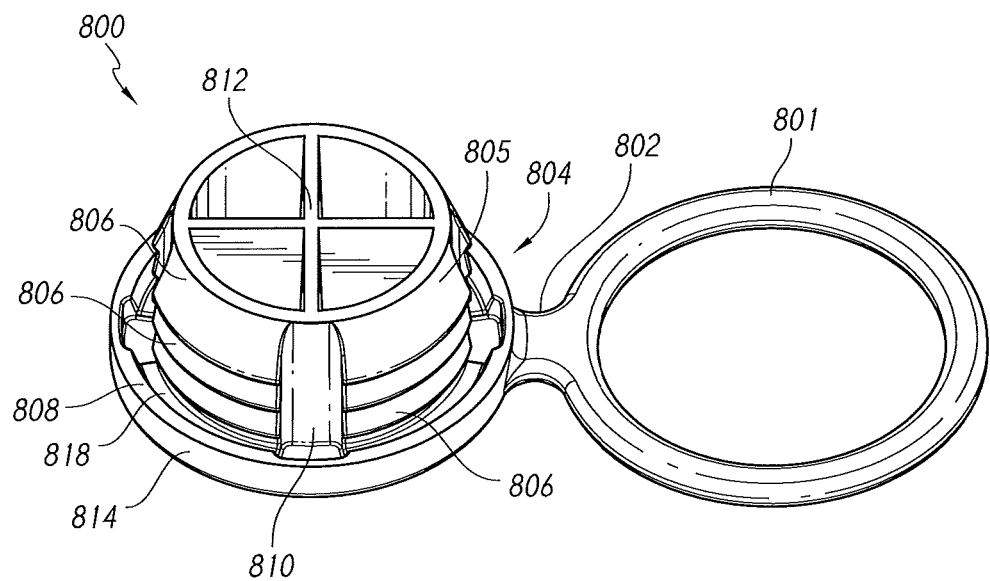
FIGS. 39A-39B illustrate a perspective view of a cap.
Figure 39B:
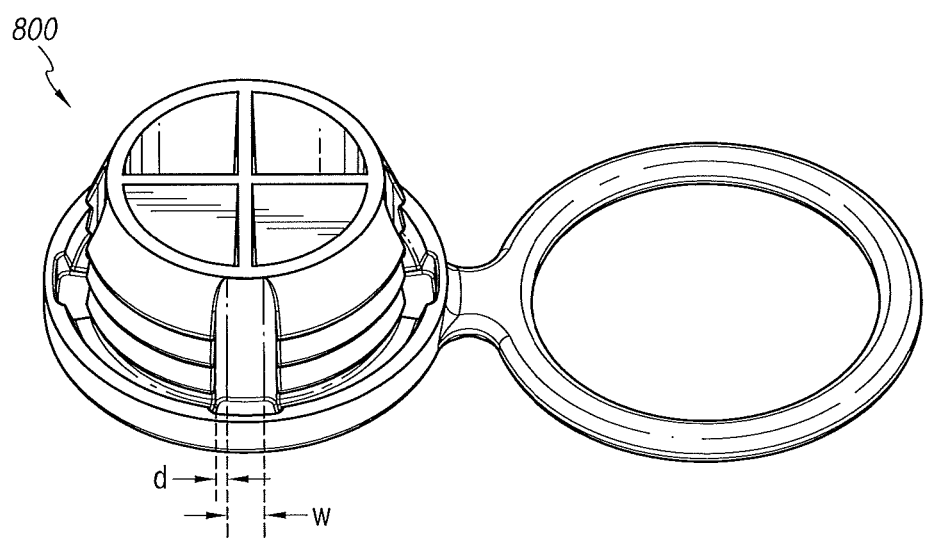
Figure 39C:
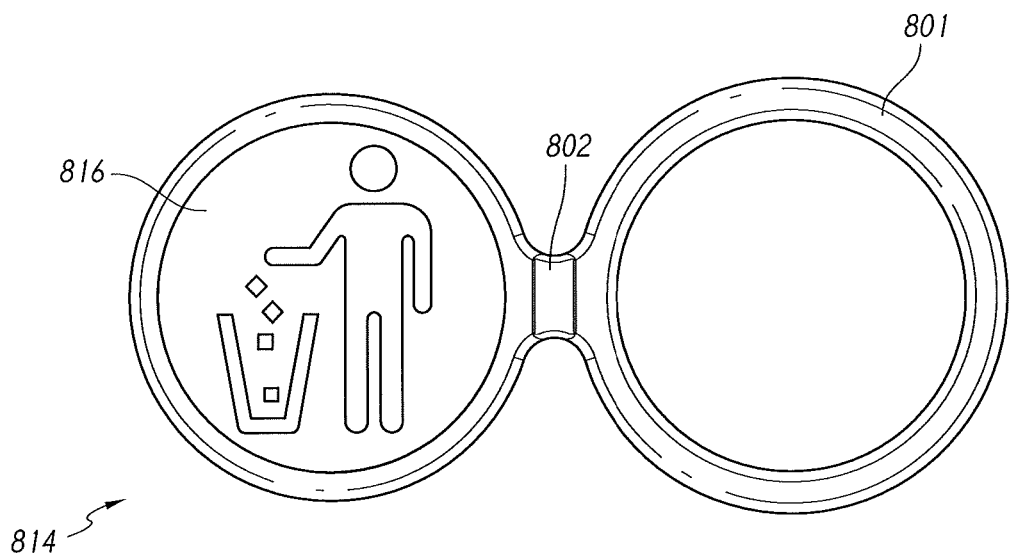
FIG. 39C illustrates a top view of a cap.
Figure 39D:
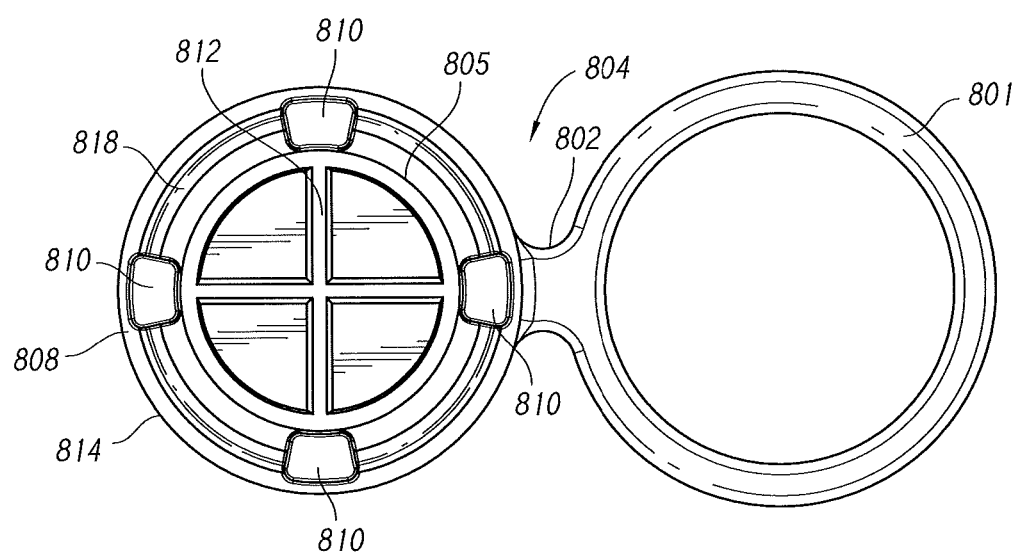
FIG. 39D illustrates a bottom view of a cap.

The segmented groups of frustoconical tapers 806 are each separated by the channels 810. The channels 810 form a path through which gases within the circuit 50 can move into the atmosphere. Thus, the channels 810 provide a way for the gases to vent from the circuit 50 should a user initiate gases flow through the circuit while the cap 800 is in place. The channels 810 are located on the body 805 and, thus, are received by the circuit 50 as the body 805 is inserted into the circuit. The channels 810 are subtle and do not negatively impact the overall look of the cap 800. As illustrated in FIG. 39B, the width (w) of each of the channels 810 is 5 mm. In the illustrated embodiment, the depth (d) of each of the channels 810 at the deepest point is 1.3 mm. The depth (d) of each of the channels 810 can be varied provided it remains within manufacturing constraints, for example, greater than 1 mm. A thin material is vulnerable to breakage and a thick material takes time to cool, which can lead to distortion of the parts.

In an embodiment, the width of the channels 810 is less than 5 mm, for example, 2 mm. This improves the sealing between the cap 800 and the circuit 50. In a further embodiment, the width of the channels 810 is greater than 5 mm, for example, 7 mm. This improves the venting capacity of the cap 800.

The four channels 810 may be spaced evenly around the perimeter of the body 805. This reduces the likelihood of the cap becoming unsealed and disconnecting with the circuit 50 due to an uneven amount of gases being vented to the atmosphere through each channel. Four channels 810 can withstand expected pressures at typical operating pressures, such as 13 kPa at 60 lpm or 20 kPa at 70 lpm.

In an embodiment, two channels 810, substantially evenly spaced around the perimeter of the body 805 maintain a high sealing force between the cap 800 and the circuit 50.

In an embodiment, three channels 810 substantially evenly spaced around the perimeter of the body 805 allow more venting to the atmosphere.

In an embodiment, five channels 810 substantially evenly spaced around the perimeter of the body 805 increase the venting of gases to the atmosphere. Thus, more venting of gases to the atmosphere can occur with a larger number of the channels 810.

The illustrated embodiment optimises the sealing force with the venting capacity of the cap 800. For example, 27% of the sealing diameter of the cap 800 facilitates venting gases to the atmosphere and 73% of the sealing diameter of the cap 800 forms sealing surfaces between the cap 800 and the circuit. A greater venting capacity may negatively impact the sealing of the cap 800, which may cause the cap 800 to come off in use. Greater sealing of the cap 800 may reduce the venting capacity, which may cause the cap 800 to come off in use. Evenly spaced or substantially evenly spaced channels 810 around the perimeter of the body 805 provides more balanced venting of the gases to the atmosphere. This reduces the chance of the cap 800 coming off upon activation of the gases source.

The channels 810 extend into the lower surface 818 of the disc 814. This facilitates venting of gases from within the interior of the circuit 50 to the atmosphere by preventing the lower surface 818 or the disc 814 from sealing onto the circuit connector, such as might be encountered, for example, if the circuit 50 is coupled to the cap 800 such that the connector is flush with the lower surface 818. The channels 810 protrude by 0.5 mm into the lower surface 818 of the disc 814.

In an embodiment, the channels 810 extend into the lip 808 of the disc 814 to further facilitate venting of gases from within the interior of the circuit 50 to the atmosphere. The channels 810 protrude into the lip 808 of the disc 814 by 0.5 mm.

A pair of ribs 812, which are perpendicular to each other, branch the diameter of the second end of the tube formed by the body 805. The ribs 812 provide structural support to the body 805. This enables the body 805 to be received by the interior of the circuit 50 forming a seal.

In an embodiment, multiple ribs 812 provide additional structural support to the body 805.

In a further embodiment, a single rib 812 is used to provide structural support to the body 805. This reduces the amount of material required to form the cap 800 and simplifies the structure of the cap 800.

The disc 814 forms a barrier that at least partially seals the circuit 50 from the atmosphere. For example, the disc 814 prevents dust and larger contaminants, such as a finger or a medical instrument, from being inserted into the circuit 50 while it is attached to the cap 800. The disc 814 indicates to the user that the cap 800 should be removed prior to attaching a medical component to the circuit 50. For example, the disc 814 comprises a diameter that is larger than the diameter of the circuit. In the illustrated embodiment, the diameter of the disc 814 comprises 30 mm, compared with the circuit diameter of 22 mm.

In an alternative embodiment, the disc 814 comprises an eye-catching shape, for example, a hexagon or a square, to encourage the user to remove the cap 800 prior to use of the circuit 50.

In the illustrated embodiment, the upper surface 816 of the disc 814 comprises a visual indicator, by way of a drawing, colour, message or instructions to the user. The visual indicator indicates to the user, for example, correct usage of the cap 800 or disposal of the cap 800. The visual indicator can be embossed, raised or printed onto the upper surface 816.

In an embodiment, the upper surface 816 is colour coordinated with other medical components in the system. In an alternative embodiment, the upper surface 816 comprises a colour that indicates the cap 800 is disposable, such as, for example, red.

The lower surface 818 of the disc 814 seals the first end of the tube as defined by the body 805. The lip 808 surrounds the lower surface 818 of the disc 814. The lip 808 improves the aesthetic features of the cap 800, such as, for example, by subtly incorporating the channels 810 into the cap 800. In the illustrated embodiment, the lip 808 is 1.5 mm high. The lip 808 improves the sealing between the cap 800 and the circuit by sealing onto the exterior of the circuit.

The cap 800 is made from a material that does not damage the interior of the circuit when a friction fit is formed between the cap 800 and the interior of the circuit. The material is soft to protect the circuit and yet sufficiently rigid that the structure of the cap 800 is maintained. An example of an appropriate material is a thermoplastic elastomer, a thermoplastic polyurethane, or an elastomer.

Figure 40:
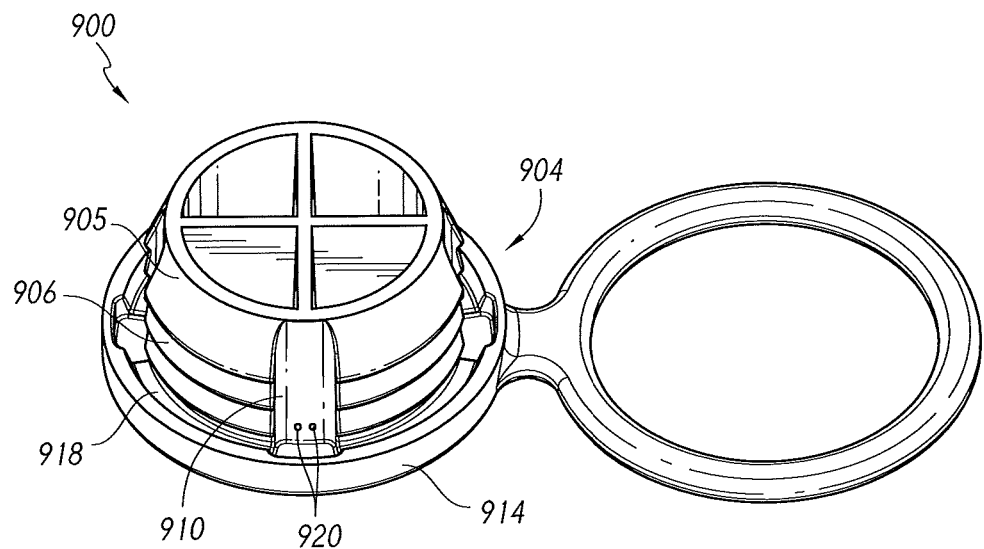
FIG. 40 illustrates a perspective view of a cap.

FIG. 40 illustrates an example embodiment, wherein a cap 900 comprises a plug 904. The plug 904 comprises a body 905 that is configured to be received by the circuit 50. The body 905 comprises segmented groups of frustoconical tapers 906 configured to at least partially seal with the interior of the circuit. The segmented groups of frustoconical tapers 906 are each separated by the channels 910. The channels 910 form a pathway through which gases within the circuit can vent to the atmosphere if a gases source is activated prior to removal of the cap 900 from the circuit.

The channels 910 comprise at least one orifice 920 to facilitate venting of gases from the circuit to the atmosphere. The at least one orifice 920 extend through the channels 910 and are configured to form a pathway between the lumen of the circuit 50 and the atmosphere. The channels 910 help to direct the vented gases toward the at least one orifice 920. In the illustrated embodiment, the channels 910 comprise two orifices 920. The orifices 920 can be used in combination with the channels 910 to further facilitate venting of the gases from the circuit to the atmosphere. In the illustrated embodiment, the orifices 920 are shown positioned near a lower surface 918 of a disc 914. Thus, the orifices 920 are positioned open to the atmosphere and are not sealed by the interior of the circuit. As a result, the cap 900 has a greater capacity to vent gases to the atmosphere.

In an embodiment, the cap 900 comprises multiple orifices 920. For example, the cap 900 may comprise three or more orifices 920, which further facilitate the venting of gases from the circuit.

In a further embodiment, the cap 900 comprises at least one orifice 920 with a larger diameter. This increases the capacity of the cap 900 to vent gases from the circuit 50. As a result, a reduced number of the orifices 920 is used while facilitating additional venting of gases from the circuit.

Alternatively, the orifices 920 comprise a smaller diameter. This renders the orifices 920 more subtle and less obtrusive to the user. A smaller diameter also reduces the likelihood of dust or other contaminants entering the circuit. Thus, multiple orifices 920 are used to allow additional venting from the circuit.

In a further embodiment, the orifices 920 are positioned on at least one of the frustoconical tapers 906. The orifices 920 can be used without or instead of the channels 910. In this embodiment, the sealing surfaces of the cap 900 are increased, facilitating better sealing between the cap 900 and the circuit.

In a further embodiment, the orifices 920 are positioned within the portions of the channels 910 that extend into the lower surface 918 of the disc 914. The orifices 920 thus protrude through the upper surface 916 of the disc 914. Thus, the channels 910 direct the gases toward both the atmosphere and the orifices 920. This facilitates greater venting of the gases without negatively impacting the sealing forces of the cap 900.

Figure 41A:
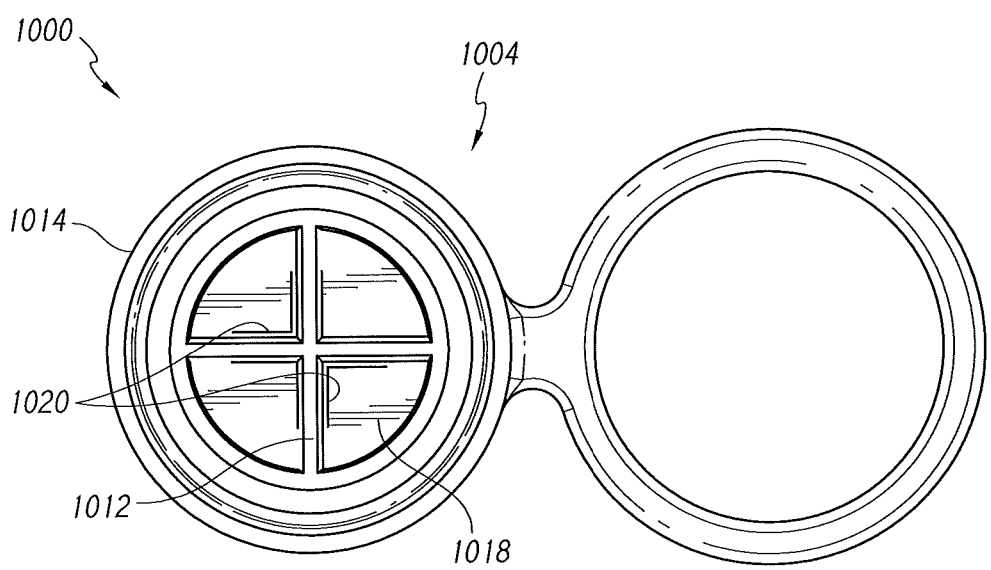
FIG. 41A illustrates a bottom view of a cap.
Figure 41B:
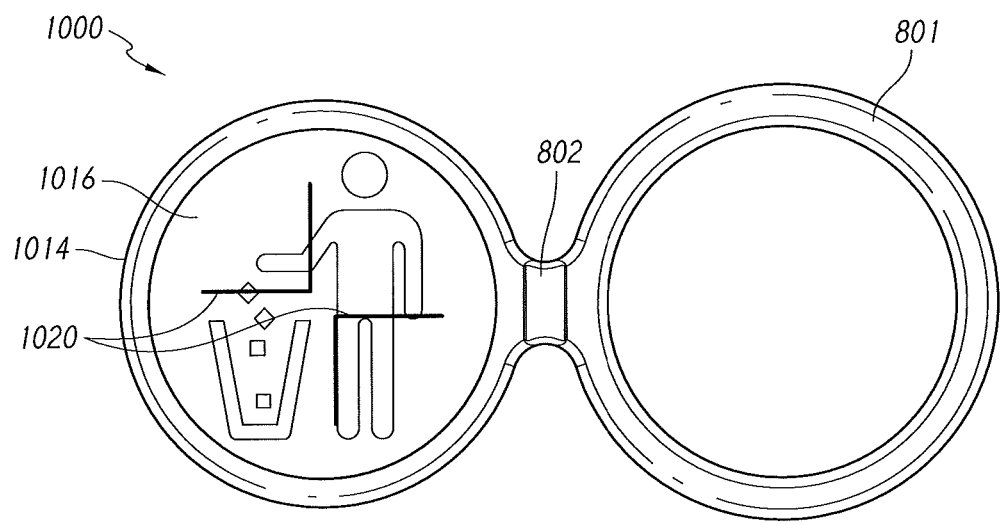
FIG. 41B illustrates a top view of a cap.

FIGS. 41A and 41B illustrate an example embodiment, wherein a cap 1000 comprises a plug 1004, a disc 1014 comprising an upper surface 1016 and a lower surface 1018, a pair of ribs 1012 that are perpendicular to each other, and at least one cut-out 1020. The cut-out 1020 comprises a passageway through at least a portion of the disc 1014 to facilitate venting through the cut-out 1020. In the illustrated embodiment, two cut-outs 1020 traverse through the lower surface 1018 and the upper surface 1016 of the disc. This enables the gases within the circuit to be vented to the atmosphere. The cut-outs 1020 are positioned opposite each other and near the ribs 1012. The ribs 1012 may provide an indication as to the position of the cut-outs 1020. For example, the cut-outs 1020 can be positioned in a vertex that is defined by the ribs. Portions of the cut-outs 1020 may protrude from the upper surface 1016 of the disc 1014 as gases are vented to the atmosphere. The cut-outs 1020 give the cap 1000 the capacity to vent gases to the atmosphere while increasing or maximising the sealing that occurs between the cap 1000 and the circuit.

In the illustrated embodiment, the cut-out 1020 is illustrated as a pair of lines forming a right angle. However, in some embodiments, the cut-out 1020 comprises a slit, an orifice (for example, the orifice 920 illustrated in FIG. 40), or any other appropriate form of opening.

In an embodiment, multiple cut-outs 1020, for example, four cut-outs 1020, are used to facilitate venting of the gases from the circuit. The four cut-outs 1020 are positioned at each of the vertices formed by the ribs 1012.

In a further embodiment, the disc 1014 comprises the at least one cut-out 1020, for example, around the perimeter of the disc 1014. The at least one cut-out 1020 is subtly incorporated into the disc 1014. For example, the at least one cut-out 1020 is incorporated into a pattern, message, or drawing that appears on the upper surface 1016 of the disc 1014.

Figure 42A:
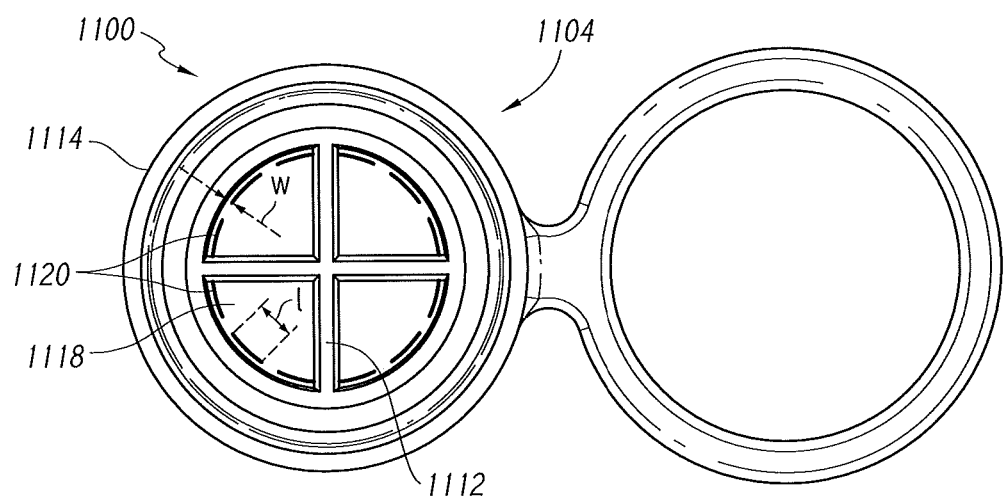
FIG. 42A illustrates a bottom view of a cap.
Figure 42B:
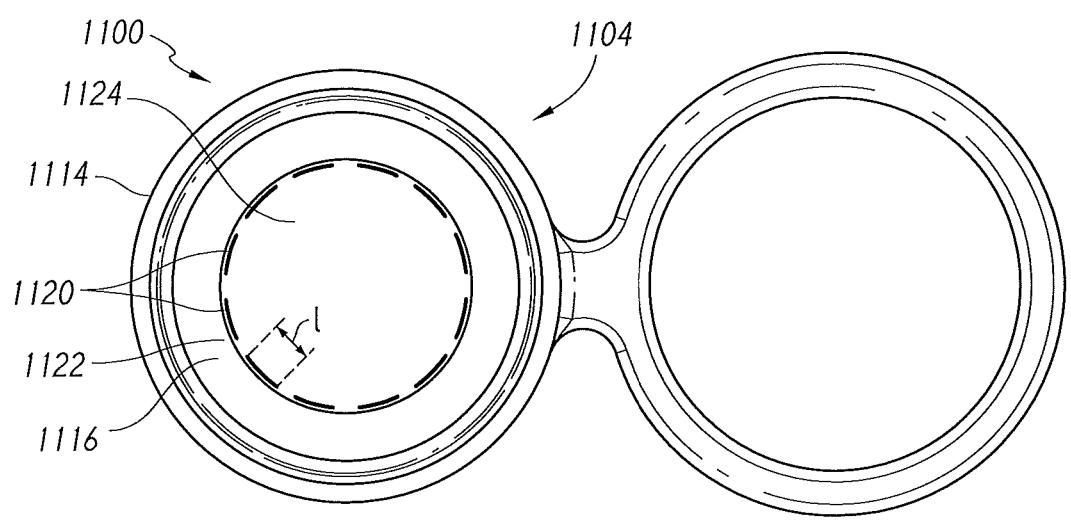
FIG. 42B illustrates a top view of a cap.

FIGS. 42A and 42B illustrate an example embodiment, wherein a cap 1100 comprises a plug 1104, a disc 1114 that further comprises an upper surface 1116 and a lower surface 1118, a pair of ribs 1112 that are perpendicular to each other, and at least one orifice 1120. The at least one orifice 1120 is configured to allow gases within the circuit to vent to the atmosphere via the disc 1114. Thus, the cap 1100 has capacity to allow venting of gases to the atmosphere while maintaining a maximum sealing force with the interior of the circuit.

In the illustrated embodiment, the cap 1100 comprises multiple orifices 1120. The orifices 1120 extend through both the lower surface 1118 and the upper surface 1116 of the disc 1114, thereby forming a passageway through which gases can move. The upper surface 1116 comprises a lowered region 1124 that is surrounded by a ledge 1122. In the illustrated embodiment, the ledge 1122 positions the lowered region 1124 2 mm below the upper surface 1116. The multiple orifices 1120 are positioned around the perimeter of the lowered region 1124 near the ledge 1122. The ledge 1122 extends at least partially over the multiple orifices 1120. This provides a tortuous path for dust or other contaminants to enter the circuit via the cap 1100. It also enables the multiple orifices 1120 to be more subtly incorporated into the cap 1100.

In an embodiment, multiple orifices 1120 comprise a small diameter, for example, between 1 mm and 5 mm. In the illustrated embodiment, the multiple orifices 1120 are 3.5 mm long (l) and 2.5 mm wide (w). This provides a tortuous path for dust or other contaminants to enter the cap 1100 and is more subtle to incorporate into the upper surface 1116 of the cap 1100.

In an embodiment, the orifices 1120 comprise a large diameter, for example, 5 mm to 10 mm. Thus, less of the orifices 1120 are used to enable gases within the circuit to vent to the atmosphere. A large diameter improves the venting capacity of the cap 1100. Thus, the cap 1100 is more likely to address what might otherwise be higher pressures of gases within the circuit. In an embodiment, the orifices 1120 on the upper surface 1116 have a length (l) of 1 mm to 10 mm, and a height of 1 mm, which extends from the lowered region 1124 into the ledge 1122.

In a further embodiment, the orifice 1120 comprises a slit or curved rectangular shape. In an embodiment, a single orifice 1120 runs along the perimeter of the lowered region 1124. In an embodiment, multiple orifices 1120, for example, two, three, or more orifices 1120, extend around the perimeter of the lowered region 1124. The orifices 1120 comprise slits that allow venting of gases from the interior of the circuit to the atmosphere.

Figure 43A:
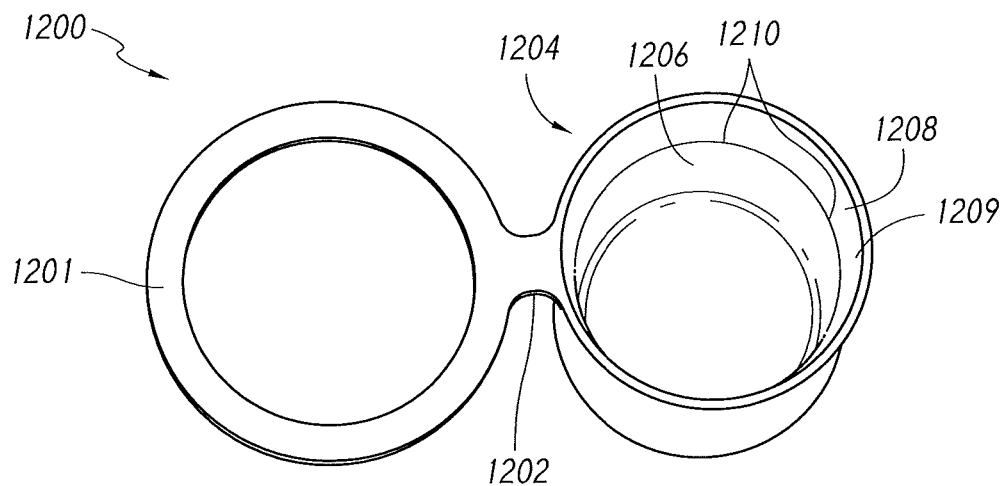
FIGS. 43A-43B illustrate perspective views of caps.
Figure 43B:
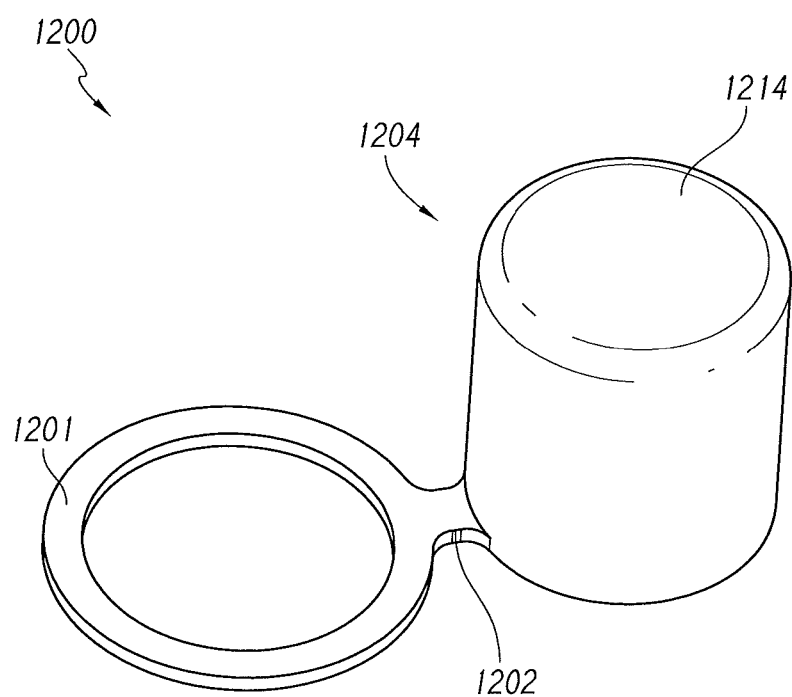

FIGS. 43A and 43B illustrate an example embodiment, wherein a cap 1200 comprises a ring 1201, a throat 1202 and a body 1204. The body 1204 comprises an inner surface 1206, an outer surface 1214, a flange 1208 and channels 1210. The ring 1201 and the throat 1202 function as described in the above embodiments. The body 1204 is a female part and, thus, is configured to receive the circuit. The exterior of the circuit and the inner surface 1206 are configured to form a sealing surface. The body 1204 comprises the flange 1208 that forms an outer rim of the body 1204. The flange 1208 is angled outwardly from the inner surface 1206 of the cap 1200. Channels 1210 are positioned adjacent to the flange 1208, between the flange 1208 and the inner surface 1206. The channels 1210 are indentations formed on the inner surface 1206 of the body 1204 and are configured to direct a gases flow from the circuit to the atmosphere. Four such channels 1210 exist in the illustrated embodiment.

In use, the cap 1200 is configured to deform if a gases source is activated. For example, pressure in the circuit causes the outer surface 1214 of the cap 1200 to deform such that the position of the cap 1200 relative to the circuit is altered. The cap 1200 moves nearer to the end of the circuit, while remaining coupled with the circuit. The inner surface 1206 of the body 1204 is no longer flush with the exterior of the circuit. This enables gases from within the circuit to vent to the atmosphere through the channels 1210.

In an embodiment, the channels 1210 comprise orifices that extend through the body 1204 of the cap 1200. This allows direct venting of gases from the circuit to the atmosphere.

In a further embodiment, multiple channels 1210, for example, greater than four channels 1210, are used to direct gases to the atmosphere. This improves the venting capacity of the cap 1200.

In a further embodiment, the length of the channels 1210 is altered such that the channels 1210 extend into the flange 1208 of the cap 1200. Thus, less deformation of the cap 1200 is required to enable gases to be directed to the atmosphere.

In a further embodiment, the flange 1208 further comprises a crimped edge 1209. The crimped edge 1209 is coupled with a channel 1210. Thus, the gases are directed by the channel 1210 to the crimped edge 1209 where they are released to the atmosphere. Thus, the crimped edge 1209 improves the efficiency by which gases are vented to the atmosphere. The crimped edge 1209 also creates a cap 1200 that is pleasing to the eye of the user. A single crimped edge 1209 is evident in the illustrated embodiment of FIG. 43A; however, multiple of the crimped edge 1209 could be used.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. While the description above refers to a "user," it should be noted that the ultimate user can be a patient and the apparatus described herein can be assembled by a nurse, doctor or other healthcare practitioner in a clinical or healthcare related facility as well as a user/patient in a home use, for example but without limitation. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Furthermore, dimensions of various components provided herein are exemplary, and other dimensions may be used. Thus, it is intended that the scope of the disclosure herein should not be limited by the particular embodiments described above.

What is claimed is:

1. A port cap for use with a humidification chamber, the port cap comprising:
    a first portion configured to cover an inlet port of the humidification chamber for shipping and/or storage; and
    a monolithic leg extending from the first portion to a distal end and configured to extend through the inlet port into the humidification chamber, the leg comprising a float contacting structure configured to contact one or more floats in the humidification chamber and restrain the one or more floats for shipping and/or storage, the leg comprising a stepped portion such that the leg transitions from a first width to a second width, wherein the float contacting structure comprises the stepped portion.

2. The port cap of claim 1, wherein the distal end of the leg comprises a chamfered edge, and the float contacting structure comprises the chamfered edge.

3. The port cap of claim 1, wherein the float contacting structure comprises a first contact structure and a second contact structure, the first contact structure being spaced apart from the second contact structure along a length of the leg.

4. The port cap of claim 3, wherein the stepped portion defines the first contact structure.

5. The port cap of claim 3, wherein the distal end of the leg defines the second contact structure.

6. The port cap of claim 3, wherein the distal end of the leg comprises a chamfered edge defining the second contact structure.

7. The port cap of claim 3, wherein the first contact structure is located along the leg between the first portion and the second contact structure.

8. The port cap of claim 3, wherein the first contact structure is adapted to contact a primary float and the second contact structure is adapted to contact a secondary float when the leg extends through the inlet port into the chamber.

9. The port cap of claim 3, wherein the leg, wherein inserted through the inlet port into the chamber, is configured to hold primary float and a secondary float in such a position that a float valve is open.

10. The port cap of claim 1, wherein the stepped portion is located in a mid-portion of the leg.

11. The port cap of claim 1, wherein the first portion comprises a lid configured to overlie the inlet port during shipping and/or storage and a flange extending downwardly from the lid.

12. The port cap of claim 11, further comprising:
a retainer coupled to the lid and at least partially defining an opening into a space configured to receive and retain a water delivery conduit; and
a sleeve coupled to the retainer, the sleeve configured to receive a spike associated with a water delivery conduit.

13. The port cap of claim 11, the first portion comprising a sleeve configured to receive a spike associated with a water delivery conduit.

14. The port cap of claim 13, wherein the sleeve is connected to a portion of the lid.

15. The port cap of claim 14, wherein the sleeve is connect to the portion of the lid with a retainer, the retainer extending laterally between portions of the flange and defining the opening.

16. The port cap of claim 11, further comprising a base comprising an opening, wherein the leg extends downwardly from the lid and extends through the opening in the base into the inlet port when the port cap is disposed on the inlet port during shipping and/or storage.

17. The port cap of claim 16, wherein when the port cap is disposed on the inlet port during shipping and/or storage, the opening in the base is configured to receive at least a portion of the inlet port.

18. The port cap of claim 1, wherein the port cap comprises two separable components.

19. The port cap of claim 1, wherein the leg of the port cap is configured to extend beyond a baffle of the inlet port of the humidification chamber.

20. The port cap of claim 1, wherein the port cap comprises a ring, tab, hook or loop configured to be grasped for removal of the port cap and/or to be attached to a medical stand.

21. The port cap of claim 1, wherein the port cap comprises a heater contact surface configured to contact a heater base of the humidification chamber.

* * * * *

UNITED STATES PATENT AND TRADEMARK OFFICE
CERTIFICATE OF CORRECTION

PATENT NO. : 10,709,866 B2
APPLICATION NO. : 15/310407
DATED : July 14, 2020
INVENTOR(S) : Sally Margaret Hensman et al.

Page 1 of 2

It is certified that error appears in the above-identified patent and that said Letters Patent is hereby corrected as shown below:

On the Title Page

On Page 2, Column 2, Item (56), Line 17, under U.S. Patent Documents, delete "Gahwi Ler" and insert --Gahwiler--.

On Page 2, Column 2, Item (56), Line 53, under U.S. Patent Documents, delete "Naumann" and insert --Haumann--.

On Page 3, Column 1, Item (56), Line 69, under U.S. Patent Documents, delete "Schermeier" and insert --Schermeier et al.--.

On Page 3, Column 2, Item (56), Line 3, under U.S. Patent Documents, after "8,640,696 B2 5/2014 Pujol et a." add --8,770,190 09-30-2014 McCarthy--.

In the Specification

In Column 1, Line 7, delete "This application" and insert --This application is a National Phase Application of PCT International Application Number PCT/NZ2015/050054, filed May 13, 2015, which--.

In Column 8, Line 41, delete "14l-14J" and insert --14I-14J--.

In Column 14, Line 54, delete "411," and insert --4H,--.

In Column 15, Line 32, delete "labels," and insert --labels, e.g.,--.

In Column 27, Line 54, delete "Tn" and insert --In--.

In Column 29, Line 27, delete "In the some configurations," and insert --In some configurations,--.

Signed and Sealed this
Twenty-fourth Day of September, 2024

Katherine Kelly Vidal
*Director of the United States Patent and Trademark Office*

CERTIFICATE OF CORRECTION (continued)
U.S. Pat. No. 10,709,866 B2

In the Claims

In Column 40, Line 9, Claim 15, delete "connect" and insert --connected--.